(12) United States Patent
Schultz et al.

(10) Patent No.: US 9,656,972 B2
(45) Date of Patent: May 23, 2017

(54) COMPOUNDS FOR TREATMENT OF CYSTIC FIBROSIS

(71) Applicant: THE CALIFORNIA INSTITUTE FOR BIOMEDICAL RESEARCH, La Jolla, CA (US)

(72) Inventors: Peter G. Schultz, La Jolla, CA (US); Arnab K. Chatterjee, San Diego, CA (US); Manoj Kumar, San Diego, CA (US); Gustav Welzel, San Diego, CA (US)

(73) Assignee: THE CALIFORNIA INSTITUTE FOR BIOMEDICAL RESEARCH, La Jolla, CA (US)

( * ) Notice: Subject to any disclaimer, the term of this patent is extended or adjusted under 35 U.S.C. 154(b) by 0 days.

(21) Appl. No.: 14/900,355

(22) PCT Filed: Jul. 2, 2014

(86) PCT No.: PCT/US2014/045301
§ 371 (c)(1),
(2) Date: Dec. 21, 2015

(87) PCT Pub. No.: WO2015/003083
PCT Pub. Date: Jan. 8, 2015

(65) Prior Publication Data
US 2016/0159754 A1   Jun. 9, 2016

Related U.S. Application Data

(60) Provisional application No. 61/842,300, filed on Jul. 2, 2013, provisional application No. 61/969,737, filed on Mar. 24, 2014.

(51) Int. Cl.
*A61K 31/497* (2006.01)
*C07D 241/28* (2006.01)
*C07D 241/32* (2006.01)
*C07D 403/12* (2006.01)
*C07D 241/34* (2006.01)
*C07C 279/18* (2006.01)

(52) U.S. Cl.
CPC .......... *C07D 241/32* (2013.01); *C07C 279/18* (2013.01); *C07D 241/28* (2013.01); *C07D 241/34* (2013.01); *C07D 403/12* (2013.01)

(58) Field of Classification Search
CPC ............................ C07D 241/28; C07D 241/32
See application file for complete search history.

(56) References Cited

U.S. PATENT DOCUMENTS

| 6,607,741 | B2 | 8/2003 | Boucher et al. |
| 2003/0044845 | A1 | 3/2003 | Jenkins et al. |
| 2004/0204424 | A1 | 10/2004 | Johnson |
| 2014/0107074 | A1 | 4/2014 | Bell et al. |

FOREIGN PATENT DOCUMENTS

| WO | WO-2007071396 A2 | 6/2007 |
| WO | WO-2007107706 A2 | 9/2007 |
| WO | WO-2008135557 A1 | 11/2008 |
| WO | WO-2009074575 A2 | 6/2009 |
| WO | WO-2013064450 A1 | 5/2013 |

OTHER PUBLICATIONS

International Application No. PCT/US2016/12360 International Search Report and Written Opinion Mailed Mar. 16, 2016.
Coote, K. et al., Camostat Attenuates Airway Epithelial Sodium Channel Function in Vivo through the Inhibition of a Channel-Activating Protease, Journal of Pharmacology and Experimental Therapeutics, 329(2); 764-774 (2009).
Fleisher, David et al., Improved Oral drug delivery: solubility limitations overcome by the use of prodrugs. Advanced Drug Delivery Reviews 19(2); 115-130 (May 22, 1996).
Hirsh, Andrew J. et al., Design, Synthesis, and Structure-Activity Relationships of Novel 2-Substituted Pyrazinoylguanidine Epithelial Sodium Channel Blockers: Drugs for Cystic Fibrosis and Chronic Bronchitis, J. Med. Chem., 49(14); 4098-4115 (Jun. 13, 2006).
Hunt, Thomas et al., Discovery of a novel chemotype of potent human ENaC blockers using a bioisostere approach. Part 1: Quaternary amines. Bioorg. Med. Chem. Lett. 22(2); 929-932 (Jan. 15, 2012).
Hunt, Thomas et al., Discovery of a novel chemotype of potent human ENaC blockers using a bioisostere approach. Part 2: a-Branched quaternary amines. Bioorg. Med. Chem. Lett. 22(8); (Apr. 15, 2012).
International Application No. PCT/US2014/045301 International Preliminary Report on Patentabiliy Mailed Jan. 14, 2016.
International Application No. PCT/US2014/045301 International Search Report and Written Opinion Mailed Oct. 31, 2014.
Saulnier et al. An Efficient Method for the Synthesis of Guanidino Prodrugs. Bioorganic and Medicinal Chemistry Letters 4(16):1985-1990 (1994).

*Primary Examiner* — Brian McDowell
(74) *Attorney, Agent, or Firm* — Wilson Sonsini Goodrich & Rosati

(57) ABSTRACT

Described herein are compounds, compositions, and methods of their use for the treatment of cystic fibrosis.

20 Claims, 2 Drawing Sheets

Sigmoidal dose-response (variable slope)
Best-fit values
| | |
|---|---|
| Bottom | -11.60 |
| Top | -6.122 |
| LogEC50 | -1.415 |
| HillSlope | 7.720 |
| EC50 | 0.03848 |

COMPOUNDS FOR TREATMENT OF CYSTIC FIBROSIS

CROSS REFERENCE TO RELATED APPLICATIONS

This application is a U.S. National Stage entry of International Application No. PCT/US2014/045301, filed Jul. 2, 2014, which claims the benefit of priority from U.S. Provisional Patent Application No. 61/842,300, filed Jul. 2, 2013, and U.S. Provisional Patent Application No. 61/969,737, filed Mar. 24, 2014, all of which are hereby incorporated by reference in their entirety.

BACKGROUND OF THE INVENTION

Cystic fibrosis (CF) is a genetic disorder affecting approximately 70,000 people worldwide. It is characterized by a defective cystic fibrosis transmembrane conductance regulator (CFTR) that causes the build-up of mucus in the lungs. CFTR and the epithelial sodium channel (ENaC) are responsible for maintaining appropriate hydration of the airway surface liquid (ASL) lining the lungs' epithelia. When CFTR function is impaired, the net action of ENaC may dehydrate the ASL resulting in thick, sticky mucus that is difficult to remove and leads to chronic infection and inflammation.

SUMMARY OF THE INVENTION

In one aspect, provided herein are compounds of Formula (I), or pharmaceutically acceptable salts, solvates, polymorphs, prodrugs, metabolites, deuterides, N-oxides, stereoisomers, or isomers thereof:

$$Y^1\text{-}L^1\text{-}B^1\text{-}A^1\text{-}X\text{-}A^2\text{-}B^2\text{-}L^2\text{-}Y^2 \quad \text{Formula (I)}$$

wherein:

$A^1$ and $A^2$ are independently selected from:

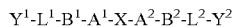

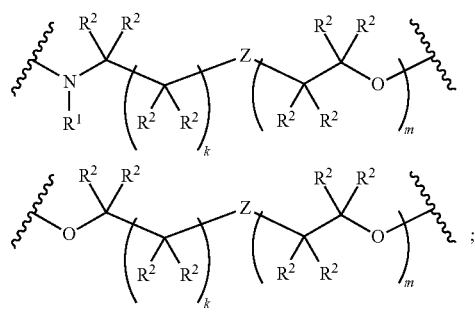

$B^1$ and $B^2$ are independently selected from:

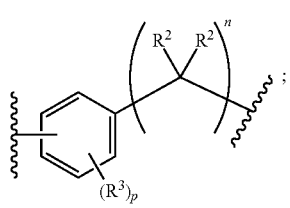

$L^1$ and $L^2$ are independently selected from:

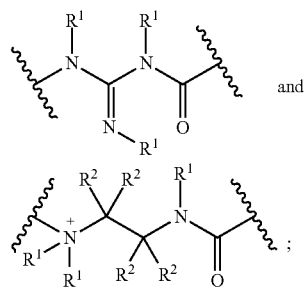

$Y^1$ and $Y^2$ are independently selected from:

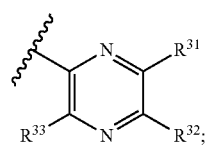

X is —C(O)—, —C(O)C(O)—,

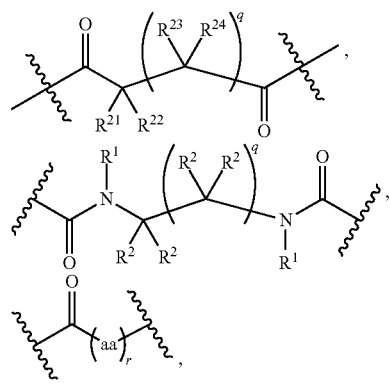

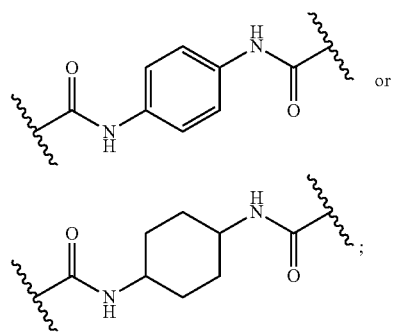

Z is O or $CR^2R^2$;
aa is

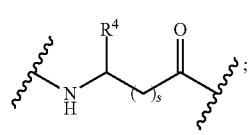

each $R^1$ is independently selected from H, alkyl, haloalkyl, arylalkyl, and heteroarylalkyl;

each R² is independently selected from H, halo, —CN, —SR¹, alkyl, cycloalkyl, haloalkyl, —OR¹, —CO₂R¹, and -(alkylene)-(CO₂R¹);

each R³ is independently selected from halo, alkyl, —CN, haloalkyl, —OR¹, and —NR¹R¹;

each R⁴ is independently selected from —CO₂R¹, -(alkylene)-(CO₂R¹), hydroxyalkyl, -(alkylene)(S(O)ₜ)(alkyl), -(alkylene)(NR⁵R⁵), and

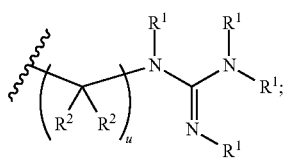

each R⁵ is independently selected from H, alkyl, haloalkyl, arylalkyl, heteroarylalkyl, aryl, and heteroaryl;

each R²¹, R²², R²³, and R²⁴ are independently selected from H, halo, —CN, —SR¹, alkyl, cycloalkyl, haloalkyl, —NR¹R¹, and —OR¹;

R³¹, R³², and R³³ are independently selected from halo, alkyl, —CN, haloalkyl, —OR¹, and —NR¹R¹;

each k is independently selected from 1, 2, 3, 4, 5, 6, 7, 8, 9, and 10;

each m is independently selected from 0, 1, 2, 3, 4, 5, 6, 7, 8, 9, and 10;

each n is independently selected from 1, 2, 3, 4, 5, 6, 7, 8, 9, and 10;

each p is independently selected from 0, 1, 2, 3, and 4;

q is 1, 2, 3, 4, 5, 6, 7, 8, 9, or 10;

r is 3, 4, 5, 6, or 7;

each s is independently selected from 0, 1, 2, 3, and 4;

each t is independently selected from 0, 1, and 2; and each u is independently selected from 1, 2, 3, 4, 5, 6, 7, 8, 9, and 10.

In some embodiments described above or below of a compound of Formula (I), Y¹ and Y² are the same. In some embodiments described above or below of a compound of Formula (I), Y¹ and Y² are the same and R³¹, R³², and R³³ are independently selected from halo and NR¹R¹. In some embodiments described above or below of a compound of Formula (I), Y¹ and Y² are the same and R³¹, R³², and R³³ are independently selected from halo and NH₂. In some embodiments described above or below of a compound of Formula (I), Y¹ and Y² are both

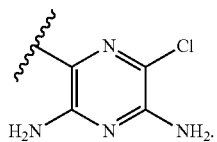

In some embodiments described above or below of a compound of Formula (I), B¹ and B² are the same. In some embodiments described above or below of a compound of Formula (I), B¹ and B² are both

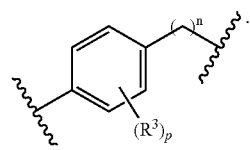

In some embodiments described above or below of a compound of Formula (I), n is 1, 2, 3, 4, or 5. In some embodiments described above or below of a compound of Formula (I), n is 3 or 4.

In some embodiments described above or below of a compound of Formula (I), p is 0.

In some embodiments described above or below of a compound of Formula (I), A¹ and A² are the same. In some embodiments described above or below of a compound of Formula (I), A¹ and A² are not the same. In some embodiments described above or below of a compound of Formula (I), A¹ and A² are both

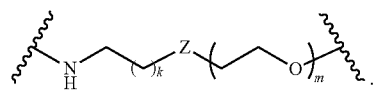

In some embodiments described above or below of a compound of Formula (I), A¹ and A² are both

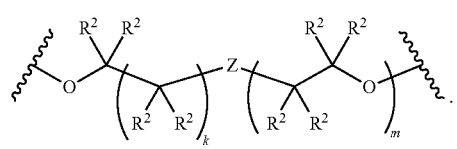

In some embodiments described above or below of a compound of Formula (I), Z is O.

In some embodiments described above or below of a compound of Formula (I), k is 1.

In some embodiments described above or below of a compound of Formula (I), each m is independently 0, 1, 2, or 3.

In some embodiments described above or below of a compound of Formula (I), L¹ and L² are the same. In some embodiments described above or below of a compound of Formula (I), L¹ and L² are both

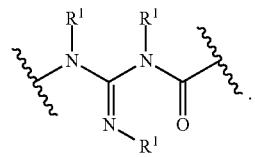

In certain embodiments described above or below of a compound of Formula (I), L¹ and L² are both

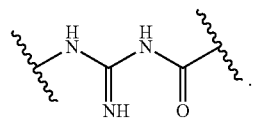 [SMILES: *NC(=N)NC(*)=O]

In some embodiments described above or below of a compound of Formula (I), L¹ and L² are both

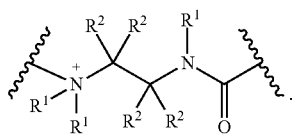

In certain embodiments described above or below of a compound of Formula (I), L¹ and L² are both

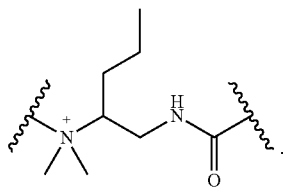

In some embodiments described above or below of a compound of Formula (I), X is —C(O)—. In some embodiments described above or below of a compound of Formula (I), X is —C(O)C(O)—.

In some embodiments described above or below of a compound of Formula (I), X is

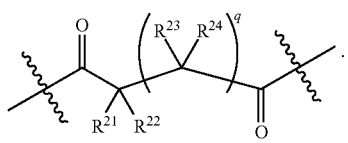

In some embodiments described above or below of a compound of Formula (I), $R^{21}$ and $R^{23}$ are the same and $R^{22}$ and $R^{24}$ are the same. In some embodiments described above or below of a compound of Formula (I), X is

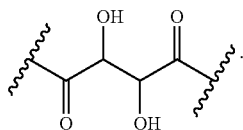 [SMILES: *C(=O)C(O)C(O)C(*)=O]

In some embodiments described above or below of a compound of Formula (I), $R^{21}$ and $R^{22}$ are the same. In some embodiments described above or below of a compound of Formula (I), $R^{23}$ and $R^{24}$ are the same. In some embodiments described above or below of a compound of Formula (I), $R^{21}$, $R^{22}$, $R^{23}$, and $R^{24}$ are the same. In some embodiments described above or below of a compound of Formula (I), $R^{21}$, $R^{22}$, $R^{23}$, and $R^{24}$ are each hydrogen. In certain embodiments described above or below of a compound of Formula (I), X is

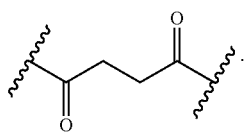 [SMILES: *C(=O)CCC(*)=O]

In some embodiments described above or below of a compound of Formula (I), X is

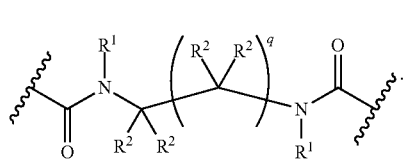

In certain embodiments described above or below of a compound of Formula (I), X is

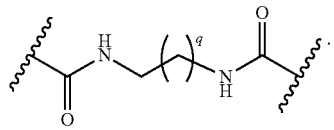

In some embodiments described above or below of a compound of Formula (I), q is 3.

In some embodiments described above or below of a compound of Formula (I), X is

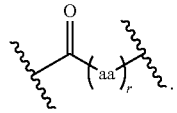

In certain embodiments described above or below of a compound of Formula (I), aa is selected from:

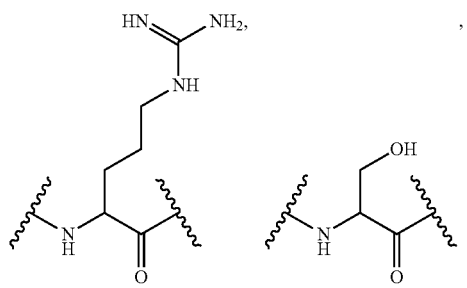

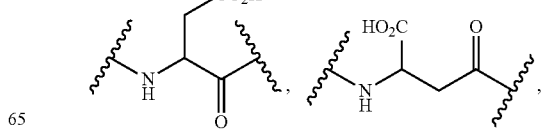

-continued

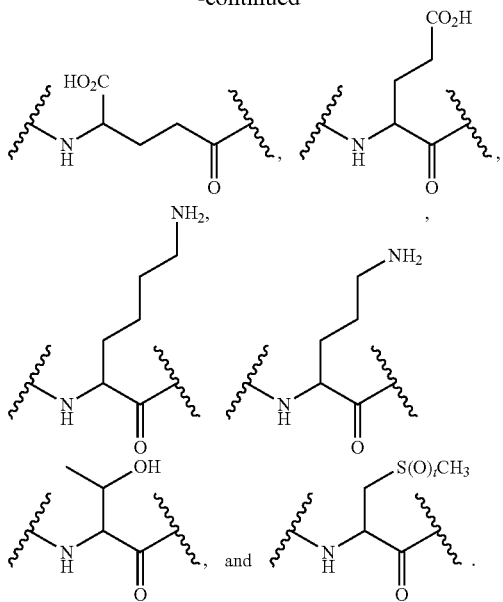

In some embodiments described above or below of a compound of Formula (I), r is 4, 5, or 6.

In some embodiments described above or below of a compound of Formula (I), X is

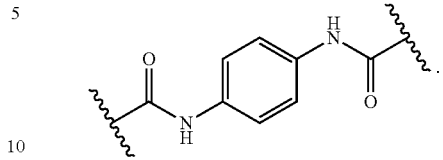

In some embodiments described above or below of a compound of Formula (I), X is

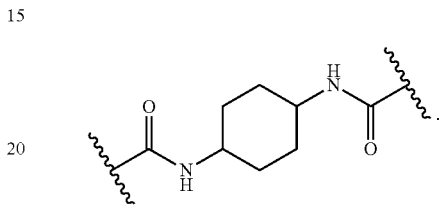

In one aspect, provided herein are compounds, or pharmaceutically acceptable salts, solvates, polymorphs, prodrugs, metabolites, N-oxides, stereoisomers, or isomers thereof, selected from:

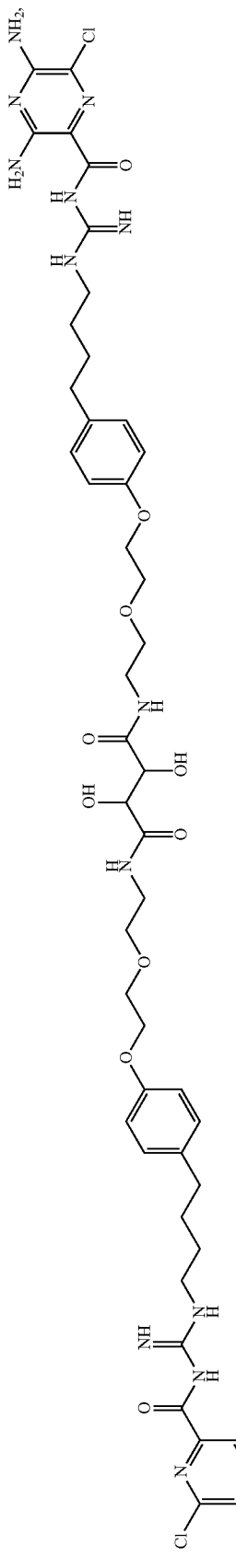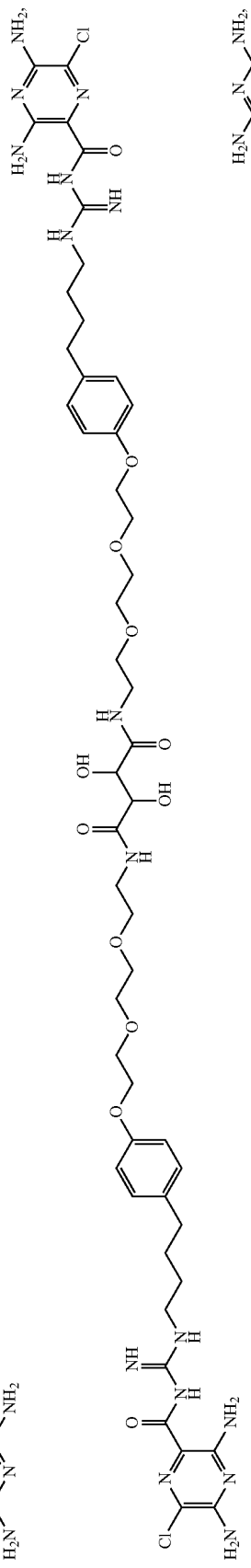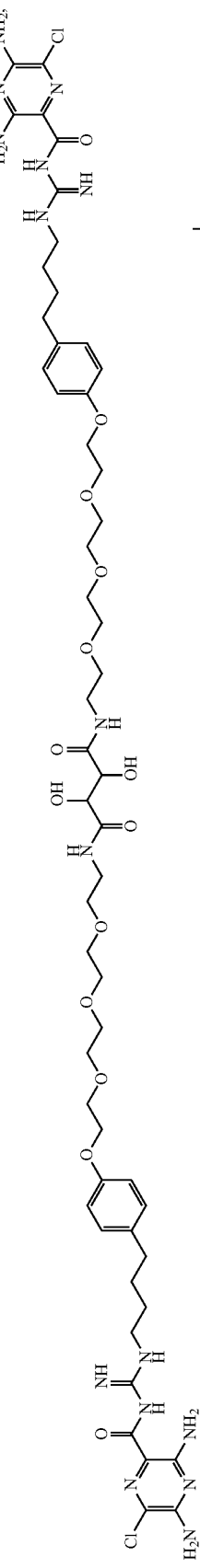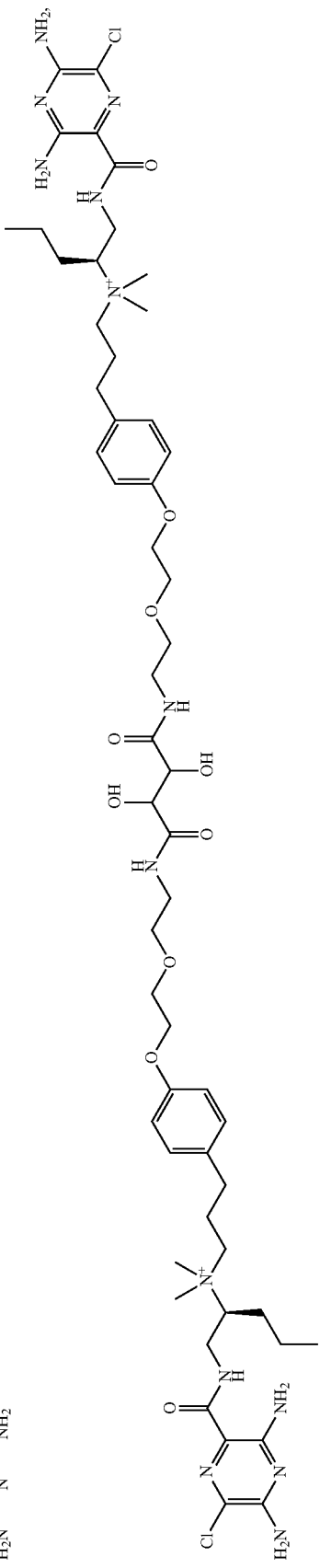

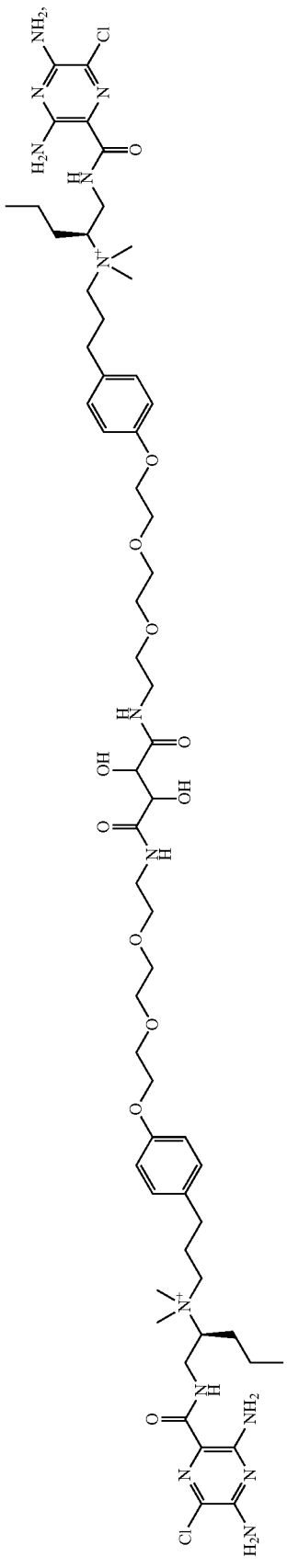
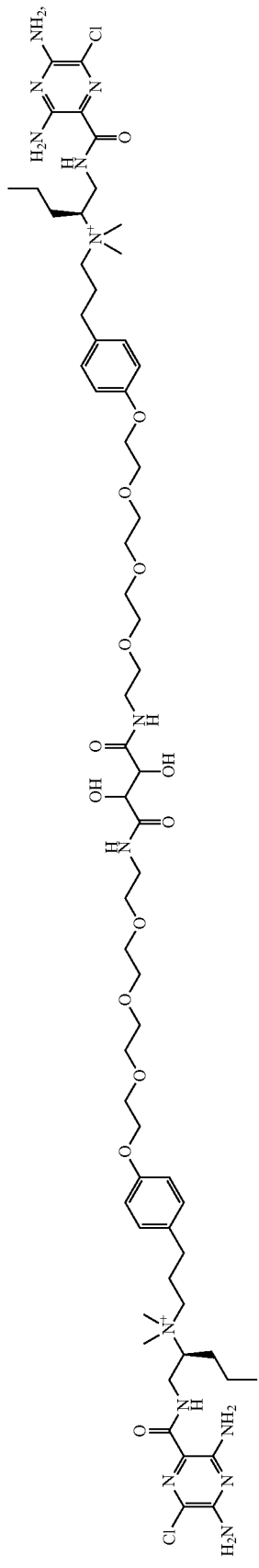
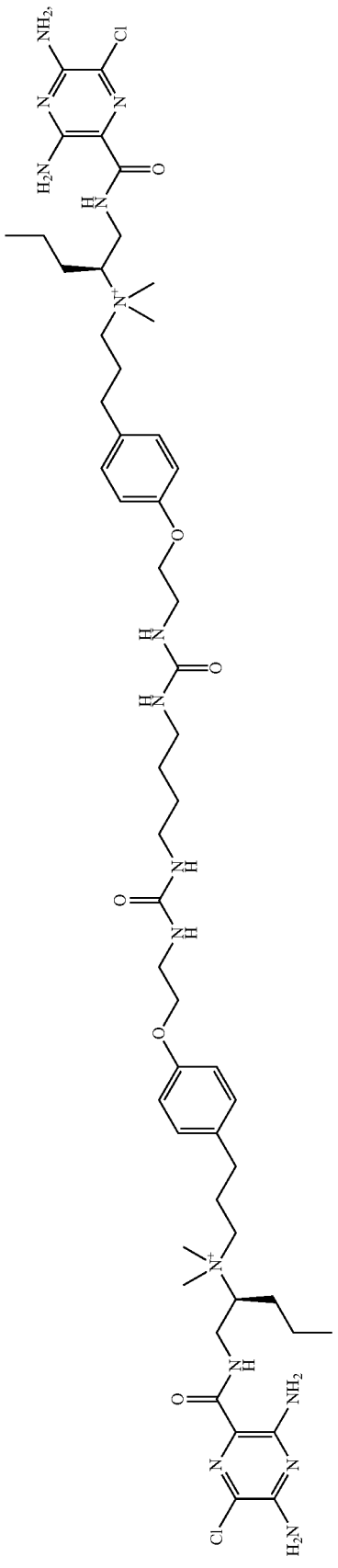

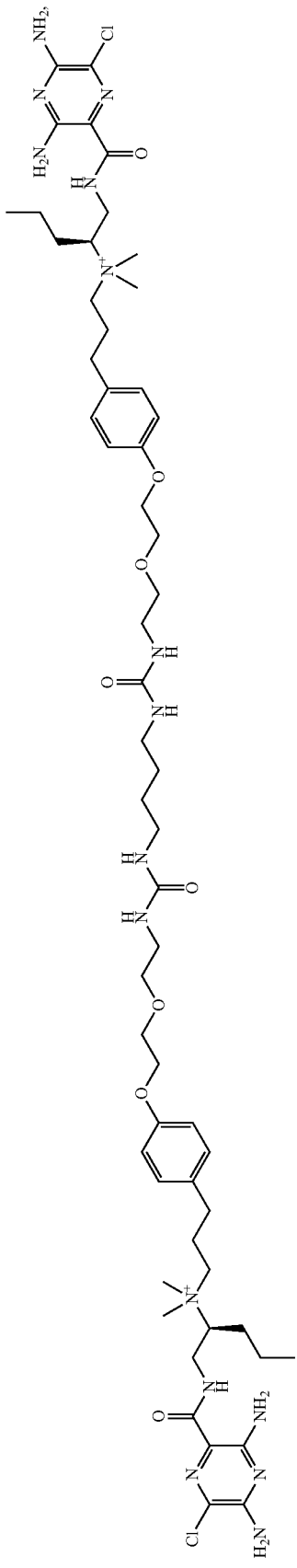
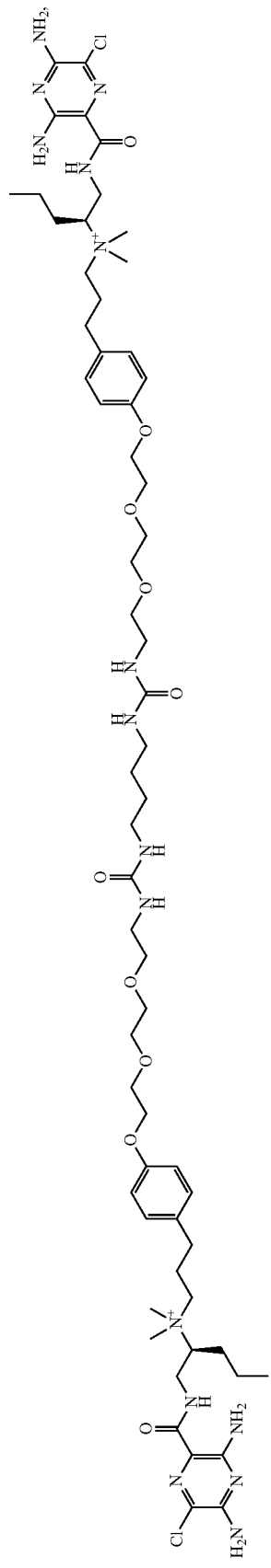
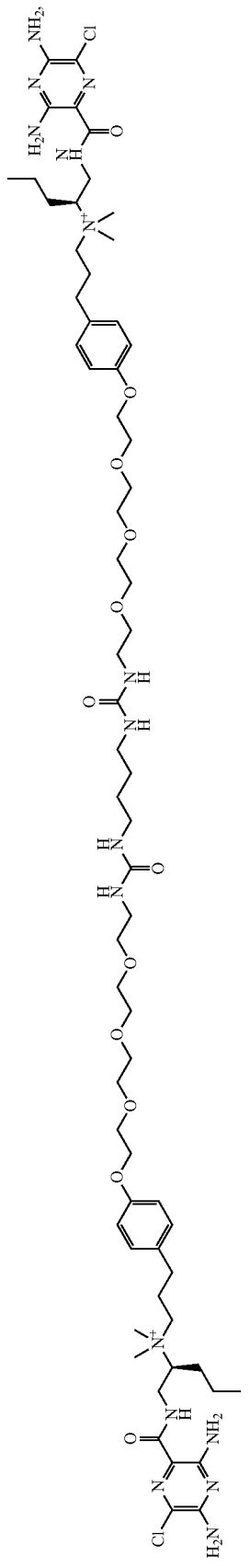

-continued
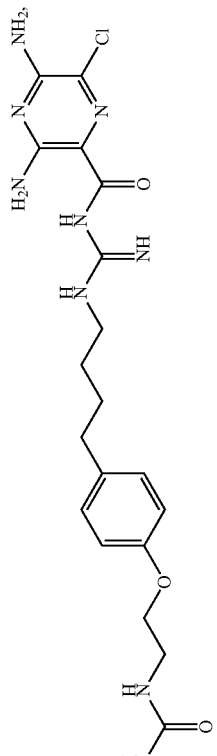
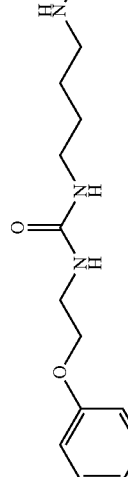
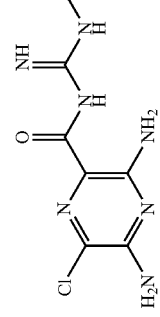
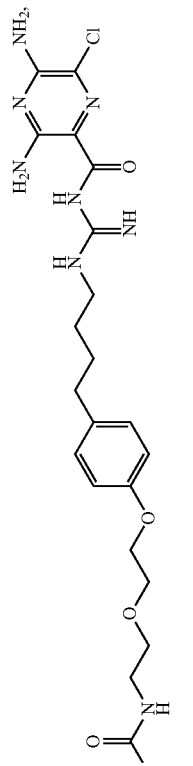
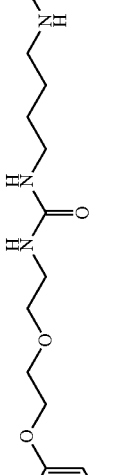
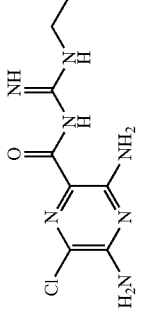
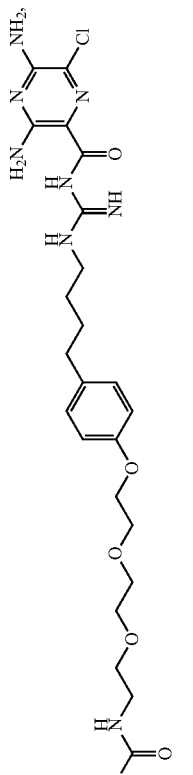
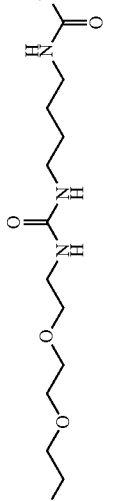
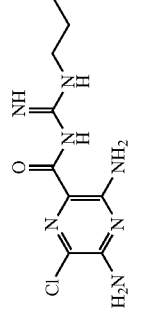

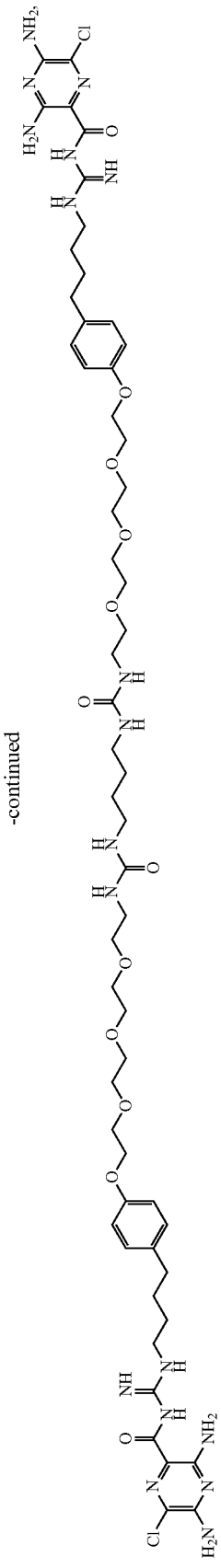
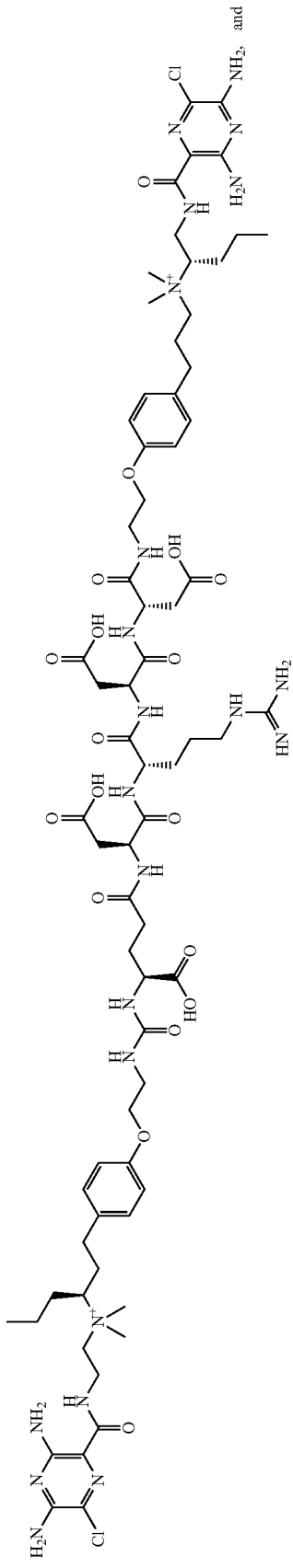
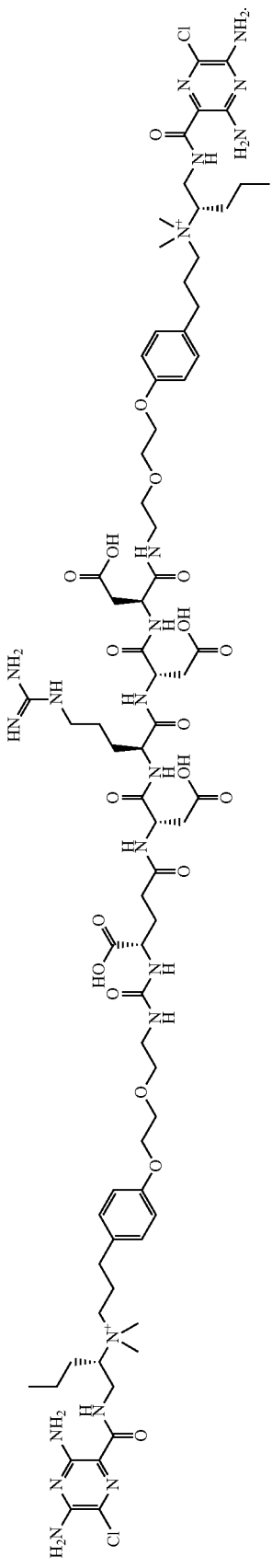

In another aspect, provided herein are compounds, or pharmaceutically acceptable salts, solvates, polymorphs, prodrugs, metabolites, N-oxides, stereoisomers, or isomers thereof, selected from:
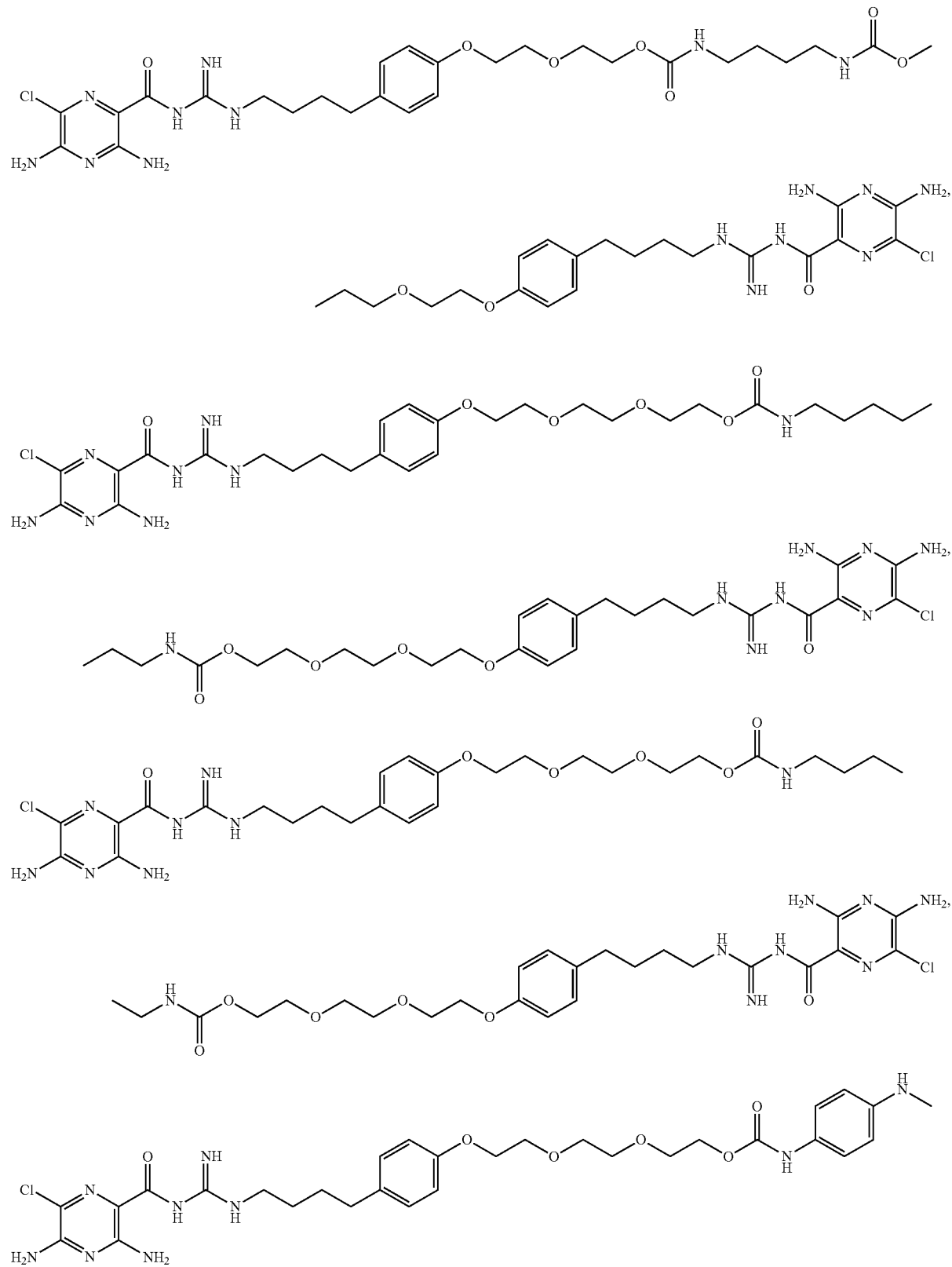

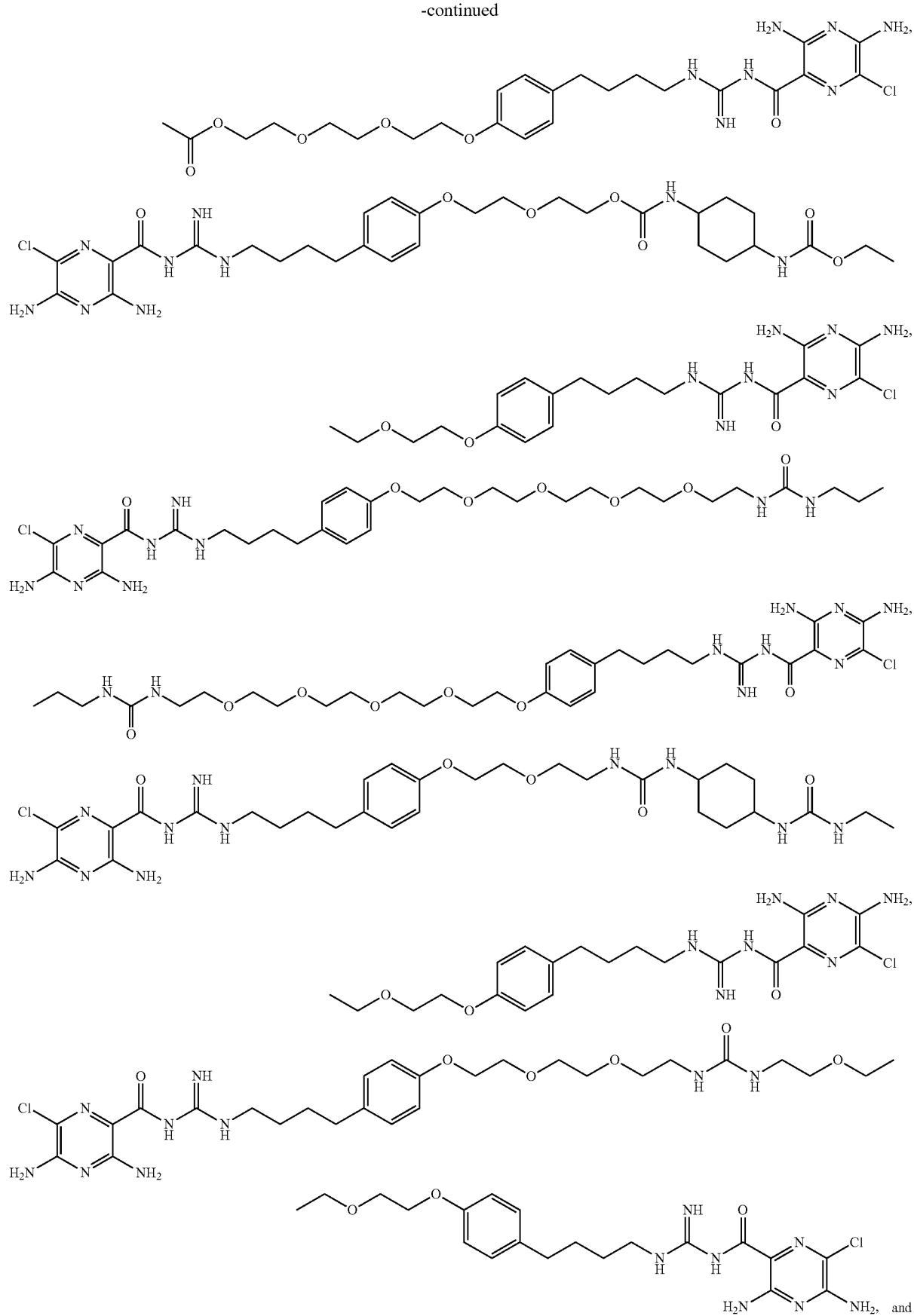

-continued

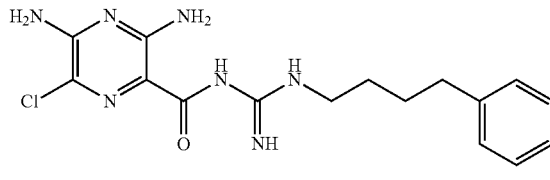

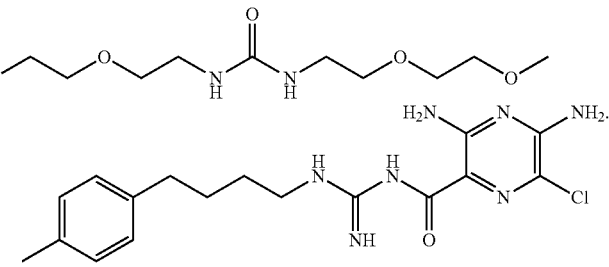

Also provided herein is a pharmaceutical composition comprising a compound of Formula (I) or as described above and below, or a pharmaceutically acceptable salt, solvate, polymorph, prodrug, metabolite, N-oxide, stereoisomer, or isomer thereof, and a pharmaceutically acceptable excipient.

Further provided herein is a method to treat cystic fibrosis, the method comprising administering a compound of Formula (I) or as described above and below.

Further provided herein is a method to treat chronic obstructive pulmonary disease, the method comprising administering a compound of Formula (I) or as described above and below.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
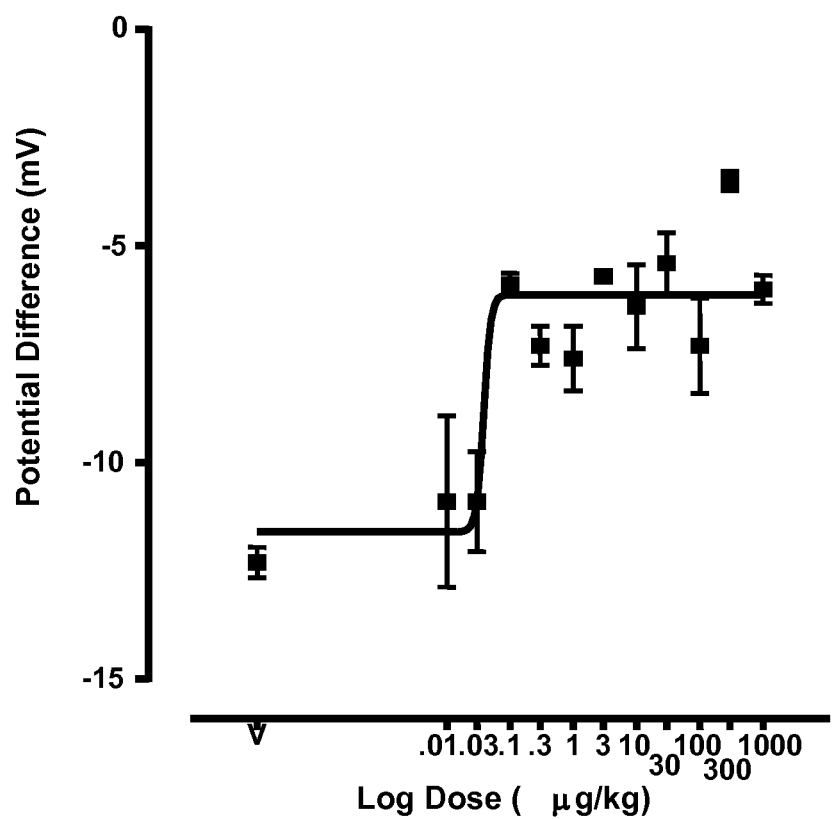
FIG. 1 shows the ED50 determination for compound 28.

Cystic fibrosis (CF) is a genetic disorder affecting approximately 70,000 people worldwide. CF patients in the US have a median life expectancy of less than 40 years, and among these patients, the leading cause of death is respiratory failure from chronic bacterial infection. CF most critically affects the lungs and is characterized by the build-up of mucus resulting from a defective cystic fibrosis transmembrane conductance regulator (CFTR).

CFTR and the epithelial sodium channel (ENaC) are ion channels regulating the transport of chloride and sodium. In the lungs, the channels are responsible for maintaining appropriate hydration of the airway surface liquid (ASL) lining the epithelia. When CFTR function is impaired, as in CF patients, the net action of ENaC may dehydrate the ASL resulting in thick, sticky mucus that is difficult to remove and leads to chronic infection and inflammation.

Current therapies, including antibacterial agents and physiotherapy, target the symptoms of CF, but there is still a need for treatments that focus on its underlying causes.

Recent studies have identified the inhibition of ENaC to rehydrate the airway lumen and improve mucus clearance. Amiloride is a classic ENaC blocker, but its effectiveness is limited by its limited potency and poor pharmacokinetic properties.

Disclosed herein are compounds which are dimeric derivatives of amiloride. These dimeric compounds disclosed herein are ENaC blockers that demonstrate improved potency and/or PK properties, for instance limited systemic exposure, and they are useful for the treatment of cystic fibrosis. Also disclosed herein are compositions comprising such compounds, and methods of their use for the inhibition of ENaC and the treatment of cystic fibrosis.

Chronic obstructive pulmonary disease (COPD) is a type of obstructive lung disease characterized by chronically poor airflow. COPD is a major cause of disability, and it's one of the leading causes of death in the United States. Currently, millions of people are diagnosed with COPD. The main symptoms include shortness of breath, cough, and sputum production. The ENaC inhibitor compounds disclosed herein are useful for the treatment of COPD. Also disclosed herein are compositions comprising such compounds, and methods of their use for the inhibition of ENaC and the treatment of COPD.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a", "an", and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Nitro" refers to the —NO$_2$ radical.

"Oxo" refers to the =O substituent.

"Oxime" refers to the =N—OH substituent.

"Thioxo" refers to the =S substituent.

"Alkyl" refers to a straight or branched hydrocarbon chain radical, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

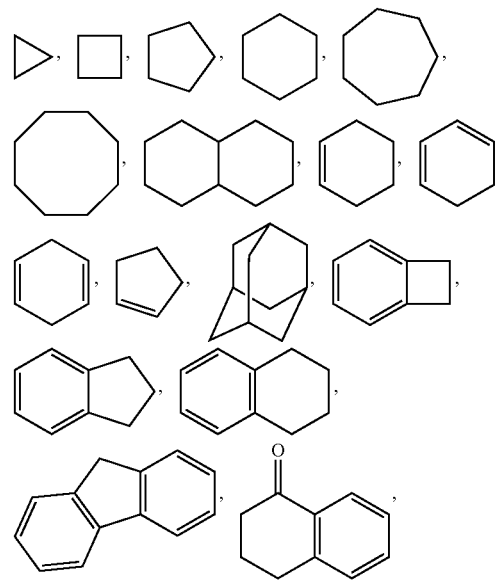

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

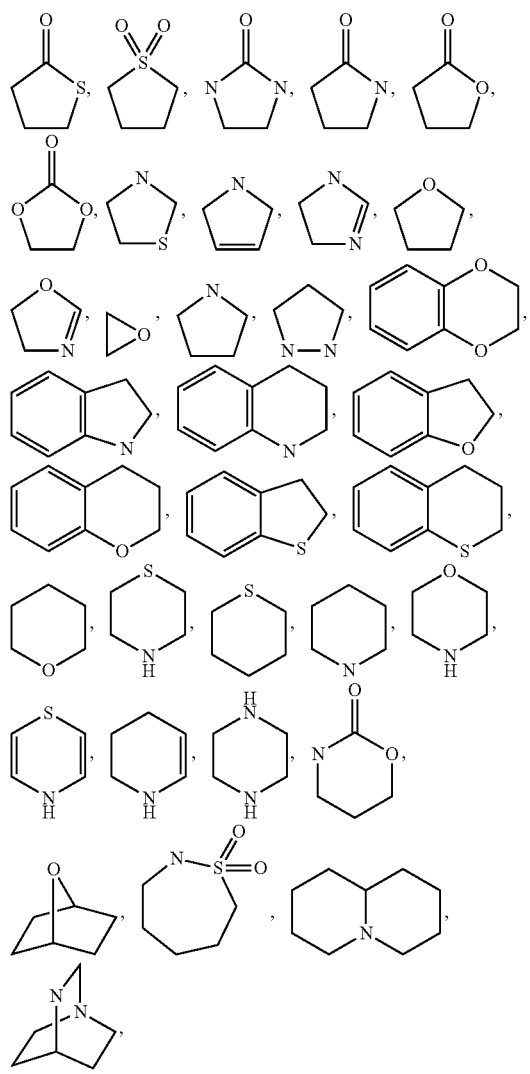

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, azepinyl, phenazinyl, benzimidazolyl, benzindolyl, benzofuranyl, benzofuranonyl, benzoxazolyl, benzothiazolyl, benzothiadiazolyl, benzothiophenyl, benzoxadiazolyl, benzodioxolyl, benzo[b][1,4]dioxepinyl, 1,4-benzodioxanyl, benzonaphthofuranyl, benzotriazolyl, benzodioxolyl, benzodioxinyl, benzopyranyl, benzopyranonyl, benzothienyl (benzothiophenyl), benzo[4,6]imidazo[1,2-a]pyridinyl, carbazolyl, cinnolinyl, dibenzofuranyl, dibenzothiophenyl, furanonyl, imidazolyl, indolyl, isoxazolyl, isoquinolinyl, indolizinyl, indazolyl, isoindolyl, indolinyl, isoindolinyl, indolizinyl, isothiazolyl, isoindolyloxadiazolyl, indazolyl, naphthyridinyl, oxadiazolyl, 2-oxoazepinyl, oxiranyl, 1-oxidopyridinyl, 1-oxidopyrimidinyl, 1-oxidopyrazinyl, 1-oxidopyridazinyl, 1-phenyl-1H-pyrrolyl, phenothiazinyl, phenoxazinyl, pyridinyl, pyridazinyl, pyrimidinyl, pyrazinyl, pyrrolyl, pyrazinyl, pyrazolyl, purinyl, phthalazinyl, pteridinyl, quinolinyl, quinazolinyl, quinoxalinyl, quinuclidinyl, triazolyl, tetrazolyl, thiazolyl, triazinyl, thiadiazolyl, tetrahydroquinolinyl, thiazolyl, and thiophenyl and the like, and their oxides, such as for example pyridyl-N-oxide. Illustrative examples of heteroaryl groups include the following moieties:

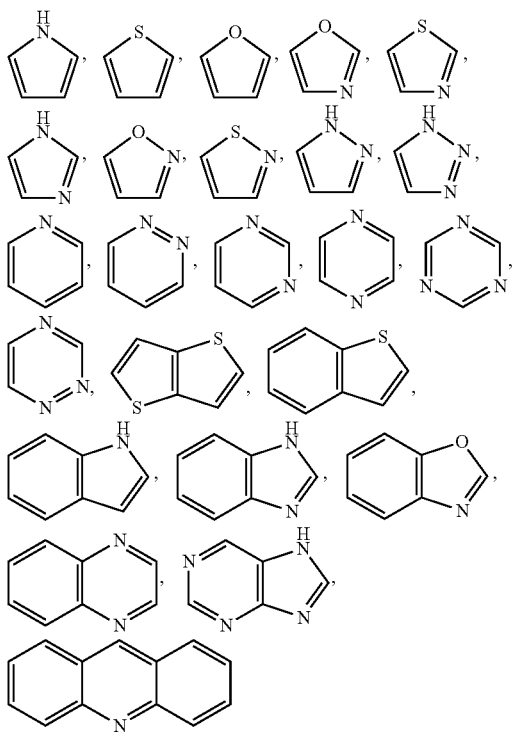

and the like.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The label

in a compound fragment denotes the attachment point to the remainder of the compound. Compound fragments containing two

can be attached to the remainder of the compound in either orientation. For example, when B$^1$ is

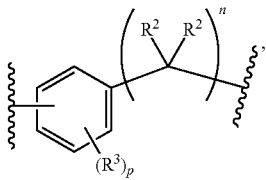

the compound of Formula (I) can be

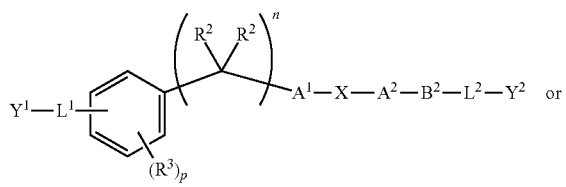

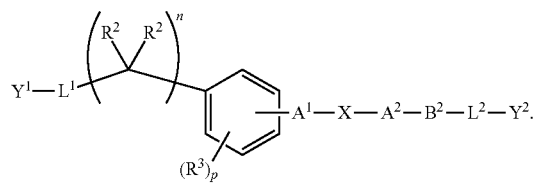

includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

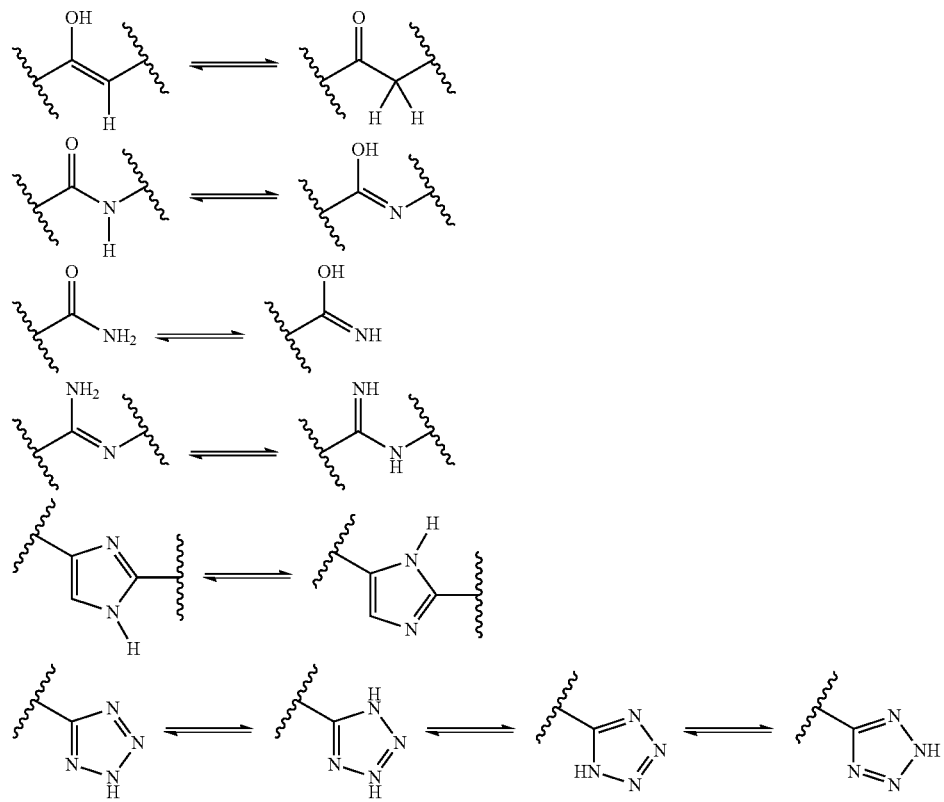

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

Described herein are compounds for the treatment of cystic fibrosis. The compounds are dimeric ENaC blockers comprising a linker with mixed hydrophobic and hydrophilic regions. These dimeric ENaC blockers demonstrate improved potency and/or PK properties compared to monomeric ENaC blockers. The dimeric ENaC compounds may show a lower systemic Cmax and/or lower systemic AUC (plasma exposure) when administered to the lung (intratracheal or by inhalation).

Also described herein are compounds for the treatment of chronic obstructive pulmonary disease (COPD).

In one aspect, provided herein are compounds of Formula (I), or pharmaceutically acceptable salts, solvates, polymorphs, prodrugs, metabolites, deuterides, N-oxides, stereoisomers, or isomers thereof:

$$Y^1\text{-}L^1\text{-}B^1\text{-}A^1\text{-}X\text{-}A^2\text{-}B^2\text{-}L^2\text{-}Y^2 \qquad \text{Formula (I)}$$

wherein $Y^1$ and $Y^2$ are independently selected from an epithelial sodium channel blocker.

In certain embodiments, provided herein are compounds of Formula (I), or pharmaceutically acceptable salts, solvates, polymorphs, prodrugs, metabolites, deuterides, N-oxides, stereoisomers, or isomers thereof:

$$Y^1\text{-}L^1\text{-}B^1\text{-}A^1\text{-}X\text{-}A^2\text{-}B^2\text{-}L^2\text{-}Y^2 \qquad \text{Formula (I)}$$

wherein:

$A^1$ and $A^2$ are independently selected from:

and

$B^1$ and $B^2$ are independently selected from:

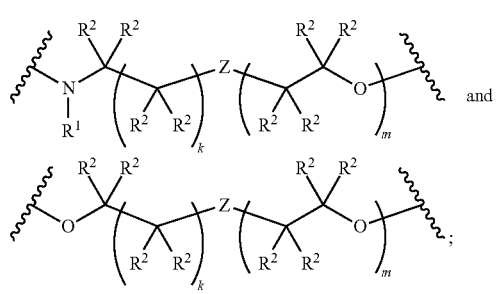

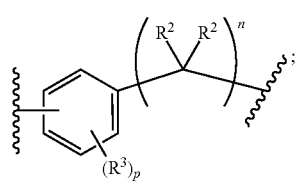

$L^1$ and $L^2$ are independently selected from:

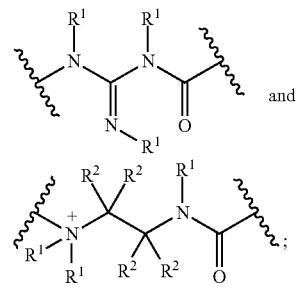
and $Y^1$ and $Y^2$ are independently selected from:

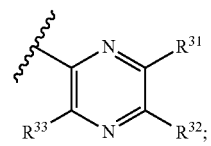

X is —C(O)—, —C(O)C(O)—,

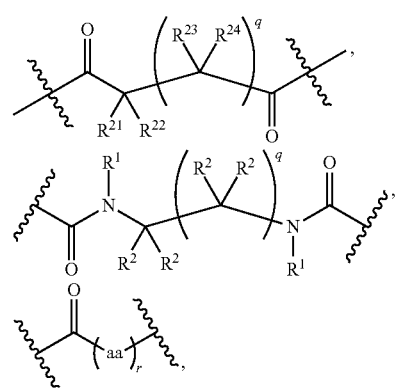

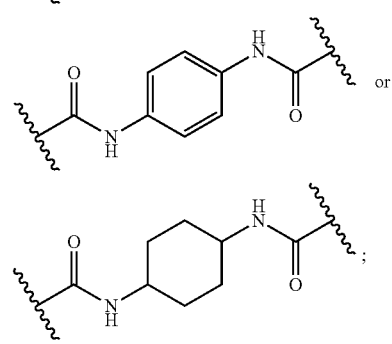

Z is O or $CR^2R^2$;

aa is

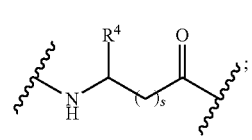

each R¹ is independently selected from H, alkyl, haloalkyl, arylalkyl, and heteroarylalkyl;

each R² is independently selected from H, halo, —CN, —SR¹, alkyl, cycloalkyl, haloalkyl, —OR¹, —CO₂R¹, and -(alkylene)-(CO₂R¹);

each R³ is independently selected from halo, alkyl, —CN, haloalkyl, —OR¹, and —NR¹R¹;

each R⁴ is independently selected from alkyl, —CO₂R¹, -(alkylene)-(CO₂R¹), hydroxyalkyl, -(alkylene)(S(O)$_t$)(alkyl), -(alkylene)(NR⁵R⁵), and

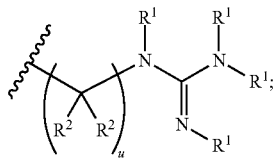

each R⁵ is independently selected from H, alkyl, haloalkyl, arylalkyl, heteroarylalkyl, aryl, and heteroaryl;

each R²¹, R²², R²³, and R²⁴ are independently selected from H, halo, —CN, —SR¹, alkyl, cycloalkyl, haloalkyl, —NR¹R¹, and —OR¹;

R³¹, R³², and R³³ are independently selected from halo, alkyl, —CN, haloalkyl, —OR¹, and —NR¹R¹;

each k is independently selected from 1, 2, 3, 4, 5, 6, 7, 8, 9, and 10;

each m is independently selected from 0, 1, 2, 3, 4, 5, 6, 7, 8, 9, and 10;

each n is independently selected from 1, 2, 3, 4, 5, 6, 7, 8, 9, and 10;

each p is independently selected from 0, 1, 2, 3, and 4;

q is 1, 2, 3, 4, 5, 6, 7, 8, 9, or 10;

r is 3, 4, 5, 6, or 7;

each s is independently selected from 0, 1, 2, 3, and 4;

each t is independently selected from 0, 1, and 2; and each u is independently selected from 1, 2, 3, 4, 5, 6, 7, 8, 9, and 10.

In some embodiments described above or below of a compound of Formula (I), Y¹ and Y² are the same. In some embodiments described above or below of a compound of Formula (I), Y¹ and Y² are the same and R³¹, R³², and R³³ are independently selected from halo and —NR¹R¹. In some embodiments described above or below of a compound of Formula (I), Y¹ and Y² are the same and R³¹, R³², and R³³ are independently selected from halo and —NH₂. In some embodiments described above or below of a compound of Formula (I), Y¹ and Y² are both

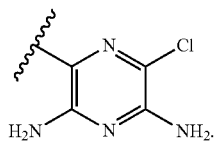

In some embodiments described above or below of a compound of Formula (I), B¹ and B² are the same. In some embodiments described above or below of a compound of Formula (I), B¹ and B² are both

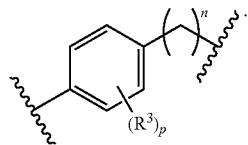

In certain embodiments described above or below of a compound of Formula (I), n is 1, 2, 3, 4, or 5. In certain embodiments described above or below of a compound of Formula (I), n is 3 or 4. In certain embodiments described above or below of a compound of Formula (I), n is 3. In certain embodiments described above or below of a compound of Formula (I), n is 4. In certain embodiments described above or below of a compound of Formula (I), p is 0. In certain embodiments described above or below of a compound of Formula (I), p is 1.

In some embodiments described above or below of a compound of Formula (I), R³ is —OR¹.

In some embodiments described above or below of a compound of Formula (I), A¹ and A² are the same. In some embodiments described above or below of a compound of Formula (I), A¹ and A² are both

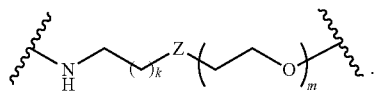

In some embodiments described above or below of a compound of Formula (I), A¹ and A² are both

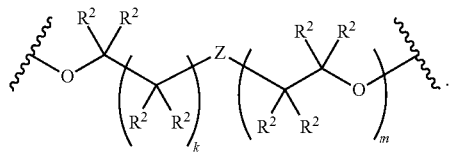

In some embodiments described above or below of a compound of Formula (I), Z is O. In certain embodiments described above or below of a compound of Formula (I), each k is independently 1, 2, or 3. In certain embodiments described above or below of a compound of Formula (I), each k is 1. In certain embodiments described above or below of a compound of Formula (I), each m is independently 0, 1, 2, or 3. In certain embodiments described above or below of a compound of Formula (I), each m is 0. In certain embodiments described above or below of a compound of Formula (I), each m is 1. In certain embodiments described above or below of a compound of Formula (I), each m is 2. In certain embodiments described above or below of a compound of Formula (I), each m is 3.

In some embodiments described above or below of a compound of Formula (I), Z is CR²R².

In some embodiments described above or below of a compound of Formula (I), L¹ and L² are the same.

In some embodiments described above or below of a compound of Formula (I), L¹ and L² are both

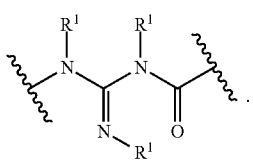

In certain embodiments described above or below of a compound of Formula (I), $L^1$ and $L^2$ are both

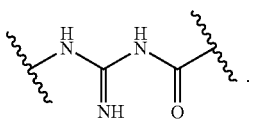 [SMILES: *NC(=N)NC(*)=O]

In some embodiments described above or below of a compound of Formula (I), $L^1$ and $L^2$ are both

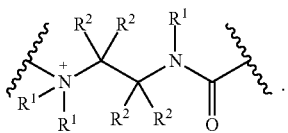

In certain embodiments described above or below of a compound of Formula (I), $L^1$ and $L^2$ are both

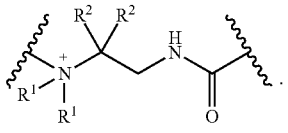

In certain embodiments described above or below of a compound of Formula (I), $L^1$ and $L^2$ are both

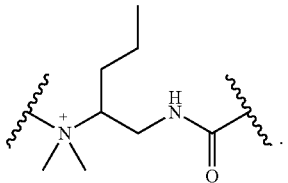

In some embodiments described above or below of a compound of Formula (I), X is —C(O)—. In some embodiments described above or below of a compound of Formula (I), X is —C(O)C(O)—.

In some embodiments described above or below of a compound of Formula (I), X is

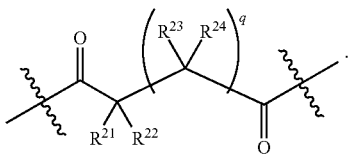

In some embodiments described above or below of a compound of Formula (I), $R^{21}$ and $R^{23}$ are the same and $R^{22}$ and $R^{24}$ are the same. In certain embodiments described above or below of a compound of Formula (I), X is

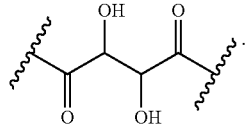

In some embodiments described above or below of a compound of Formula (I), $R^{21}$ and $R^{22}$ are the same. In some embodiments described above or below of a compound of Formula (I), $R^{23}$ and $R^{24}$ are the same. In some embodiments described above or below of a compound of Formula (I), $R^{21}$, $R^{22}$, $R^{23}$, and $R^{24}$ are the same. In some embodiments described above or below of a compound of Formula (I), $R^{21}$, $R^{22}$, $R^{23}$, and $R^{24}$ are each hydrogen. In certain embodiments described above or below of a compound of Formula (I), X is

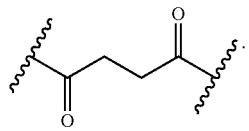 [SMILES: *C(=O)CCC(*)=O]

In some embodiments described above or below of a compound of Formula (I), X is

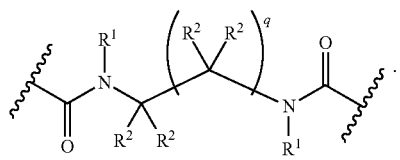

In certain embodiments described above or below of a compound of Formula (I), X is

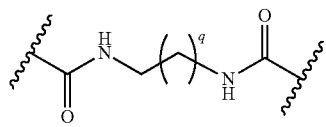

In certain embodiments described above or below of a compound of Formula (I), q is 2, 3, 4, or 5. In certain embodiments described above or below of a compound of Formula (I), q is 3.

In some embodiments described above or below of a compound of Formula (I), X is

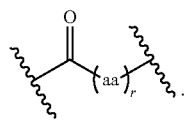

In certain embodiments described above or below of a compound of Formula (I), aa is selected from:

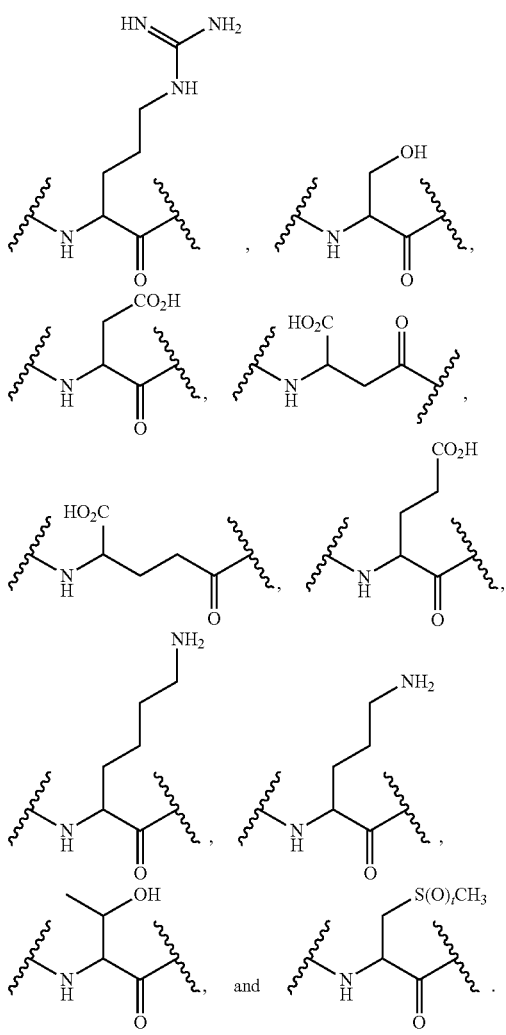

In some embodiments described above or below of a compound of Formula (I), r is 4, 5, or 6.

In some embodiments described above or below of a compound of Formula (I), X is

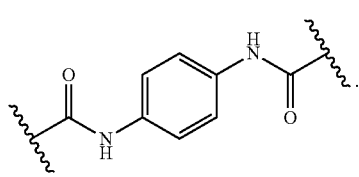 [SMILES: *C(=O)Nc1ccc(NC(*)=O)cc1]

In some embodiments described above or below of a compound of Formula (I), X is

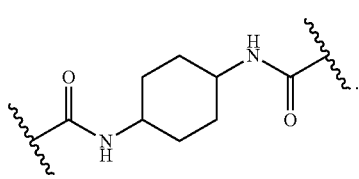 [SMILES: *C(=O)NC1CCC(NC(*)=O)CC1]

In another embodiment, provided herein are compounds of Formula (Ia), or pharmaceutically acceptable salts, solvates, polymorphs, prodrugs, metabolites, deuterides, N-oxides, stereoisomers, or isomers thereof:

$$Y^1\text{-}L^1\text{-}B^1\text{-}A^1\text{-}X\text{-}A^2\text{-}B^2\text{-}L^2\text{-}Y^2 \qquad \text{Formula (Ia)}$$

wherein:

$A^1$ and $A^2$ are independently selected from:

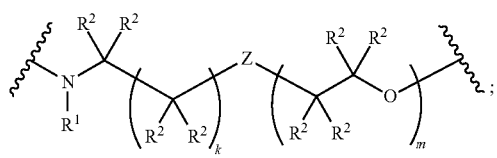

$B^1$ and $B^2$ are independently selected from:

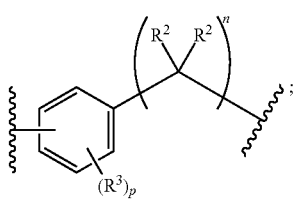

$L^1$ and $L^2$ are independently selected from:

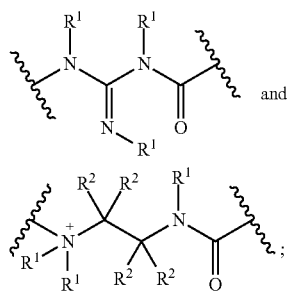

$Y^1$ and $Y^2$ are independently selected from:

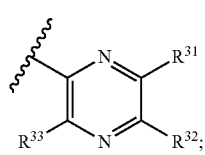

X is —C(O)—, —C(O)C(O)—,

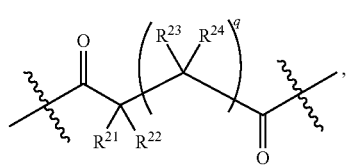

-continued

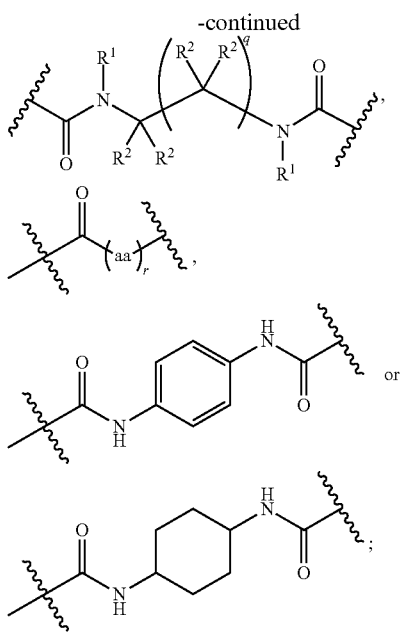

Z is O or CR²R²;
aa is

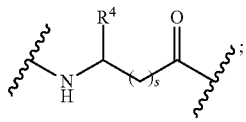

each R¹ is independently selected from H, alkyl, haloalkyl, arylalkyl, and heteroarylalkyl;
each R² is independently selected from H, halo, —CN, —SR¹, alkyl, cycloalkyl, haloalkyl, —OR¹, —CO₂R¹, and -(alkylene)-(CO₂R¹);
each R³ is independently selected from halo, alkyl, —CN, haloalkyl, —OR¹, and —NR¹R¹;
each R⁴ is independently selected from alkyl, —CO₂R¹, -(alkylene)-(CO₂R¹), hydroxyalkyl, -(alkylene)(S(O)$_t$)(alkyl), -(alkylene)(NR⁵R⁵), and

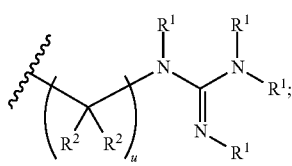

each R⁵ is independently selected from H, alkyl, haloalkyl, arylalkyl, heteroarylalkyl, aryl, and heteroaryl;
each R²¹, R²², R²³, and R²⁴ are independently selected from H, halo, —CN, —SR¹, alkyl, cycloalkyl, haloalkyl, —NR¹R¹, and —OR¹;
R³¹, R³², and R³³ are independently selected from halo, alkyl, —CN, haloalkyl, —OR¹, and —NR¹R¹;
each k is independently selected from 1, 2, 3, 4, 5, 6, 7, 8, 9, and 10;
each m is independently selected from 0, 1, 2, 3, 4, 5, 6, 7, 8, 9, and 10;
each n is independently selected from 1, 2, 3, 4, 5, 6, 7, 8, 9, and 10;
each p is independently selected from 0, 1, 2, 3, and 4;
q is 1, 2, 3, 4, 5, 6, 7, 8, 9, or 10;
r is 3, 4, 5, 6, or 7;
each s is independently selected from 0, 1, 2, 3, and 4;
each t is independently selected from 0, 1, and 2; and
each u is independently selected from 1, 2, 3, 4, 5, 6, 7, 8, 9, and 10.

In some embodiments described above or below of a compound of Formula (Ia), Y¹ and Y² are the same. In some embodiments described above or below of a compound of Formula (Ia), Y¹ and Y² are the same and R³¹, R³², and R³³ are independently selected from halo and —NR¹R¹. In some embodiments described above or below of a compound of Formula (Ia), Y¹ and Y² are the same and R³¹, R³², and R³³ are independently selected from halo and —NH₂. In some embodiments described above or below of a compound of Formula (Ia), Y¹ and Y² are both

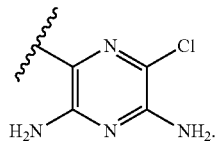

In some embodiments described above or below of a compound of Formula (Ia), B¹ and B² are the same. In some embodiments described above or below of a compound of Formula (Ia), B¹ and B² are both

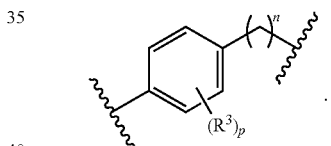

In certain embodiments described above or below of a compound of Formula (Ia), each n is independently selected from 1, 2, 3, 4, and 5. In certain embodiments described above or below of a compound of Formula (Ia), each n is independently selected from 3 or 4. In certain embodiments described above or below of a compound of Formula (Ia), each n is 3. In certain embodiments described above or below of a compound of Formula (Ia), each n is 4. In certain embodiments described above or below of a compound of Formula (Ia), each p is 0. In certain embodiments described above or below of a compound of Formula (Ia), each p is 1.

In some embodiments described above or below of a compound of Formula (Ia), R³ is —OR¹.

In some embodiments described above or below of a compound of Formula (Ia), A¹ and A² are the same. In some embodiments described above or below of a compound of Formula (Ia), A¹ and A² are both

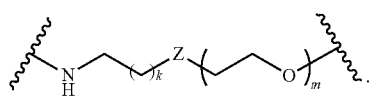

In some embodiments described above or below of a compound of Formula (Ia), Z is O. In certain embodiments described above or below of a compound of Formula (Ia), each k is independently 1, 2, or 3. In certain embodiments described above or below of a compound of Formula (Ia), each k is 1. In certain embodiments described above or below of a compound of Formula (Ia), each m is independently 0, 1, 2, or 3. In certain embodiments described above or below of a compound of Formula (Ia), each m is 0. In certain embodiments described above or below of a compound of Formula (Ia), each m is 1. In certain embodiments described above or below of a compound of Formula (Ia), each m is 2. In certain embodiments described above or below of a compound of Formula (Ia), each m is 3.

In some embodiments described above or below of a compound of Formula (Ia), Z is $CR^2R^2$.

In some embodiments described above or below of a compound of Formula (Ia), $L^1$ and $L^2$ are the same.

In some embodiments described above or below of a compound of Formula (Ia), $L^1$ and $L^2$ are both

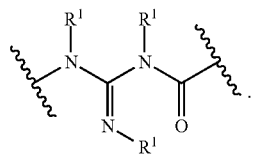

In certain embodiments described above or below of a compound of Formula (Ia), $L^1$ and $L^2$ are both

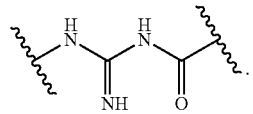

In some embodiments described above or below of a compound of Formula (Ia), $L^1$ and $L^2$ are both

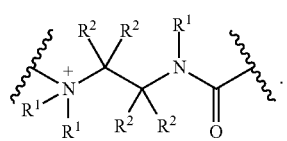

In certain embodiments described above or below of a compound of Formula (Ia), $L^1$ and $L^2$ are both

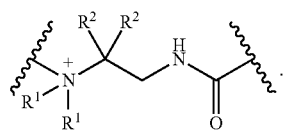

In certain embodiments described above or below of a compound of Formula (Ia), $L^1$ and $L^2$ are both

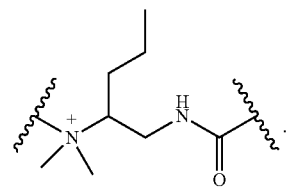

In some embodiments described above or below of a compound of Formula (Ia), X is —C(O)—. In some embodiments described above or below of a compound of Formula (Ia), X is —C(O)C(O)—.

In some embodiments described above or below of a compound of Formula (Ia), X is

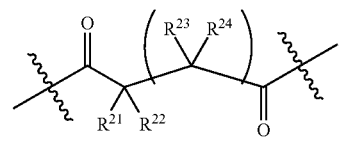

In some embodiments described above or below of a compound of Formula (Ia), $R^{21}$ and $R^{23}$ are the same and $R^{22}$ and $R^{24}$ are the same. In certain embodiments described above or below of a compound of Formula (Ia), X is

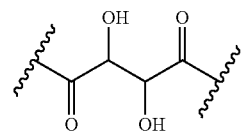

In some embodiments described above or below of a compound of Formula (Ia), $R^{21}$ and $R^{22}$ are the same. In some embodiments described above or below of a compound of Formula (Ia), $R^{23}$ and $R^{24}$ are the same. In some embodiments described above or below of a compound of Formula (Ia), $R^{21}$, $R^{22}$, $R^{23}$, and $R^{24}$ are the same. In some embodiments described above or below of a compound of Formula (Ia), $R^{21}$, $R^{22}$, $R^{23}$, and $R^{24}$ are each hydrogen. In certain embodiments described above or below of a compound of Formula (Ia), X is

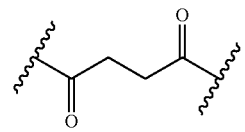

In some embodiments described above or below of a compound of Formula (Ia), X is

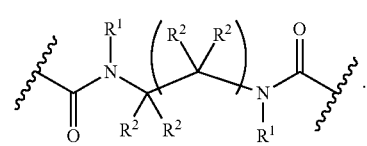

In certain embodiments described above or below of a compound of Formula (Ia), X is

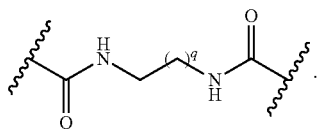

In certain embodiments described above or below of a compound of Formula (Ia), q is 2, 3, 4, or 5. In certain embodiments described above or below of a compound of Formula (Ia), q is 2. In certain embodiments described above or below of a compound of Formula (Ia), q is 3. In certain embodiments described above or below of a compound of Formula (Ia), q is 4. In certain embodiments described above or below of a compound of Formula (Ia), q is 5. In certain embodiments described above or below of a compound of Formula (Ia), q is 6. In certain embodiments described above or below of a compound of Formula (Ia), q is 7.

In some embodiments described above or below of a compound of Formula (Ia), X is

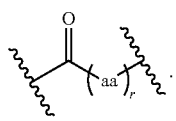

In certain embodiments described above or below of a compound of Formula (Ia), aa is selected from:

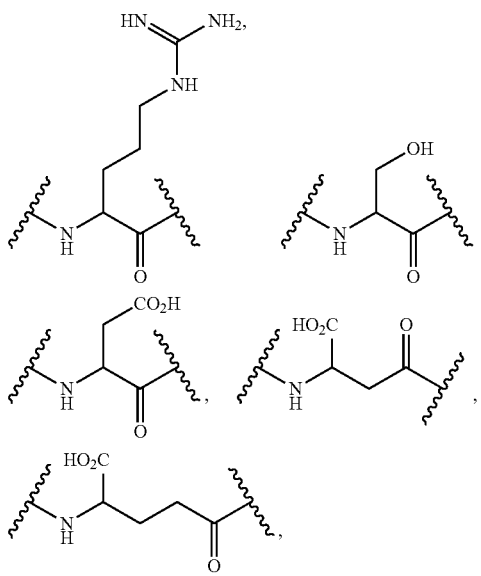

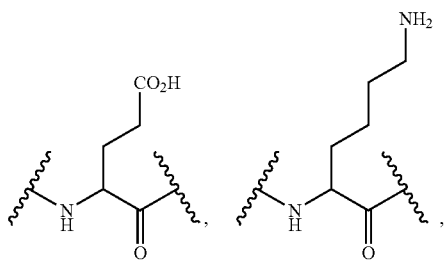

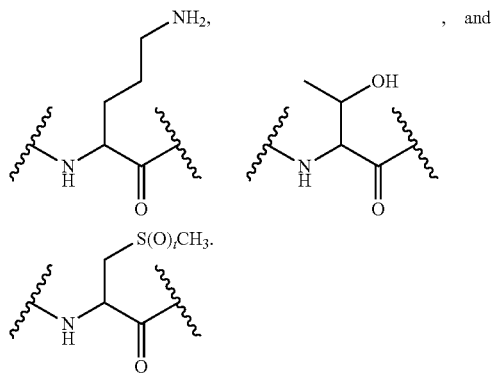

In some embodiments described above or below of a compound of Formula (Ia), r is 4, 5, or 6. In certain embodiments described above or below of a compound of Formula (Ia), r is 4. In certain embodiments described above or below of a compound of Formula (Ia), r is 5. In certain embodiments described above or below of a compound of Formula (Ia), r is 6.

In some embodiments described above or below of a compound of Formula (Ia), X is

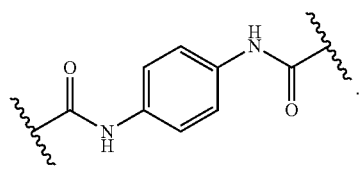 [SMILES: *C(=O)Nc1ccc(NC(*)=O)cc1]

In some embodiments described above or below of a compound of Formula (Ia), X is

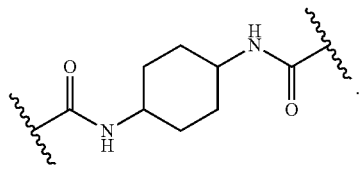 [SMILES: *C(=O)NC1CCC(NC(*)=O)CC1]

In another embodiment, provided herein are compounds of Formula (Ib), or pharmaceutically acceptable salts, solvates, polymorphs, prodrugs, metabolites, deuterides, N-oxides, stereoisomers, or isomers thereof:

$Y^1\text{-}L^1\text{-}B^1\text{-}A^1\text{-}X\text{-}A^2\text{-}B^2\text{-}L^2\text{-}Y^2$      Formula (Ib)

wherein:

$A^1$ and $A^2$ are independently selected from:

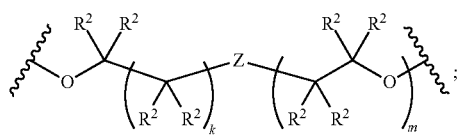

$B^1$ and $B^2$ are independently selected from:

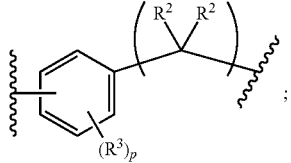

$L^1$ and $L^2$ are independently selected from:

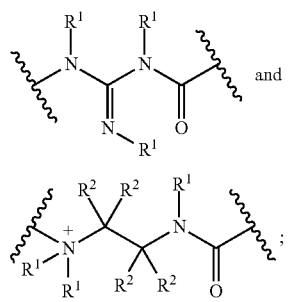

$Y^1$ and $Y^2$ are independently selected from:

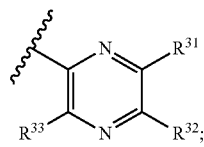

X is —C(O)—, —C(O)C(O)—,

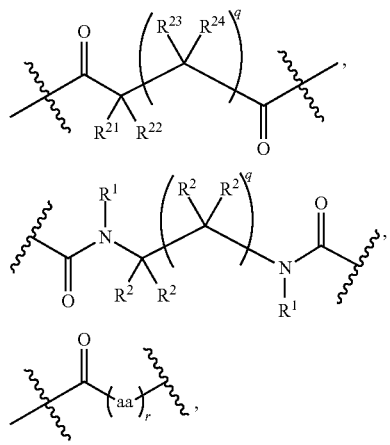

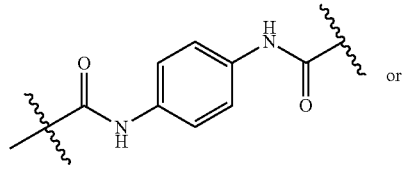

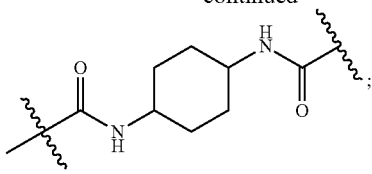

Z is O or $CR^2R^2$;
aa is

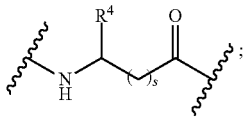

each $R^1$ is independently selected from H, alkyl, haloalkyl, arylalkyl, and heteroarylalkyl;
each $R^2$ is independently selected from H, halo, —CN, —$SR^1$, alkyl, cycloalkyl, haloalkyl, —$OR^1$, —$CO_2R^1$, and -(alkylene)-($CO_2R^1$);
each $R^3$ is independently selected from halo, alkyl, —CN, haloalkyl, —$OR^1$, and —$NR^1R^1$;
each $R^4$ is independently selected from alkyl, —$CO_2R^1$, -(alkylene)-($CO_2R^1$), hydroxyalkyl, -(alkylene)(S(O)$_t$)(alkyl), -(alkylene)($NR^5R^5$), and

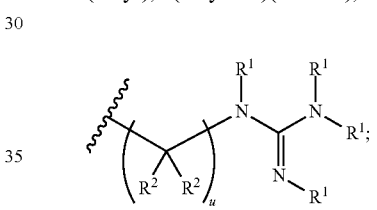

each $R^5$ is independently selected from H, alkyl, haloalkyl, arylalkyl, heteroarylalkyl, aryl, and heteroaryl;
each $R^{21}$, $R^{22}$, $R^{23}$, and $R^{24}$ are independently selected from H, halo, —CN, —$SR^1$, alkyl, cycloalkyl, haloalkyl, —$NR^1R^1$, and —$OR^1$;
$R^{31}$, $R^{32}$, and $R^{33}$ are independently selected from halo, alkyl, —CN, haloalkyl, —$OR^1$, and —$NR^1R^1$;
each k is independently selected from 1, 2, 3, 4, 5, 6, 7, 8, 9, and 10;
each m is independently selected from 0, 1, 2, 3, 4, 5, 6, 7, 8, 9, and 10;
each n is independently selected from 1, 2, 3, 4, 5, 6, 7, 8, 9, and 10;
each p is independently selected from 0, 1, 2, 3, and 4;
q is 1, 2, 3, 4, 5, 6, 7, 8, 9, or 10;
r is 3, 4, 5, 6, or 7;
each s is independently selected from 0, 1, 2, 3, and 4;
each t is independently selected from 0, 1, and 2; and
each u is independently selected from 1, 2, 3, 4, 5, 6, 7, 8, 9, and 10.

In some embodiments described above or below of a compound of Formula (Ib), $Y^1$ and $Y^2$ are the same. In some embodiments described above or below of a compound of Formula (Ib), $Y^1$ and $Y^2$ are the same and $R^{31}$, $R^{32}$, and $R^{33}$ are independently selected from halo and —$NR^1R^1$. In some embodiments described above or below of a compound of Formula (Ib), $Y^1$ and $Y^2$ are the same and $R^{31}$, $R^{32}$, and $R^{33}$ are independently selected from halo and —$NH_2$. In some embodiments described above or below of a compound of Formula (Ib), $Y^1$ and $Y^2$ are both

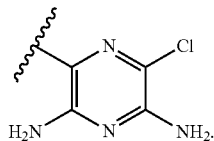

In some embodiments described above or below of a compound of Formula (Ib), $B^1$ and $B^2$ are the same. In some embodiments described above or below of a compound of Formula (Ib), $B^1$ and $B^2$ are both

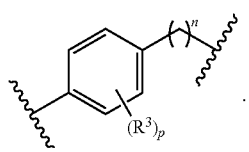

In certain embodiments described above or below of a compound of Formula (Ib), each n is independently selected from 1, 2, 3, 4, and 5. In certain embodiments described above or below of a compound of Formula (Ib), each n is independently selected from 3 or 4. In certain embodiments described above or below of a compound of Formula (Ib), each n is 3. In certain embodiments described above or below of a compound of Formula (Ib), each n is 4. In certain embodiments described above or below of a compound of Formula (Ib), each p is 0. In certain embodiments described above or below of a compound of Formula (Ib), each p is 1.

In some embodiments described above or below of a compound of Formula (Ib), $R^3$ is $-OR^1$.

In some embodiments described above or below of a compound of Formula (Ib), $A^1$ and $A^2$ are the same. In some embodiments described above or below of a compound of Formula (Ib), $A^1$ and $A^2$ are both

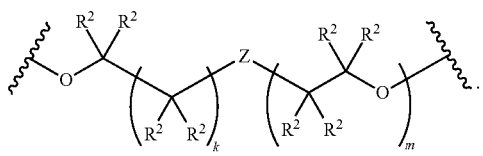

In some embodiments described above or below of a compound of Formula (Ib), Z is O. In certain embodiments described above or below of a compound of Formula (Ib), each k is independently 1, 2, or 3. In certain embodiments described above or below of a compound of Formula (Ib), each k is 1. In certain embodiments described above or below of a compound of Formula (Ib), each m is independently 0, 1, 2, or 3. In certain embodiments described above or below of a compound of Formula (Ib), each m is 0. In certain embodiments described above or below of a compound of Formula (Ib), each m is 1. In certain embodiments described above or below of a compound of Formula (Ib), each m is 2. In certain embodiments described above or below of a compound of Formula (Ib), each m is 3.

In some embodiments described above or below of a compound of Formula (Ib), Z is $CR^2R^2$.

In some embodiments described above or below of a compound of Formula (Ib), $L^1$ and $L^2$ are the same.

In some embodiments described above or below of a compound of Formula (Ib), $L^1$ and $L^2$ are both

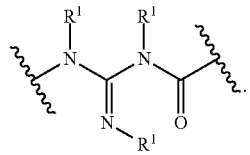

In certain embodiments described above or below of a compound of Formula (Ib), $L^1$ and $L^2$ are both

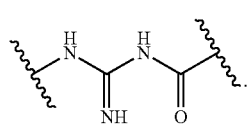 [SMILES: *NC(=N)NC(*)=O]

In some embodiments described above or below of a compound of Formula (Ib), $L^1$ and $L^2$ are both

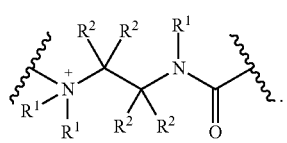

In certain embodiments described above or below of a compound of Formula (Ib), $L^1$ and $L^2$ are both

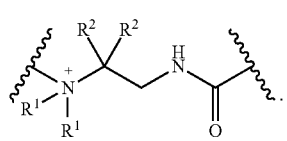

In certain embodiments described above or below of a compound of Formula (Ib), $L^1$ and $L^2$ are both

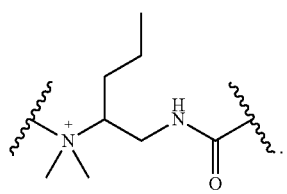

In some embodiments described above or below of a compound of Formula (Ib), X is $-C(O)-$. In some embodiments described above or below of a compound of Formula (Ib), X is $-C(O)C(O)-$.

In some embodiments described above or below of a compound of Formula (Ib), X is

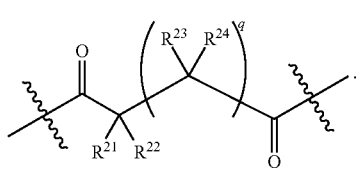

In some embodiments described above or below of a compound of Formula (Ib), $R^{21}$ and $R^{23}$ are the same and $R^{22}$ and $R^{24}$ are the same. In certain embodiments described above or below of a compound of Formula (Ib), X is

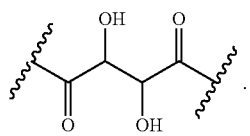 [SMILES: *C(=O)C(O)C(O)C(*)=O]

In some embodiments described above or below of a compound of Formula (Ib), $R^{21}$ and $R^{22}$ are the same. In some embodiments described above or below of a compound of Formula (Ib), $R^{23}$ and $R^{24}$ are the same. In some embodiments described above or below of a compound of Formula (Ib), $R^{21}$, $R^{22}$, $R^{23}$, and $R^{24}$ are the same. In some embodiments described above or below of a compound of Formula (Ib), $R^{21}$, $R^{22}$, $R^{23}$, and $R^{24}$ are each hydrogen. In certain embodiments described above or below of a compound of Formula (Ib), X is

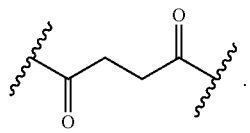

In some embodiments described above or below of a compound of Formula (Ib), X is

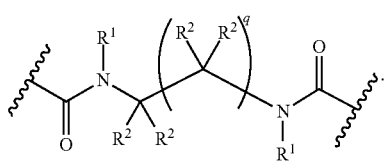

In certain embodiments described above or below of a compound of Formula (Ib), X is

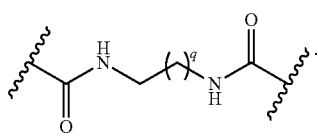

In certain embodiments described above or below of a compound of Formula (Ib), q is 2, 3, 4, or 5. In certain embodiments described above or below of a compound of Formula (Ib), q is 2. In certain embodiments described above or below of a compound of Formula (Ib), q is 3. In certain embodiments described above or below of a compound of Formula (Ib), q is 4. In certain embodiments described above or below of a compound of Formula (Ib), q is 5. In certain embodiments described above or below of a compound of Formula (Ib), q is 6. In certain embodiments described above or below of a compound of Formula (Ib), q is 7.

In some embodiments described above or below of a compound of Formula (Ib), X is

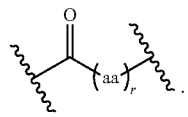

In certain embodiments described above or below of a compound of Formula (Ib), aa is selected from:

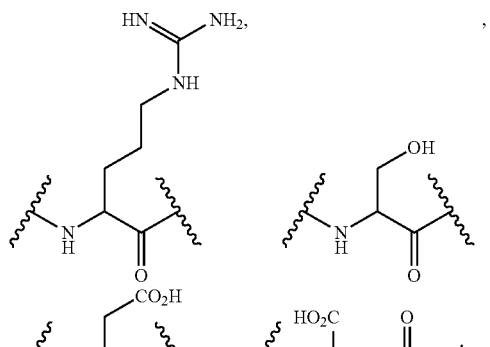

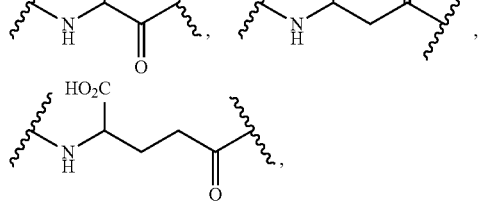

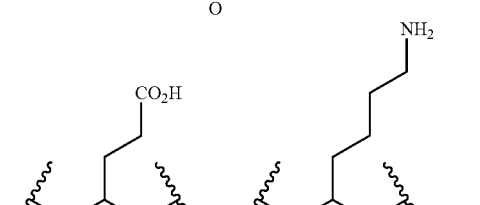

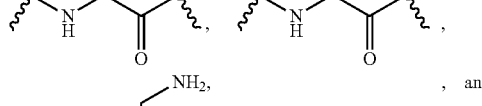

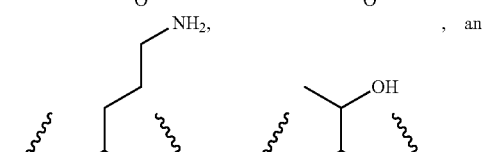

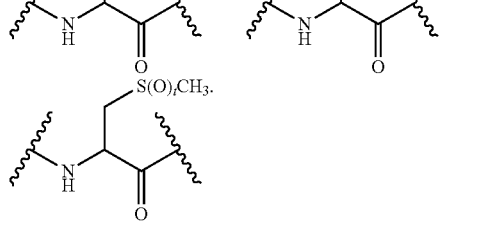

In some embodiments described above or below of a compound of Formula (Ib), r is 4, 5, or 6. In certain embodiments described above or below of a compound of Formula (Ib), r is 4. In certain embodiments described above or below of a compound of Formula (Ib), r is 5. In certain embodiments described above or below of a compound of Formula (Ib), r is 6.

In some embodiments described above or below of a compound of Formula (Ib), X is

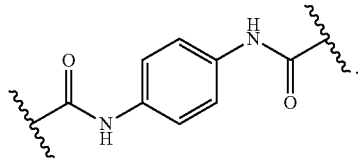 [SMILES: *C(=O)Nc1ccc(NC(*)=O)cc1]

In some embodiments described above or below of a compound of Formula (Ib), X is

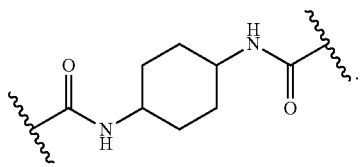 [SMILES: *C(=O)NC1CCC(NC(*)=O)CC1]

In another embodiment, provided herein are compounds of Formula (II), or pharmaceutically acceptable salts, solvates, polymorphs, prodrugs, metabolites, deuterides, N-oxides, stereoisomers, or isomers thereof:

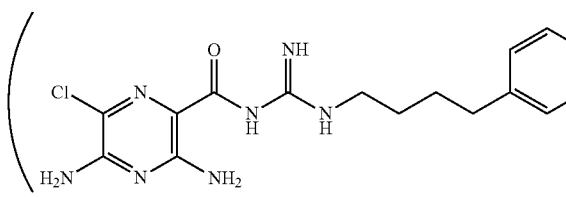

Formula (II)

wherein:
X is —C(O)—, —C(O)C(O)—,

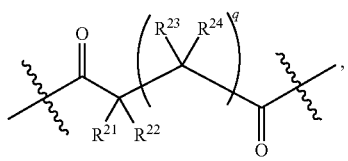

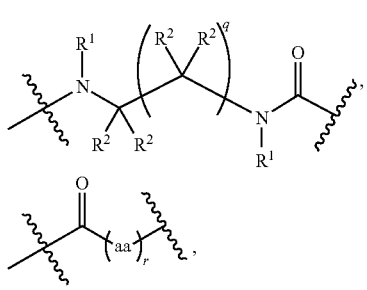

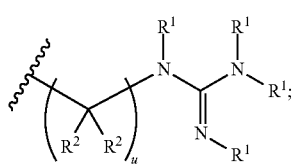

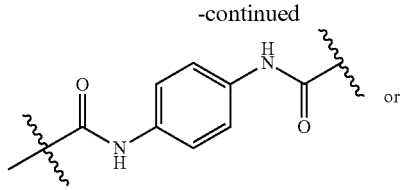

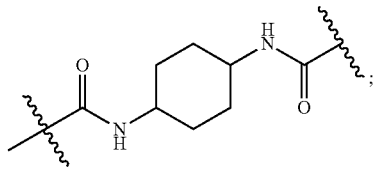

$Z^1$ is O or $CR^2R^2$;
$Z^2$ is O or NH;
aa is

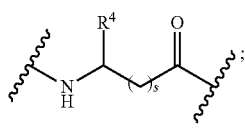

each $R^1$ is independently selected from H, alkyl, haloalkyl, arylalkyl, and heteroarylalkyl;
each $R^2$ is independently selected from H, halo, —CN, —$SR^1$, alkyl, cycloalkyl, haloalkyl, —$OR^1$, —$CO_2R^1$, and -(alkylene)-($CO_2R^1$);

each $R^4$ is independently selected from alkyl, —$CO_2R^1$, -(alkylene)-($CO_2R^1$), hydroxyalkyl, -(alkylene)(S(O)$_t$)(alkyl), -(alkylene)($NR^5R^5$), and

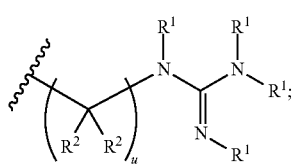

each $R^5$ is independently selected from H, alkyl, haloalkyl, arylalkyl, heteroarylalkyl, aryl, and heteroaryl;
each $R^{21}$, $R^{22}$, $R^{23}$, and $R^{24}$ are independently selected from H, halo, —CN, —$SR^1$, alkyl, cycloalkyl, haloalkyl, —$NR^1R^1$, and —$OR^1$;
each k is independently selected from 1, 2, 3, 4, 5, 6, 7, 8, 9, and 10;
each m is independently selected from 0, 1, 2, 3, 4, 5, 6, 7, 8, 9, and 10;

q is 1, 2, 3, 4, 5, 6, 7, 8, 9, or 10;

r is 3, 4, 5, 6, or 7;

each s is independently selected from 0, 1, 2, 3, and 4;

each t is independently selected from 0, 1, and 2; and each u is independently selected from 1, 2, 3, 4, 5, 6, 7, 8, 9, and 10.

In some embodiments is a compound of Formula (II) wherein X is —C(O)—. In some embodiments is a compound of Formula (II) wherein X is —C(O)C(O)—.

In some embodiments is a compound of Formula (II) wherein X is

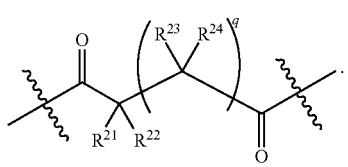

In some embodiments is a compound of Formula (II) wherein X is

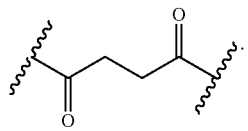 [SMILES: *C(=O)CCC(*)=O]

In some embodiments is a compound of Formula (II) wherein X is

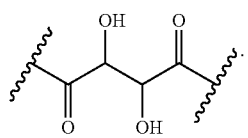 [SMILES: *C(=O)C(O)C(O)C(*)=O]

In some embodiments is a compound of Formula (II) wherein X is

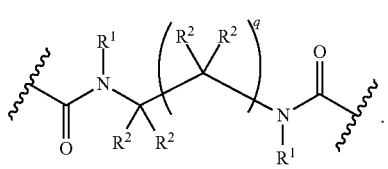

In some embodiments is a compound of Formula (II) wherein X is

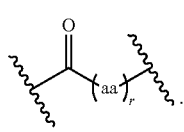

In some embodiments is a compound of Formula (II) wherein X is

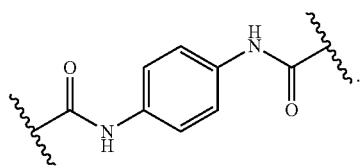 [SMILES: *C(=O)Nc1ccc(NC(*)=O)cc1]

In some embodiments is a compound of Formula (II) wherein X is

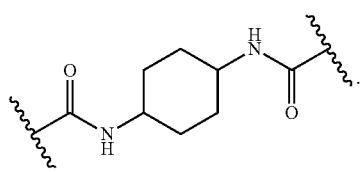 [SMILES: *C(=O)NC1CCC(NC(*)=O)CC1]

In some embodiments is a compound of Formula (II) wherein X is

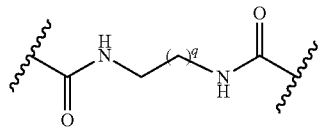

and q is 1. In some embodiments is a compound of Formula (II) wherein X is

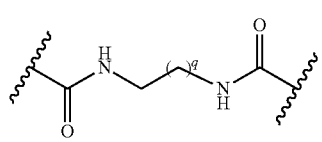

and q is 2. In some embodiments is a compound of Formula (II) wherein X is

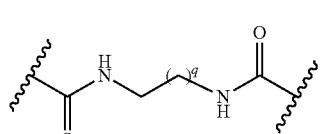

and q is 3. In some embodiments is a compound of Formula (II) wherein X is

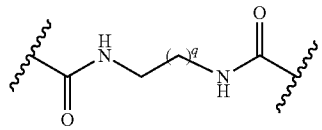

and q is 4. In some embodiments is a compound of Formula (II) wherein X is

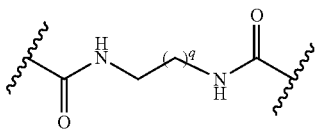

and q is 5. In some embodiments is a compound of Formula (II) wherein X is

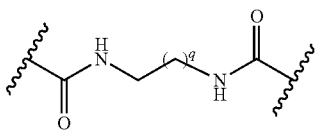

and q is 6. In some embodiments is a compound of Formula (II) wherein X is

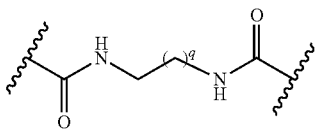

and q is 7.

In some embodiments is a compound of Formula (II) wherein $Z^1$ is O; and $Z^2$ is O. In some embodiments is a compound of Formula (II) wherein $Z^1$ is O; and $Z^2$ is NH. In some embodiments is a compound of Formula (II) wherein $Z^1$ is $CH_2$; and $Z^2$ is O. In some embodiments is a compound of Formula (II) wherein $Z^1$ is $CH_2$; and $Z^2$ is NH.

In some embodiments is a compound of Formula (II) wherein k is 1. In some embodiments is a compound of Formula (II) wherein k is 2. In some embodiments is a compound of Formula (II) wherein k is 3. In some embodiments is a compound of Formula (II) wherein k is 4. In some embodiments is a compound of Formula (II) wherein k is 5.

In some embodiments is a compound of Formula (II) wherein m is 0. In some embodiments is a compound of Formula (II) wherein m is 1. In some embodiments is a compound of Formula (II) wherein m is 2. In some embodiments is a compound of Formula (II) wherein m is 3. In some embodiments is a compound of Formula (II) wherein m is 4. In some embodiments is a compound of Formula (II) wherein m is 5. In some embodiments is a compound of Formula (II) wherein m is 6. In some embodiments is a compound of Formula (II) wherein m is 7.

In some embodiments is a compound of Formula (II) wherein X is

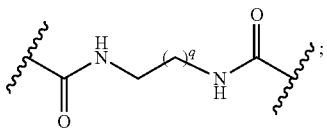

q is 1, 2, 3, 4, 5, 6, 7, 8, 9, or 10; $Z^1$ is O; $Z^2$ is O; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is

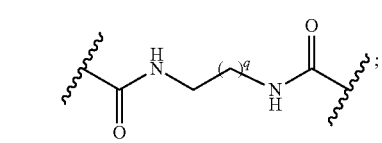

q is 1, 2, 3, 4, 5, or 6; $Z^1$ is O; $Z^2$ is O; each m is independently selected from 0, 1, 2, 3, 4, 5, and 6; and each k is independently selected from 1, 2, 3, 4, and 5. In some embodiments is a compound of Formula (II) wherein X is

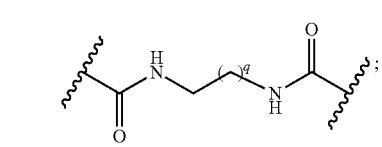

q is 3, 4, or 5; $Z^1$ is O; $Z^2$ is O; each m is independently selected from 1, 2, 3, 4, and 5; and each k is independently selected from 1, 2, and 3. In some embodiments is a compound of Formula (II) wherein X is

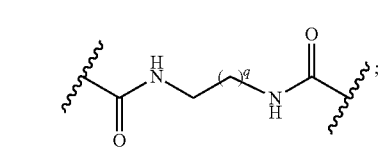

q is 3, 4, or 5; $Z^1$ is O; $Z^2$ is O; each m is independently selected from 1, 2, 3, 4, and 5; and each k is 1.

In some embodiments is a compound of Formula (II) wherein X is

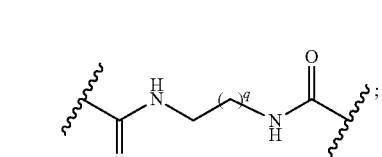

q is 1, 2, 3, 4, 5, 6, 7, 8, 9, or 10; $Z^1$ is O; $Z^2$ is NH; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is

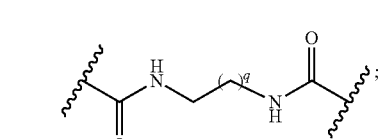

q is 1, 2, 3, 4, 5, or 6; $Z^1$ is O; $Z^2$ is NH; each m is independently selected from 0, 1, 2, 3, 4, 5, and 6; and each k is independently selected from 1, 2, 3, 4, and 5. In some embodiments is a compound of Formula (II) wherein X is

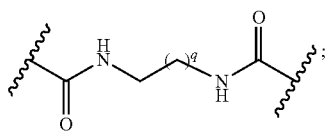

q is 3, 4, or 5; $Z^1$ is O; $Z^2$ is NH; each m is independently selected from 1, 2, 3, 4, and 5; and each k is independently selected from 1, 2, and 3. In some embodiments is a compound of Formula (II) wherein X is

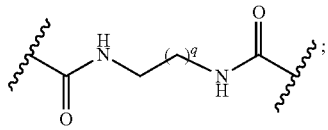

q is 3, 4, or 5; $Z^1$ is O; $Z^2$ is NH; each m is independently selected from 1, 2, 3, 4, and 5; and each k is 1.

In some embodiments is a compound of Formula (II) wherein X is

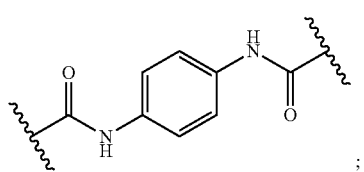 [SMILES: *C(=O)Nc1ccc(NC(*)=O)cc1]

$Z^1$ is O; $Z^2$ is O; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is Z

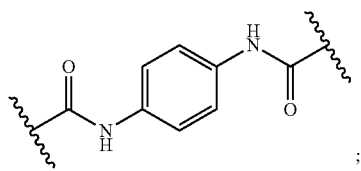 [SMILES: *C(=O)Nc1ccc(NC(*)=O)cc1]

$Z^1$ is O; $Z^2$ is O; each m is independently selected from 0, 1, 2, 3, 4, 5, and 6; and each k is independently selected from 1, 2, 3, 4, and 5. In some embodiments is a compound of Formula (II) wherein X is

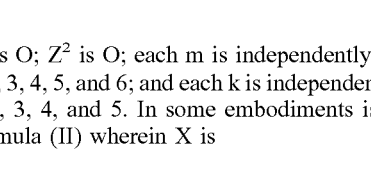

$Z^1$ is O; Z is O; each m is independently selected from 1, 2, 3, 4, and 5; and each k is independently selected from 1, 2, and 3. In some embodiments is a compound of Formula (II) wherein X is

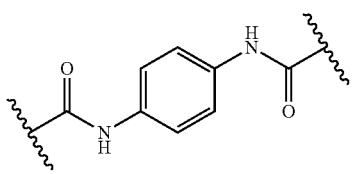

$Z^1$ is O; $Z^2$ is O; each m is independently selected from 1, 2, 3, 4, and 5; and each k is 1.

In some embodiments is a compound of Formula (II) wherein X is

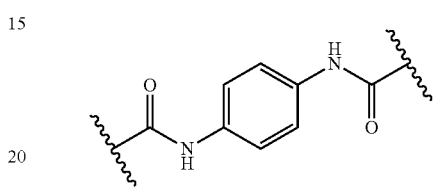

$Z^1$ is O; $Z^2$ is NH; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is

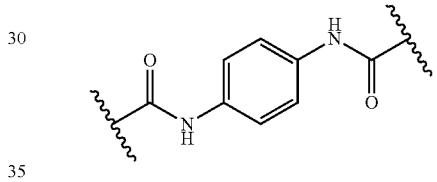

$Z^1$ is O; $Z^2$ is NH; each m is independently selected from 0, 1, 2, 3, 4, 5, and 6; and each k is independently selected from 1, 2, 3, 4, and 5. In some embodiments is a compound of Formula (II) wherein X is

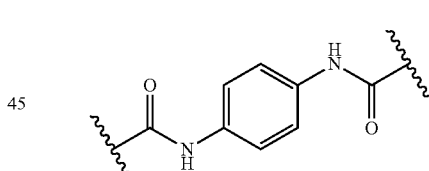

$Z^1$ is O; $Z^2$ is NH; each m is independently selected from 1, 2, 3, 4, and 5; and each k is independently selected from 1, 2, and 3. In some embodiments is a compound of Formula (II) wherein X

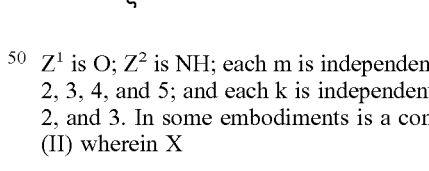

is $Z^1$ is O; $Z^2$ is NH; each m is independently selected from 1, 2, 3, 4, and 5; and each k is 1.

In some embodiments is a compound of Formula (II) wherein X is

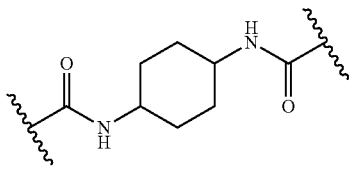

;

$Z^1$ is O; $Z^2$ is O; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is

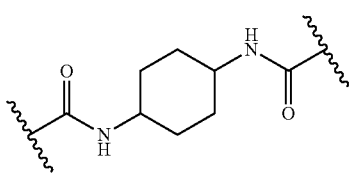

;

$Z^1$ is O; $Z^2$ is O; each m is independently selected from 0, 1, 2, 3, 4, 5, and 6; and each k is independently selected from 1, 2, 3, 4, and 5. In some embodiments is a compound of Formula (II) wherein X is

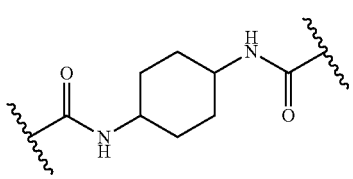

;

$Z^1$ is O; $Z^2$ is O; each m is independently selected from 1, 2, 3, 4, and 5; and each k is independently selected from 1, 2, and 3. In some embodiments is a compound of Formula (II) wherein X is

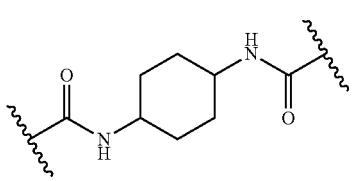

;

$Z^1$ is O; $Z^2$ is O; each m is independently selected from 1, 2, 3, 4, and 5; and each k is 1.

In some embodiments is a compound of Formula (II) wherein X is

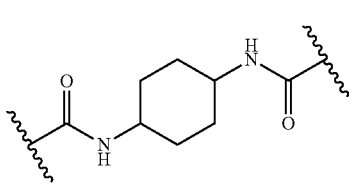

;

$Z^1$ is O; $Z^2$ is NH; each m is independently selected from 0, 1, 2, 3, 4, 5, 6, 7, 8, 9, and 10; and each k is independently selected from 1, 2, 3, 4, 5, 6, 7, 8, 9, and 10. In some embodiments is a compound of Formula (II) wherein X is

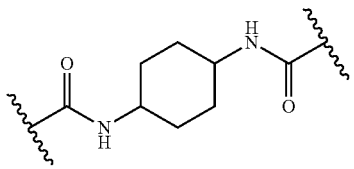

;

$Z^1$ is O; $Z^2$ is NH; each m is independently selected from 0, 1, 2, 3, 4, 5, and 6; and each k is independently selected from 1, 2, 3, 4, and 5. In some embodiments is a compound of Formula (II) wherein X is

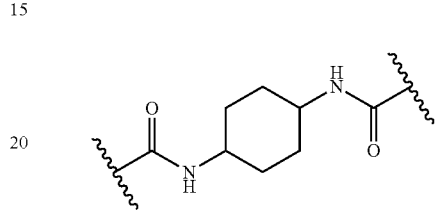

;

$Z^1$ is O; $Z^2$ is NH; each m is independently selected from 1, 2, 3, 4, and 5; and each k is independently selected from 1, 2, and 3. In some embodiments is a compound of Formula (II) wherein X is

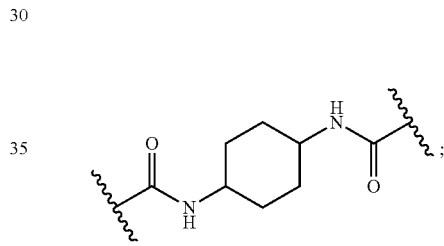

;

$Z^1$ is O; $Z^2$ is NH; each m is independently selected from 1, 2, 3, 4, and 5; and each k is 1.

In a further aspect, provided herein are compounds of Formula (III), or pharmaceutically acceptable salts, solvates, polymorphs, prodrugs, metabolites, deuterides, N-oxides, stereoisomers, or isomers thereof:

$Y^1$-$L^1$-$B^1$-$A^1$-X-$A^2$-$B^2$-$L^2$-$Y^2$     Formula (III), wherein $Y^1$ and $Y^2$ are independently selected from an epithelial sodium channel blocker.

In certain embodiments, provided herein are compounds of Formula (III), or pharmaceutically acceptable salts, solvates, polymorphs, prodrugs, metabolites, deuterides, N-oxides, stereoisomers, or isomers thereof:

$Y^1$-$L^1$-$B^1$-$A^1$-X-$A^2$-$B^2$-$L^2$-$Y^2$     Formula (III);

wherein:

$A^1$ and $A^2$ are independently selected from: a bond, —OCH$_2$—,

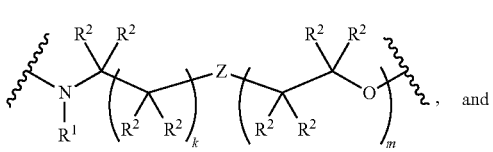, and

-continued

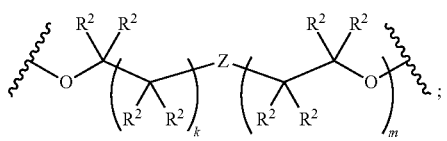

$B^1$ and $B^2$ are independently selected from:

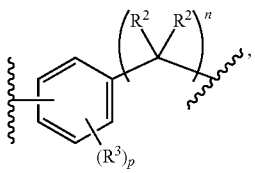

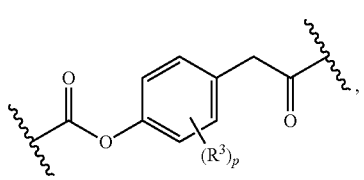

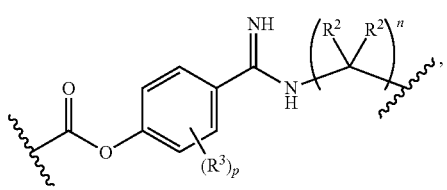

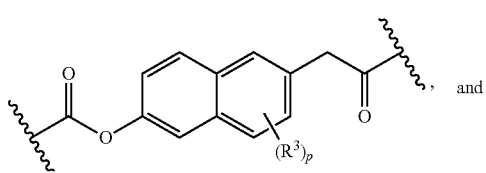

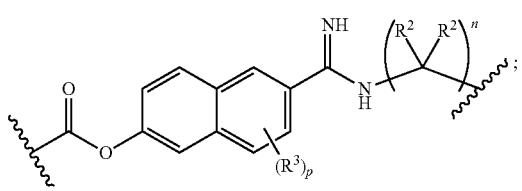

$L^1$ and $L^2$ are independently selected from: a bond,

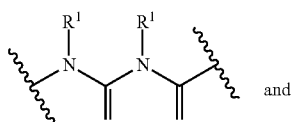

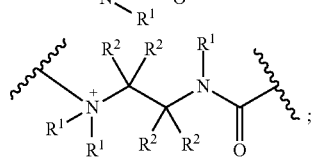

$Y^1$ and $Y^2$ are independently selected from:

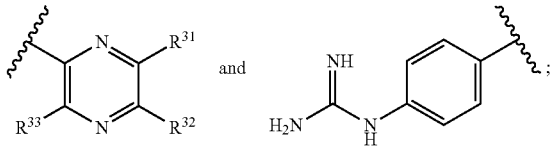

X is a bond, —C(O)—, —C(O)C(O)—,

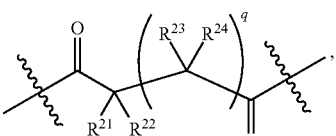

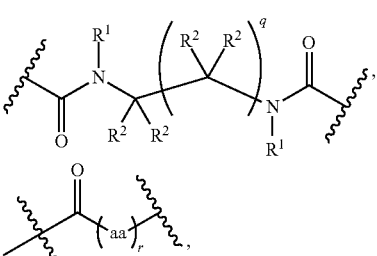

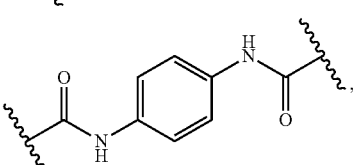

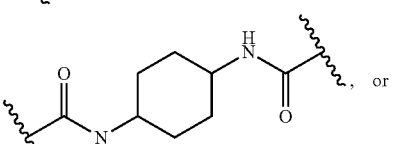

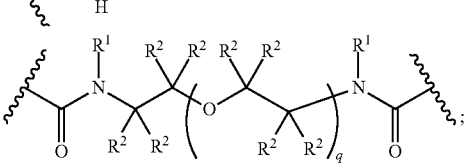

Z is O or $CR^2R^2$;

aa is

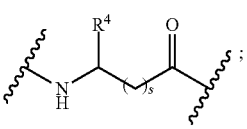

each $R^1$ is independently selected from H, alkyl, haloalkyl, arylalkyl, and heteroarylalkyl;

each $R^2$ is independently selected from H, halo, —CN, —$SR^1$, alkyl, cycloalkyl, haloalkyl, —$OR^1$, —$CO_2R^1$, and -(alkylene)-($CO_2R^1$);

each $R^3$ is independently selected from halo, alkyl, —CN, haloalkyl, —$OR^1$, and —$NR^1R^1$;

each $R^4$ is independently selected from alkyl, $-CO_2R^1$, -(alkylene)-$(CO_2R^1)$, hydroxyalkyl, -(alkylene)$(S(O)_t)$(alkyl), -(alkylene)$(NR^5R^5)$, and

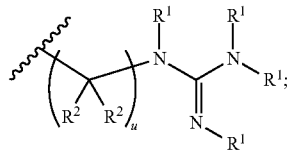

each $R^5$ is independently selected from H, alkyl, haloalkyl, arylalkyl, heteroarylalkyl, aryl, and heteroaryl;

each $R^{21}$, $R^{22}$, $R^{23}$, and $R^{24}$ are independently selected from H, halo, —CN, —$SR^1$, alkyl, cycloalkyl, haloalkyl, —$NR^1R^1$, and —$OR^1$;

$R^{31}$, $R^{32}$, and $R^{33}$ are independently selected from halo, alkyl, —CN, haloalkyl, —$OR^1$, and —$NR^1R^1$;

each k is independently selected from 1, 2, 3, 4, 5, 6, 7, 8, 9, and 10;

each m is independently selected from 0, 1, 2, 3, 4, 5, 6, 7, 8, 9, and 10;

each n is independently selected from 1, 2, 3, 4, 5, 6, 7, 8, 9, and 10;

each p is independently selected from 0, 1, 2, 3, and 4;

q is 1, 2, 3, 4, 5, 6, 7, 8, 9, or 10;

r is 3, 4, 5, 6, or 7;

each s is independently selected from 0, 1, 2, 3, and 4;

each t is independently selected from 0, 1, and 2; and each u is independently selected from 1, 2, 3, 4, 5, 6, 7, 8, 9, and 10.

In some embodiments described above or below of a compound of Formula (III), $Y^1$ and $Y^2$ are the same. In some embodiments described above or below of a compound of Formula (III), $Y^1$ and $Y^2$ are the same and $R^{31}$, $R^{32}$, and $R^{33}$ are independently selected from halo and —$NR^1R^1$. In some embodiments described above or below of a compound of Formula (III), $Y^1$ and $Y^2$ are the same and $R^{31}$, $R^{32}$, and $R^{33}$ are independently selected from halo and —$NH_2$. In some embodiments described above or below of a compound of Formula (III), $Y^1$ and $Y^2$ are both

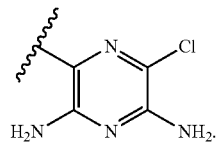

In some embodiments described above or below of a compound of Formula (III), $Y^1$ and $Y^2$ are both

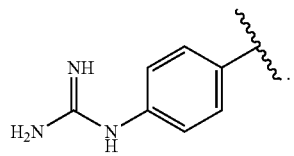 [SMILES: *c1ccc(NC(=N)N)cc1]

In some embodiments described above or below of a compound of Formula (III), $Y^1$ and $Y^2$ are different. In some embodiments described above or below of a compound of Formula (III), $Y^1$ is

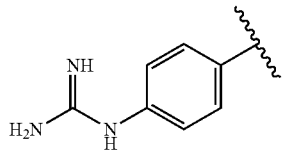 [SMILES: *c1ccc(NC(=N)N)cc1]

and $Y^2$ is

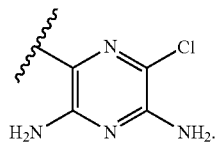

In some embodiments described above or below of a compound of Formula (III), $B^1$ and $B^2$ are the same. In some embodiments described above or below of a compound of Formula (III), $B^1$ and $B^2$ are both

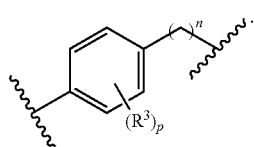

In some embodiments described above or below of a compound of Formula (III), $B^1$ and $B^2$ are both

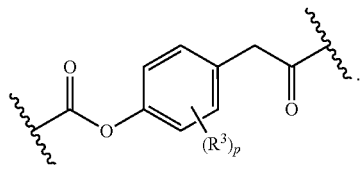

In some embodiments described above or below of a compound of Formula (III), $B^1$ and $B^2$ are both

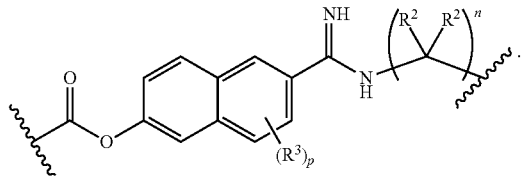

In certain embodiments described above or below of a compound of Formula (III), n is 1, 2, 3, 4, or 5. In certain embodiments described above or below of a compound of Formula (III), n is 2, 3 or 4. In certain embodiments described above or below of a compound of Formula (III), n is 3 or 4. In certain embodiments described above or below of a compound of Formula (III), n is 2. In certain embodiments described above or below of a compound of Formula (III), n is 3. In certain embodiments described above or below of a compound of Formula (III), n is 4. In certain embodiments described above or below of a compound of Formula (III), p is 0. In certain embodiments described above or below of a compound of Formula (III), p is 1.

In some embodiments described above or below of a compound of Formula (III), $B^1$ and $B^2$ are different. In some embodiments described above or below of a compound of Formula (III), $B^1$ is

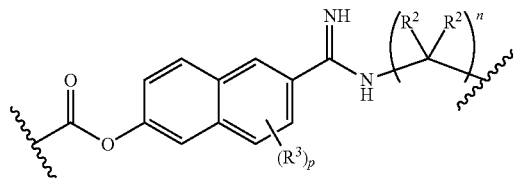

and $B^2$ is

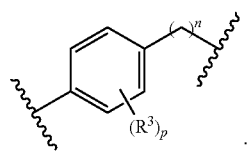

In some embodiments described above or below of a compound of Formula (III), $A^1$ and $A^2$ are the same. In some embodiments described above or below of a compound of Formula (III), $A^1$ and $A^2$ are both a bond. In some embodiments described above or below of a compound of Formula (III), $A^1$ and $A^2$ are both —$OCH_2$—. In some embodiments described above or below of a compound of Formula (III), $A^1$ and $A^2$ are both

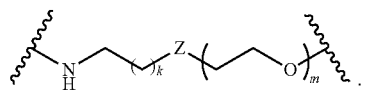

In some embodiments described above or below of a compound of Formula (III), $A^1$ and $A^2$ are both

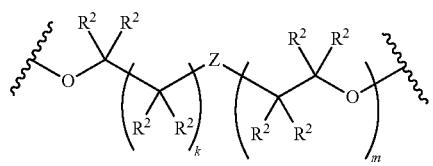

In some embodiments described above or below of a compound of Formula (III), $A^1$ and $A^2$ are different. In some embodiments described above or below of a compound of Formula (III), $A^1$ is a bond and $A^2$ is

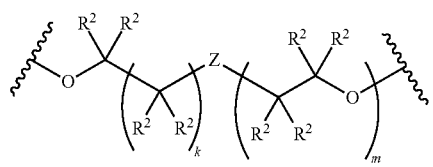

In some embodiments described above or below of a compound of Formula (III), Z is O. In certain embodiments described above or below of a compound of Formula (III), each k is independently 1, 2, or 3. In certain embodiments described above or below of a compound of Formula (III), each k is 1. In certain embodiments described above or below of a compound of Formula (III), each m is independently 0, 1, 2, or 3. In certain embodiments described above or below of a compound of Formula (III), each m is 0. In certain embodiments described above or below of a compound of Formula (III), each m is 1. In certain embodiments described above or below of a compound of Formula (III), each m is 2. In certain embodiments described above or below of a compound of Formula (III), each m is 3.

In some embodiments described above or below of a compound of Formula (III), Z is $CR^2R^2$.

In some embodiments described above or below of a compound of Formula (III), $L^1$ and $L^2$ are the same.

In some embodiments described above or below of a compound of Formula (III), $L^1$ and $L^2$ are both a bond. In some embodiments described above or below of a compound of Formula (III), $L^1$ and $L^2$ are both

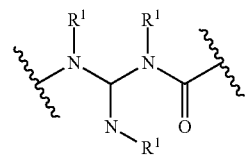

In certain embodiments described above or below of a compound of Formula (III), $L^1$ and $L^2$ are both

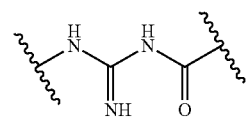

In some embodiments described above or below of a compound of Formula (III), $L^1$ and $L^2$ are different. In some embodiments described above or below of a compound of Formula (III), $L^1$ is a bond and $L^2$ is

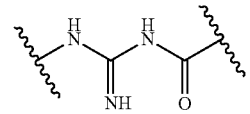

In some embodiments described above or below of a compound of Formula (III), X is —C(O)—. In some embodiments described above or below of a compound of Formula (III), X is —C(O)C(O)—.

In some embodiments described above or below of a compound of Formula (III), X is a bond. In some embodiments described above or below of a compound of Formula (III), X is

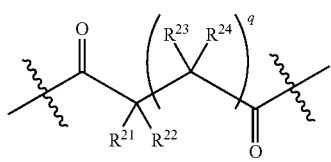

In some embodiments described above or below of a compound of Formula (III), $R^{21}$ and $R^{23}$ are the same and $R^{22}$ and $R^{24}$ are the same. In certain embodiments described above or below of a compound of Formula (III), X is

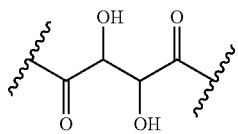

In some embodiments described above or below of a compound of Formula (III), $R^{21}$ and $R^{22}$ are the same. In some embodiments described above or below of a compound of Formula (III), $R^{23}$ and $R^{24}$ are the same. In some embodiments described above or below of a compound of Formula (III), $R^{21}$, $R^{22}$, $R^{23}$, and $R^{24}$ are the same. In some embodiments described above or below of a compound of Formula (III), $R^{21}$, $R^{22}$, $R^{23}$, $R^{24}$ and R are each hydrogen. In certain embodiments described above or below of a compound of Formula (III), X is

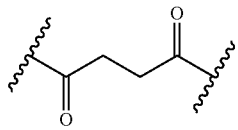

In some embodiments described above or below of a compound of Formula (III), X is

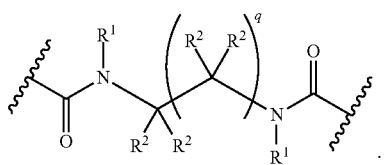

In certain embodiments described above or below of a compound of Formula (III), X is

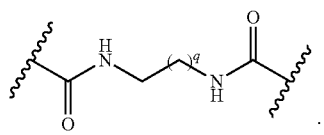

In certain embodiments described above or below of a compound of Formula (III), q is 2, 3, 4, or 5. In certain embodiments described above or below of a compound of Formula (III), q is 3.

In some embodiments described above or below of a compound of Formula (III), X is

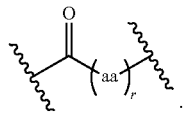

In certain embodiments described above or below of a compound of Formula (III), aa is selected from:

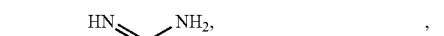

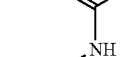

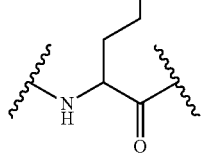 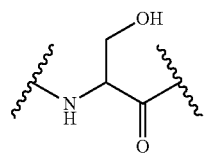

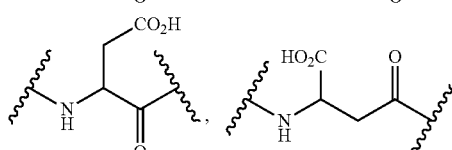

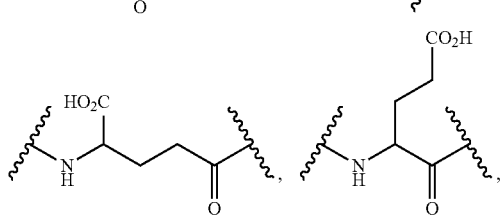

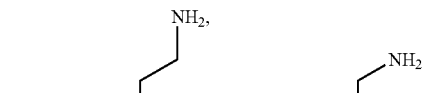

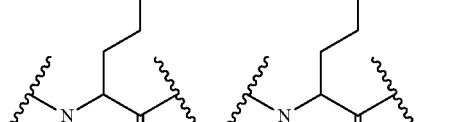

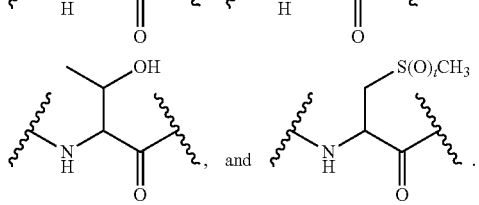

In some embodiments described above or below of a compound of Formula (III), r is 4, 5, or 6.

In some embodiments described above or below of a compound of Formula (III), X is

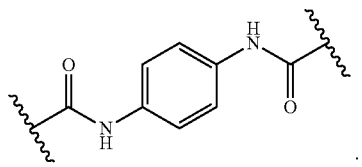 [SMILES: *C(=O)Nc1ccc(NC(*)=O)cc1]

In some embodiments described above or below of a compound of Formula (III), X is

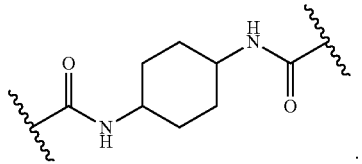 [SMILES: *C(=O)NC1CCC(NC(*)=O)CC1]

In some embodiments described above or below of a compound of Formula (III), X is

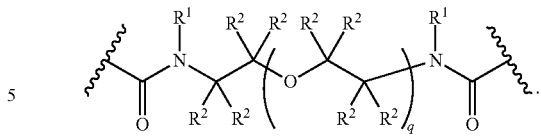

In some embodiments described above or below of a compound of Formula (III), X is

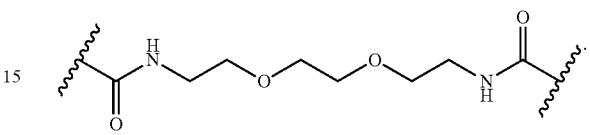

In one aspect, provided herein are compounds, or pharmaceutically acceptable salts, solvates, polymorphs, prodrugs, metabolites, N-oxides, stereoisomers, or isomers thereof, selected from:

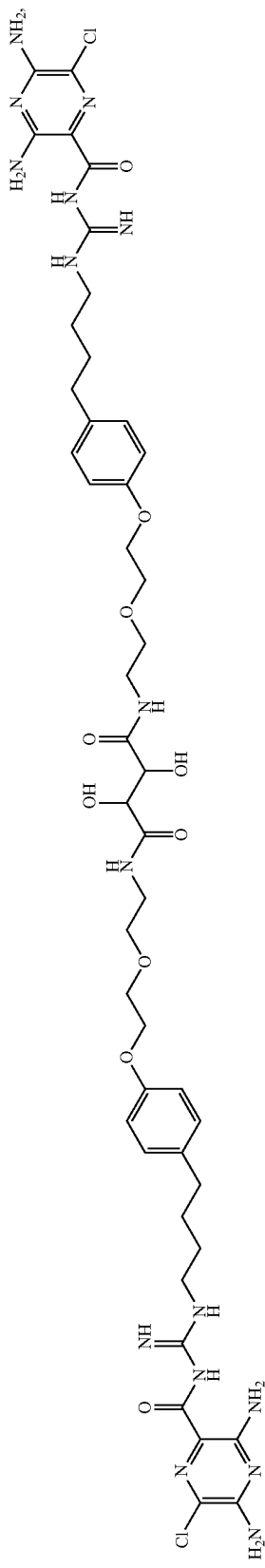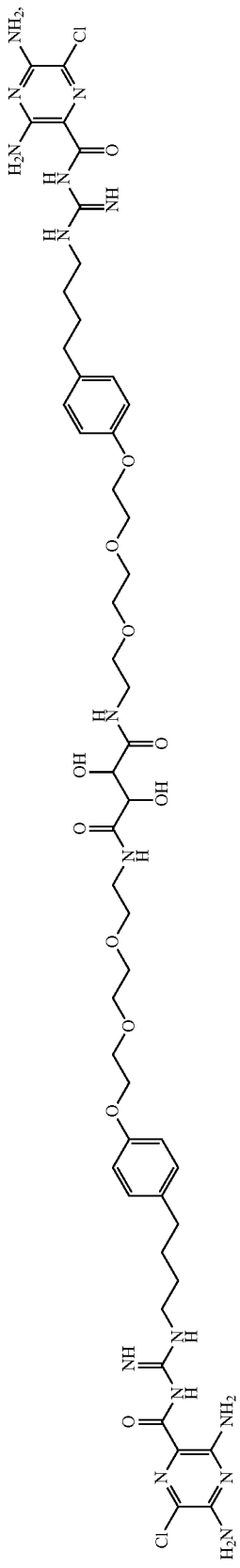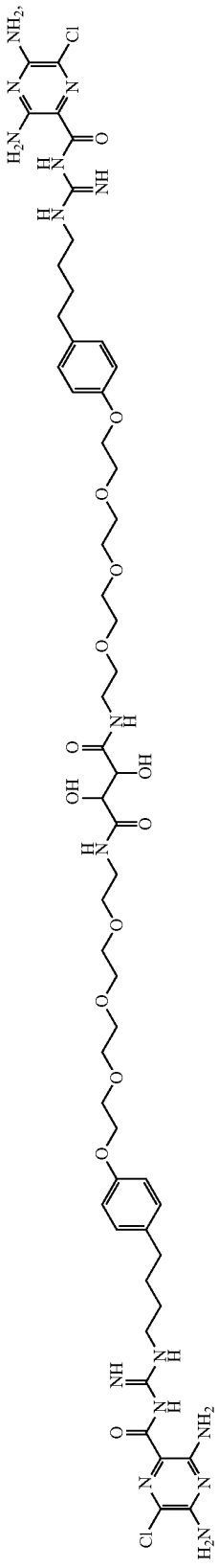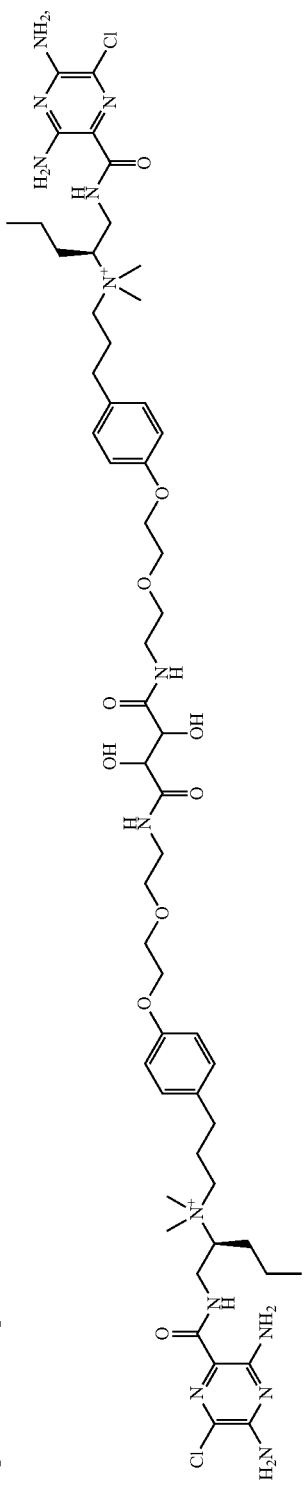

-continued
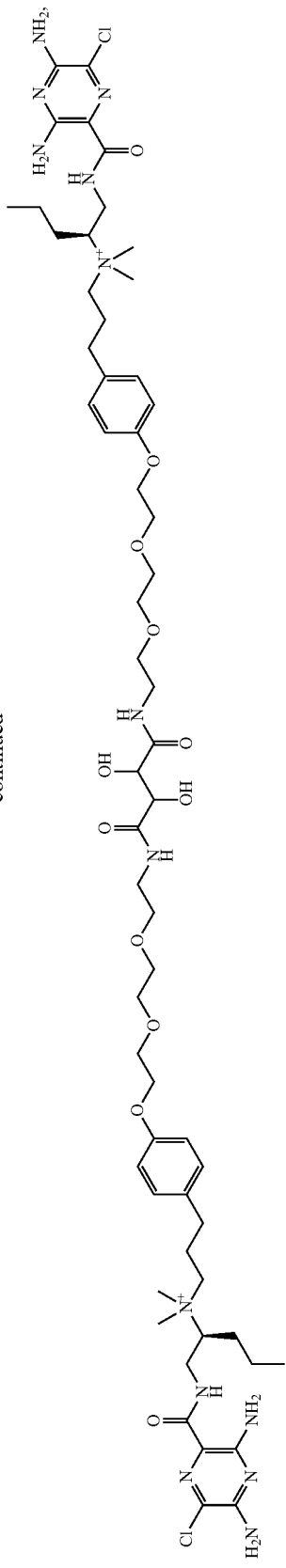
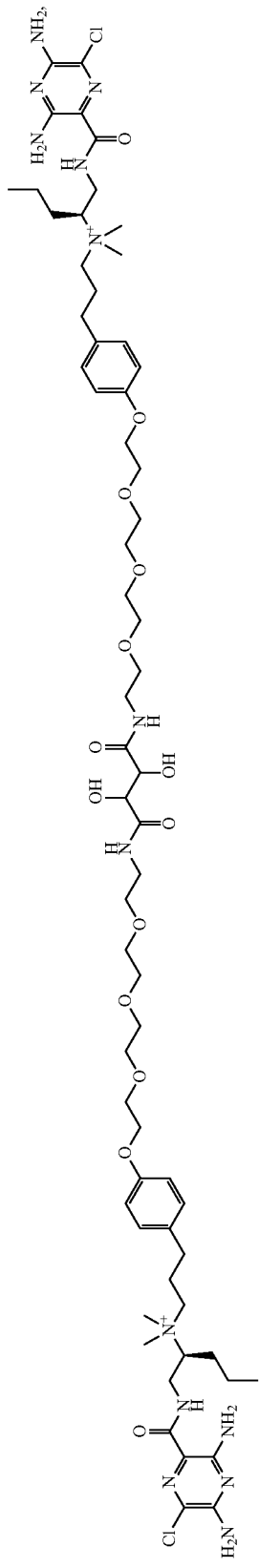
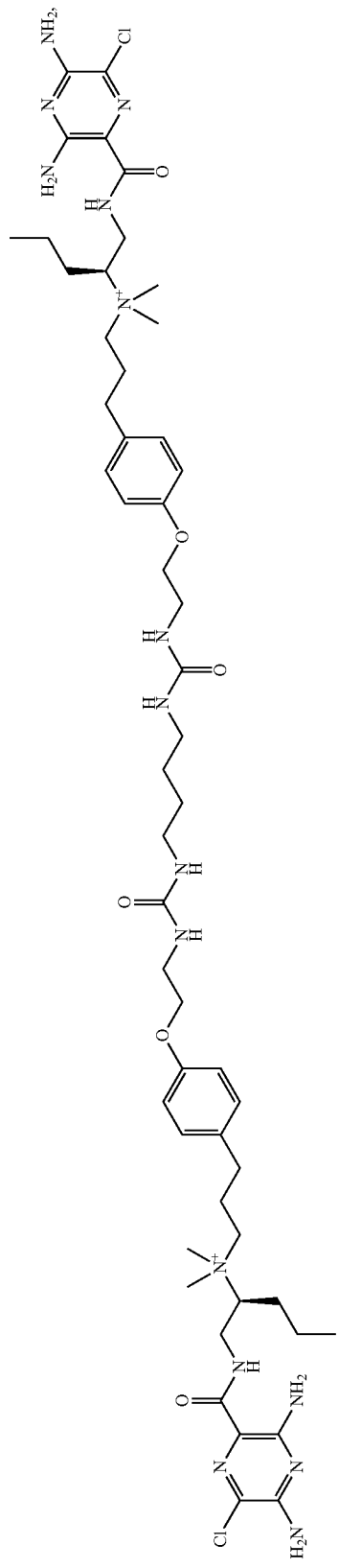

-continued
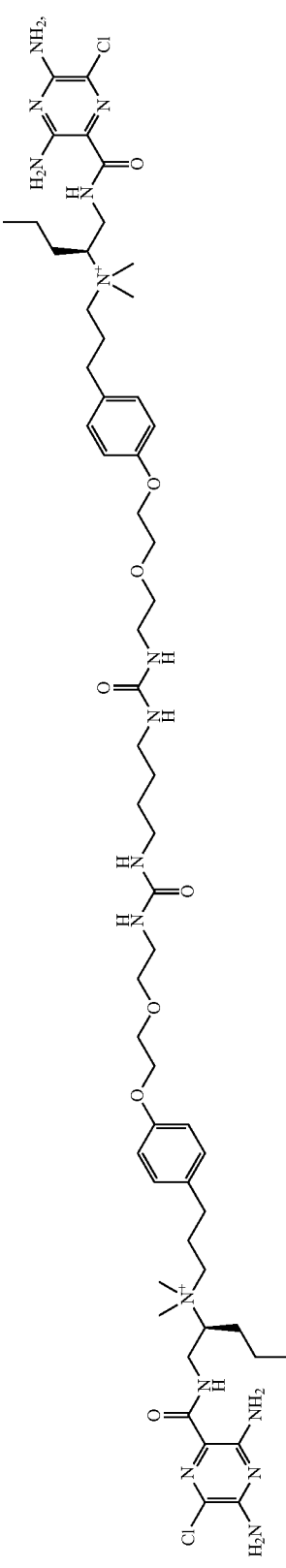
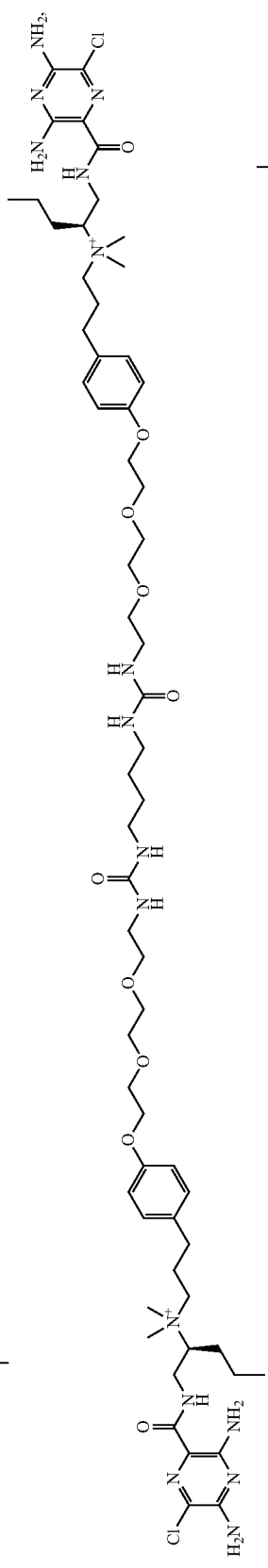
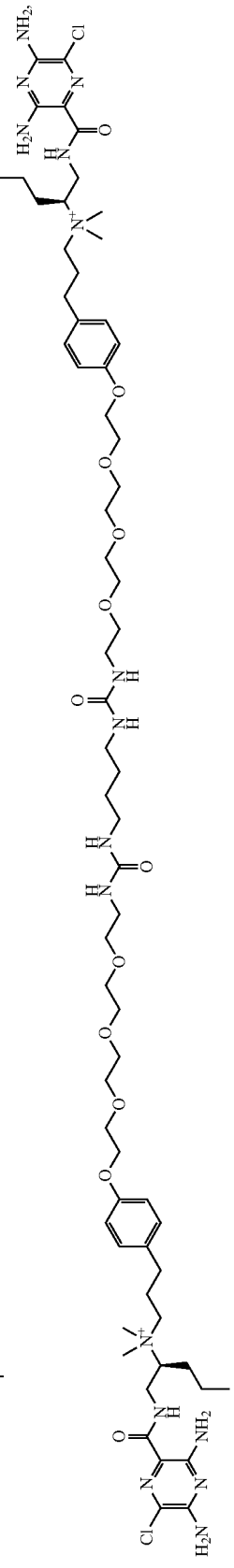
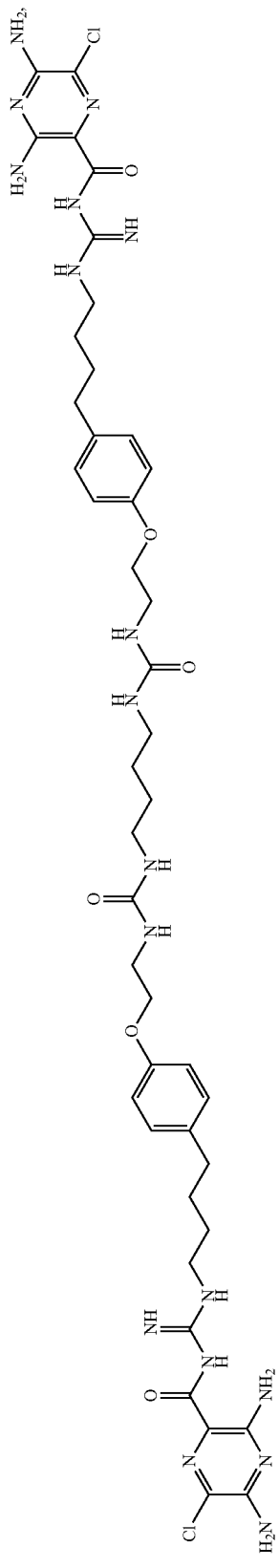

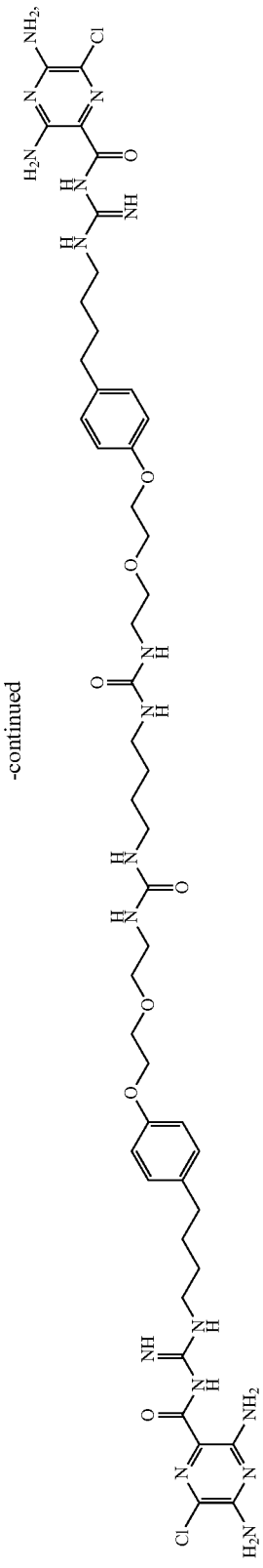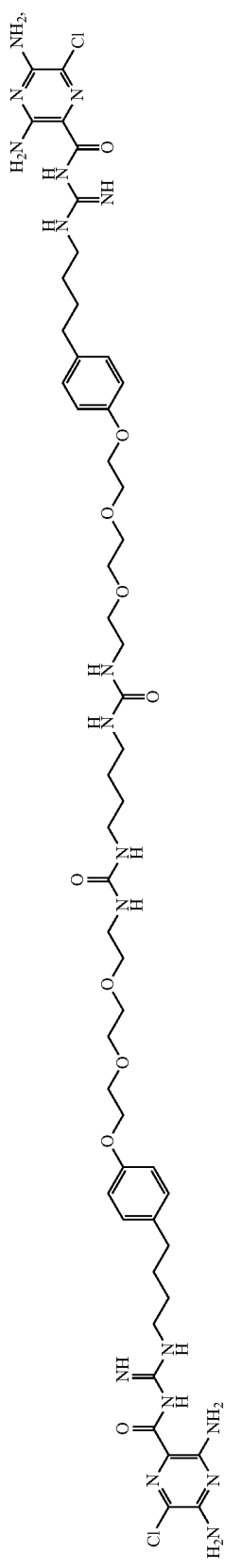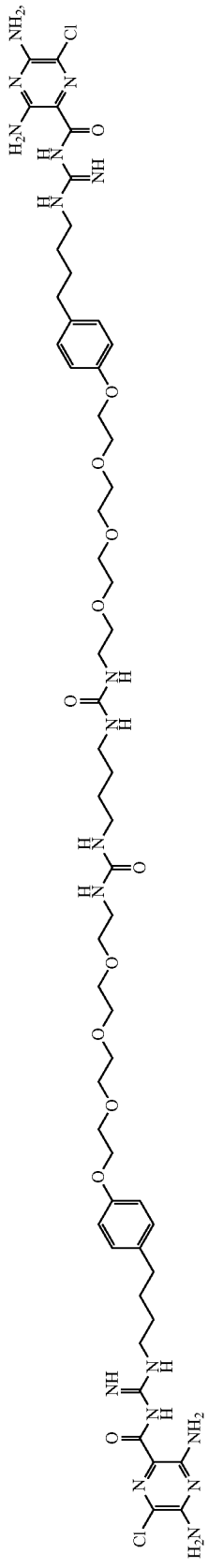

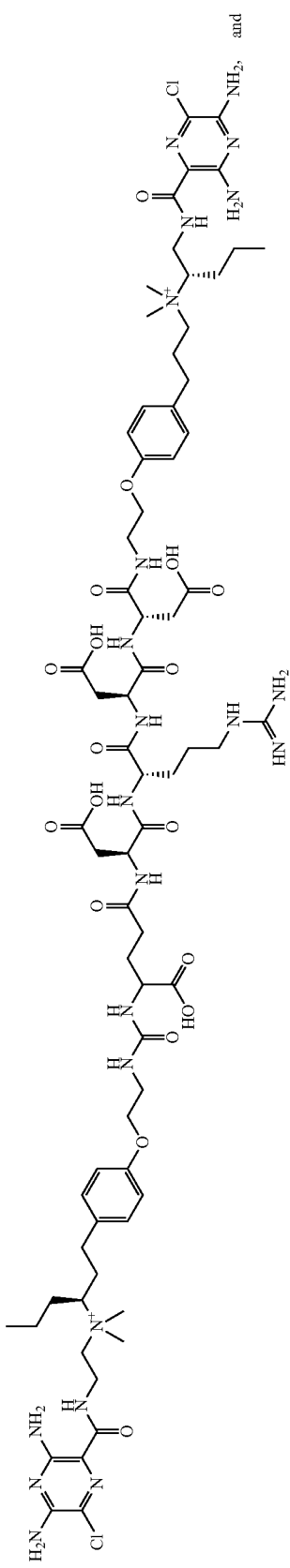
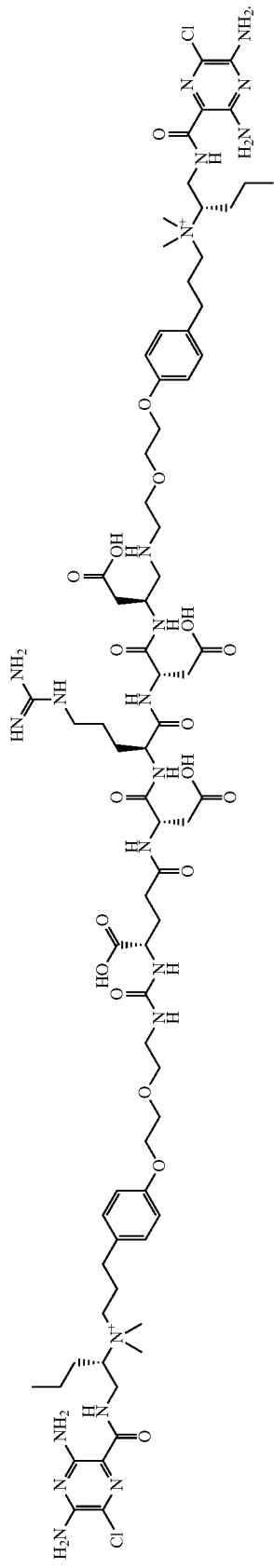

In another aspect, provided herein are compounds, or pharmaceutically acceptable salts, solvates, polymorphs, prodrugs, metabolites, N-oxides, stereoisomers, or isomers thereof, selected from:

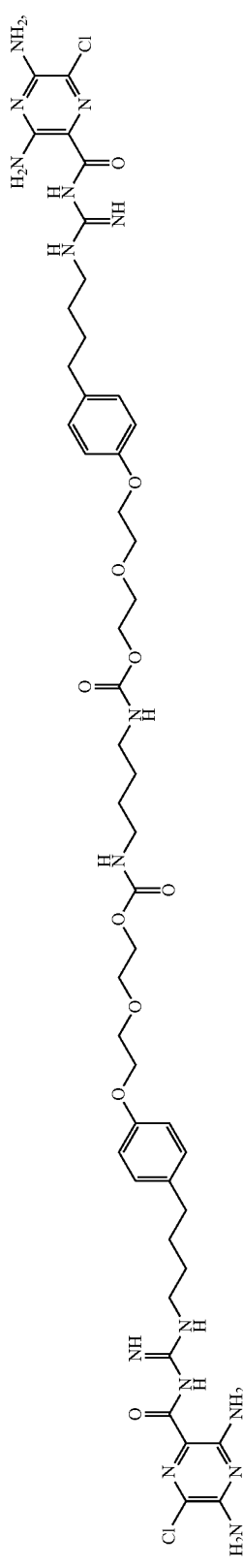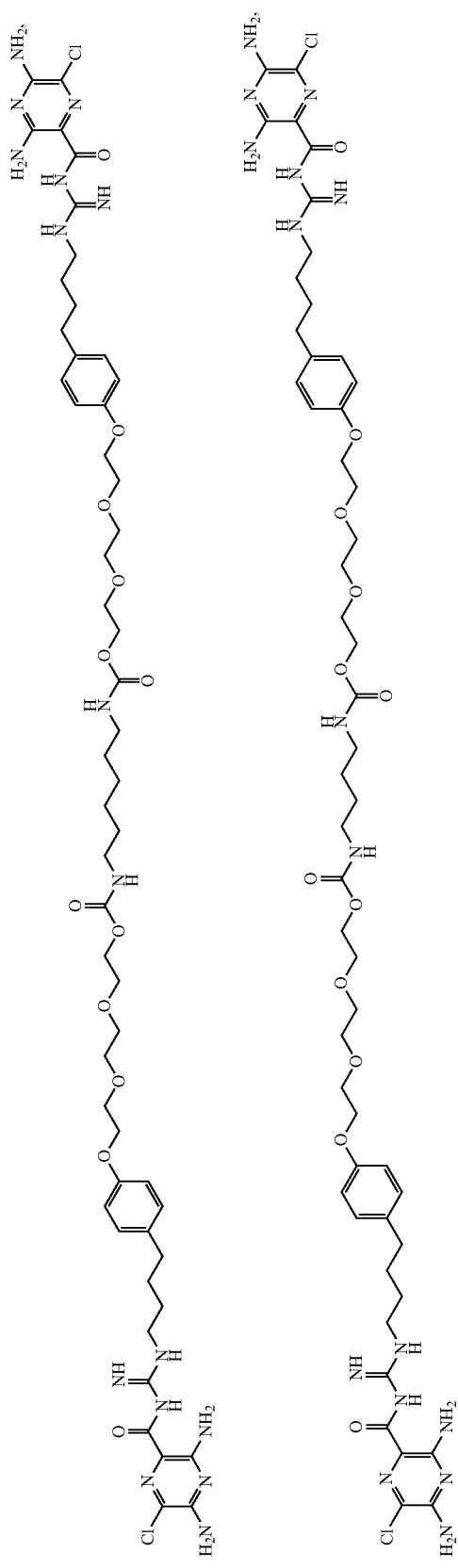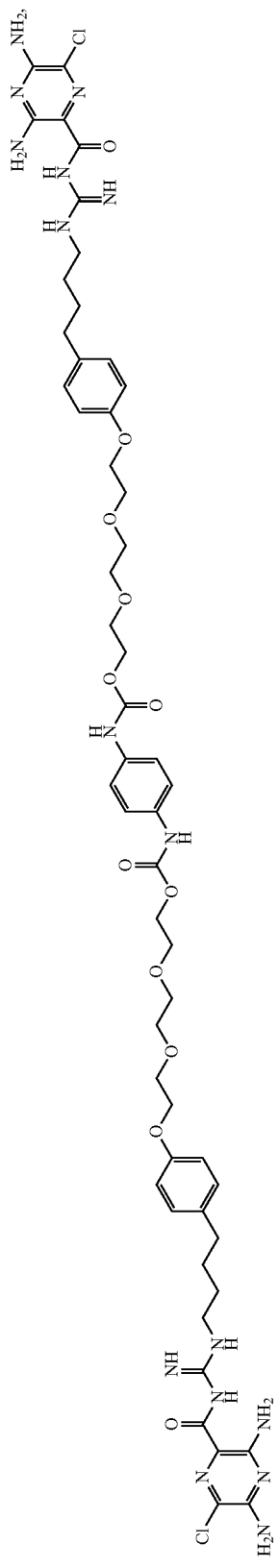

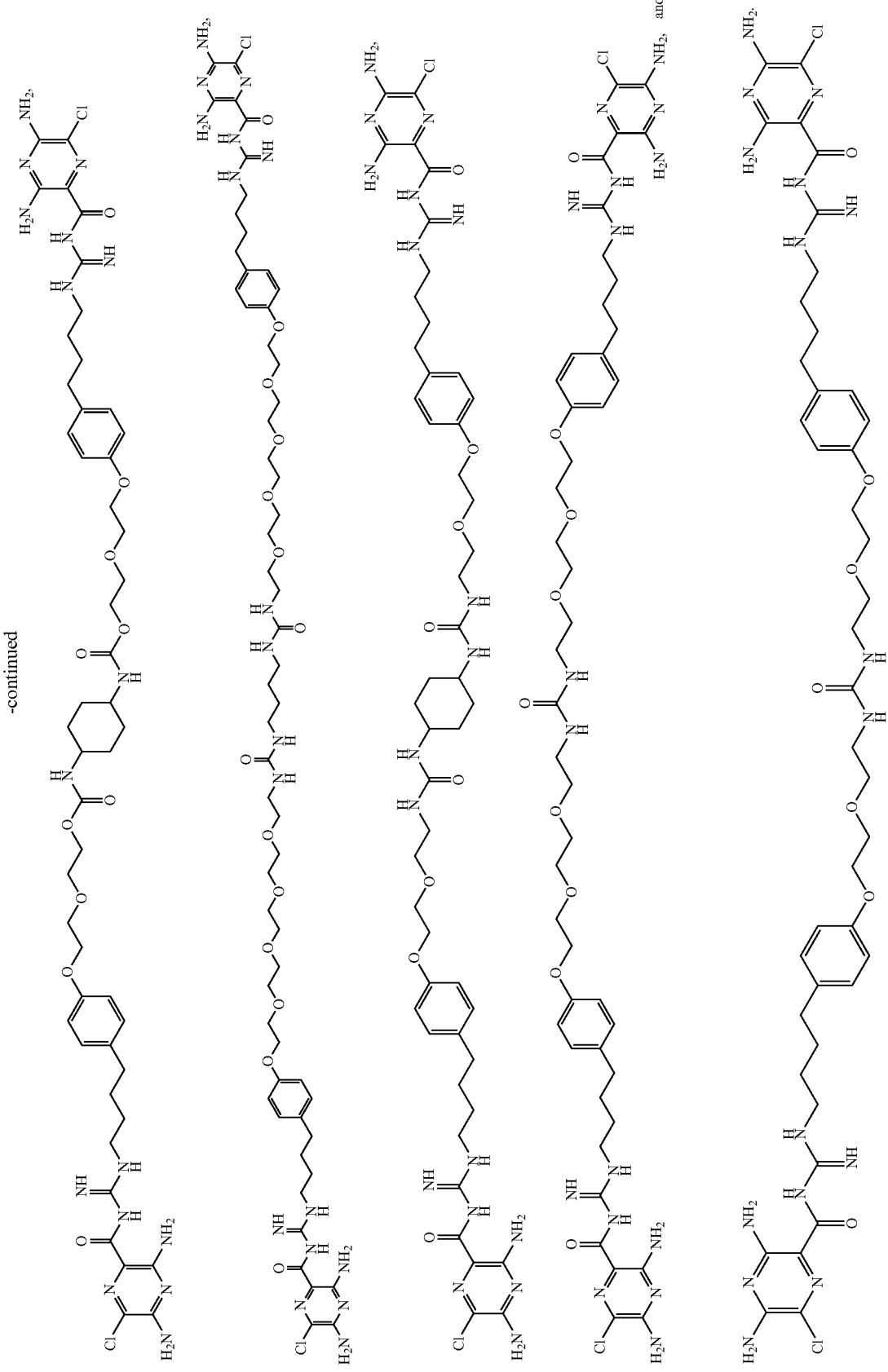

In another aspect, provided herein are compounds, or pharmaceutically acceptable salts, solvates, polymorphs, prodrugs, metabolites, N-oxides, stereoisomers, or isomers thereof, selected from:

91
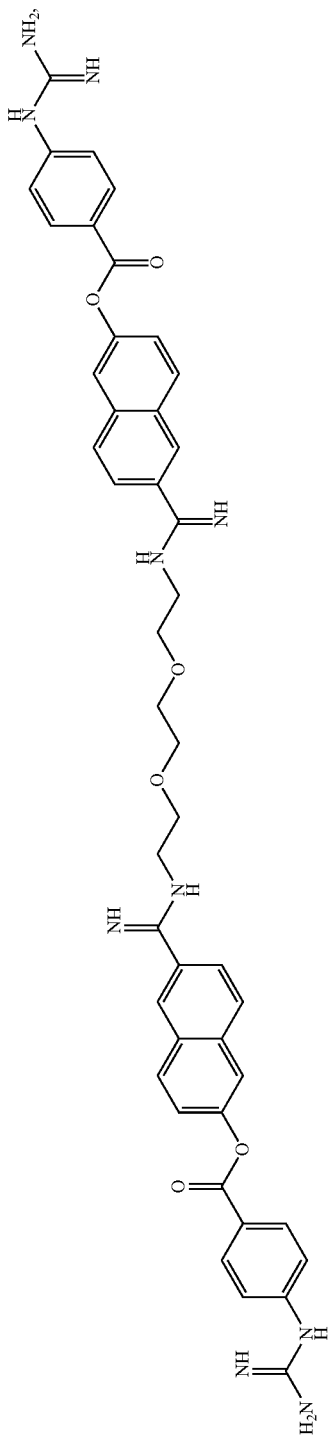
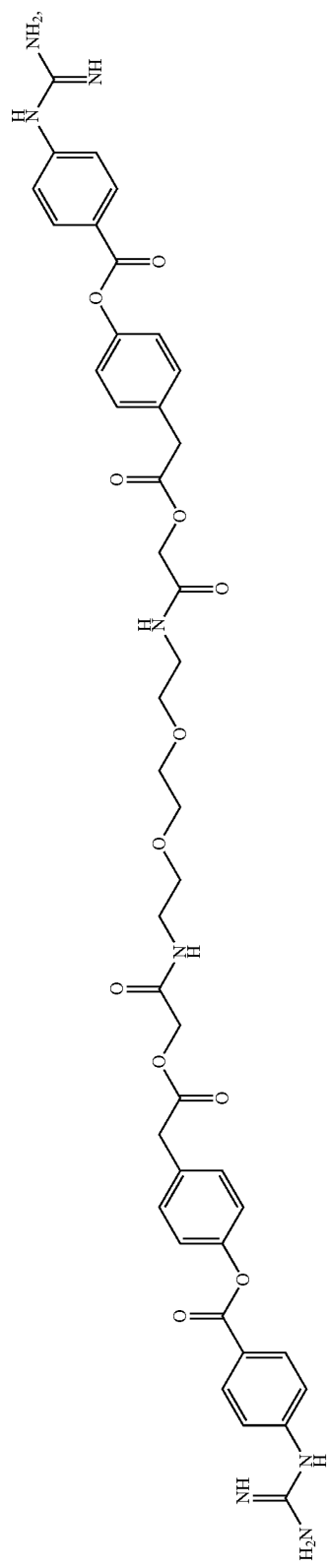
92
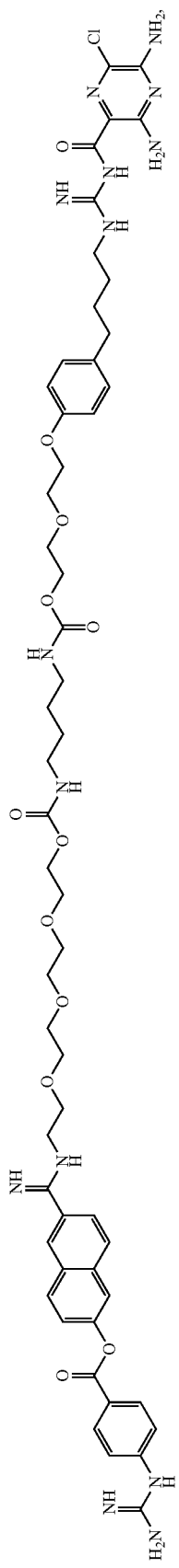

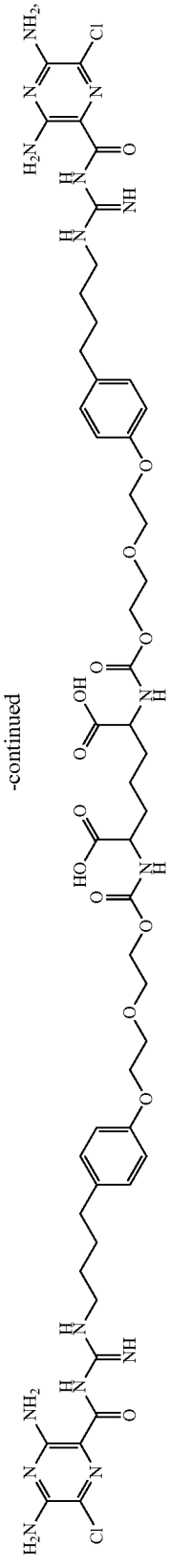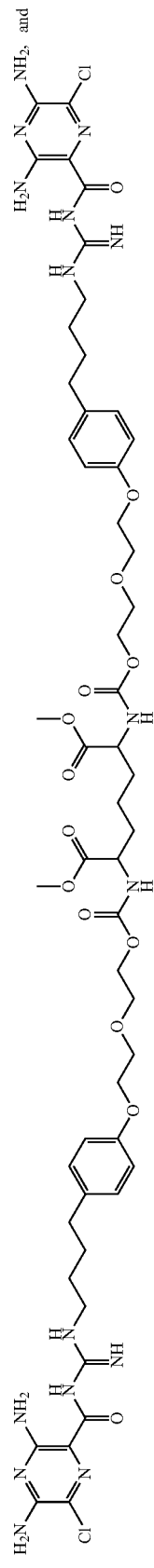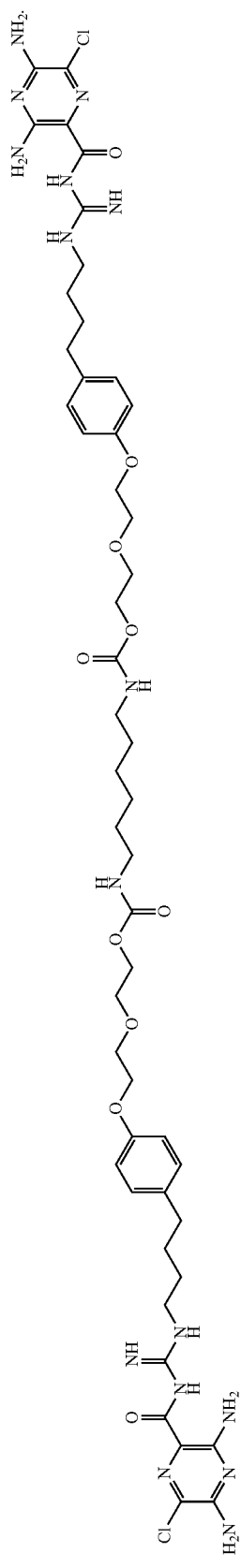

In another aspect, provided herein is a compound, or pharmaceutically acceptable salt, solvate, polymorph, prodrug, metabolite, N-oxide, stereoisomer, or isomer thereof, having the structure:

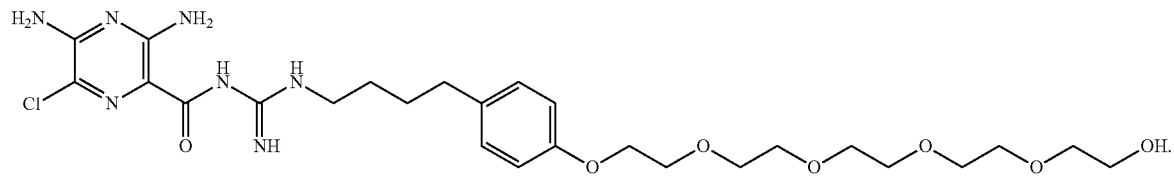 [SMILES: N=C(NCCCCc1ccc(OCCOCCOCCOCCOCCO)cc1)NC(=O)c1nc(Cl)c(N)nc1N]

In another aspect, provided herein are compounds of Formula (IV), or pharmaceutically acceptable salts, solvates, polymorphs, prodrugs, metabolites, deuterides, N-oxides, stereoisomers, or isomers thereof:

$Y^1$—$B^1$-$A^1$-X-$A^2$-$B^2$—$Y^2$  Formula (IV);

wherein:
each $Y^1$ and $Y^2$ is an epithelial sodium channel blocker;
each $A^1$ and $A^2$ is independently selected from a bond and a hydrophilic linker;
each $B^1$ and $B^2$ is a hydrophobic linker; and
X is a bond, hydrophobic linker, or hydrophilic linker.

In some embodiments is a compound of Formula (IV), wherein
each $A^1$ and $A^2$ is independently selected from: a bond, —OCH$_2$—,

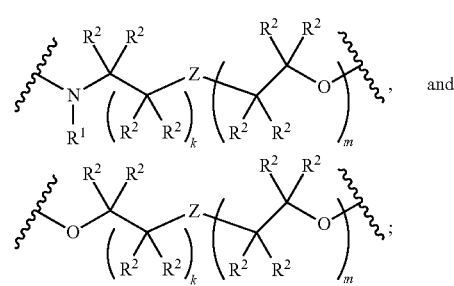

each $B^1$ and $B^2$ is independently selected from:

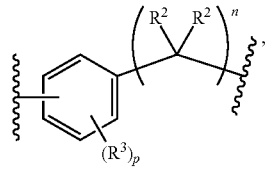

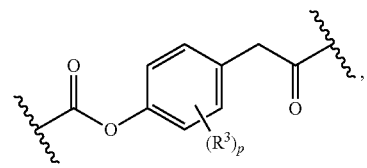

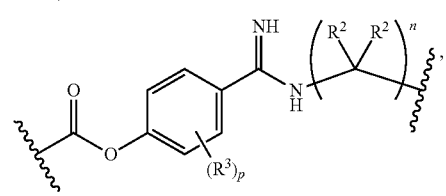

-continued

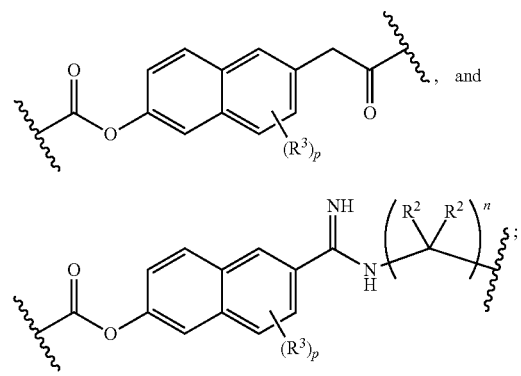

$Y^1$ and $Y^2$ are independently selected from:

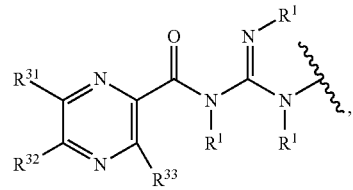

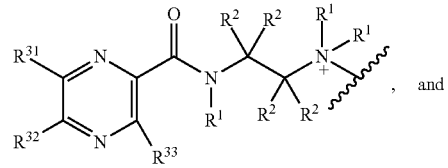

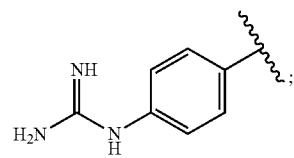

X is a bond, —C(O)—, —C(O)C(O)—,

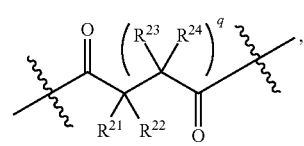

-continued

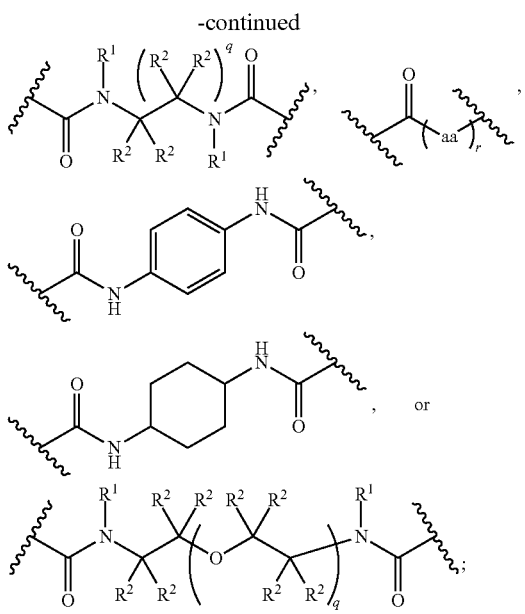

Z is O or $CR^2R^2$;
aa is

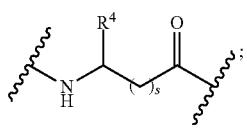

each $R^1$ is independently selected from H, alkyl, haloalkyl, arylalkyl, and heteroarylalkyl;
each $R^2$ is independently selected from H, halo, —CN, —$SR^1$, alkyl, cycloalkyl, haloalkyl, —$OR^1$, —$CO_2R^1$, and -(alkylene)-($CO_2R^1$);
each $R^3$ is independently selected from halo, alkyl, —CN, haloalkyl, —$OR^1$, and —$NR^1R^1$;
each $R^4$ is independently selected from alkyl, —$CO_2R^1$, -(alkylene)-($CO_2R^1$), hydroxyalkyl, -(alkylene)(S(O)$_t$)(alkyl), -(alkylene)($NR^5R^5$), and

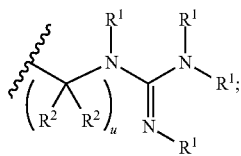

each $R^5$ is independently selected from H, alkyl, haloalkyl, arylalkyl, heteroarylalkyl, aryl, and heteroaryl;
each $R^{21}$, $R^{22}$, $R^{23}$, and $R^{24}$ are independently selected from H, halo, —CN, —$SR^1$, alkyl, cycloalkyl, haloalkyl, —$NR^1R^1$, and —$OR^1$;
$R^{31}$, $R^{32}$, and $R^{33}$ are independently selected from halo, alkyl, —CN, haloalkyl, —$OR^1$, and —$NR^1R^1$;
each k is independently selected from 1, 2, 3, 4, 5, 6, 7, 8, 9, and 10;
each m is independently selected from 0, 1, 2, 3, 4, 5, 6, 7, 8, 9, and 10;
each n is independently selected from 1, 2, 3, 4, 5, 6, 7, 8, 9, and 10;
each p is independently selected from 0, 1, 2, 3, and 4;
q is 1, 2, 3, 4, 5, 6, 7, 8, 9, or 10;
r is 3, 4, 5, 6, or 7;
each s is independently selected from 0, 1, 2, 3, and 4;
each t is independently selected from 0, 1, and 2; and
each u is independently selected from 1, 2, 3, 4, 5, 6, 7, 8, 9, and 10.

In another aspect, provided herein is a method to treat a lung disease, the method comprising administering a composition comprising a compound of Formula (IV):

$$Y^1-B^1-A^1-X-A^2-B^2-Y^2 \qquad \text{Formula (IV);}$$

wherein:
each $Y^1$ and $Y^2$ is a biologically active moiety;
each $A^1$ and $A^2$ is independently selected from a bond and a hydrophilic linker;
each $B^1$ and $B^2$ is a hydrophobic linker; and
X is a bond, hydrophobic linker, or hydrophilic linker.

In some embodiments is a method to treat a lung disease, the method comprising administering a composition comprising a compound of Formula (IV), wherein each $Y^1$ and $Y^2$ is an epithelial sodium channel blocker.

In some embodiments is a method to treat a lung disease, the method comprising administering a composition comprising a compound of Formula (IV), wherein
each $A^1$ and $A^2$ is independently selected from: a bond, —$OCH_2$—,

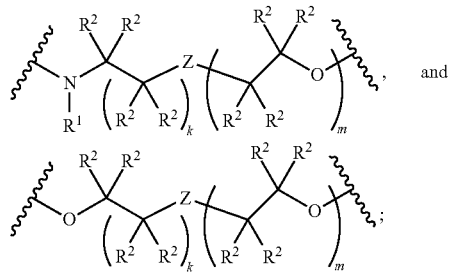

each $B^1$ and $B^2$ is independently selected from:

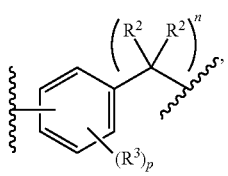

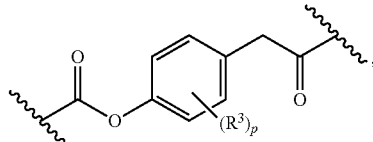

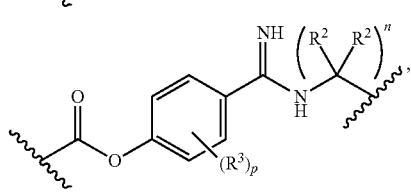

-continued

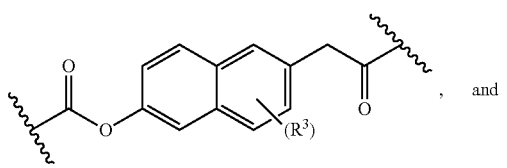

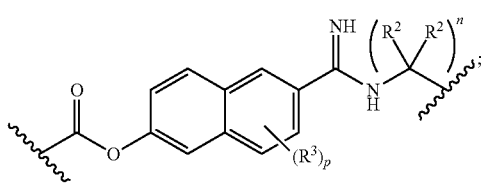

$Y^1$ and $Y^2$ are independently selected from:

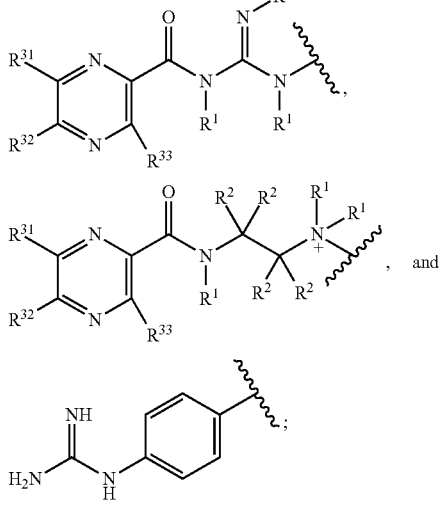

X is a bond, —C(O)—, —C(O)C(O)—,

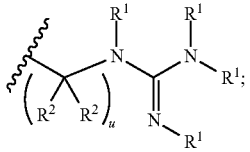

Z is O or $CR^2R^2$;

aa is

- each $R^1$ is independently selected from H, alkyl, haloalkyl, arylalkyl, and heteroarylalkyl;
- each $R^2$ is independently selected from H, halo, —CN, —$SR^1$, alkyl, cycloalkyl, haloalkyl, —$OR^1$, —$CO_2R^1$, and -(alkylene)-($CO_2R^1$);
- each $R^3$ is independently selected from halo, alkyl, —CN, haloalkyl, —$OR^1$, and —$NR^1R^1$;
- each $R^4$ is independently selected from alkyl, —$CO_2R^1$, -(alkylene)-($CO_2R^1$), hydroxyalkyl, -(alkylene)(S(O)$_t$)(alkyl), -(alkylene)($NR^5R^5$), and

- each $R^5$ is independently selected from H, alkyl, haloalkyl, arylalkyl, heteroarylalkyl, aryl, and heteroaryl;
- each $R^{21}$, $R^{22}$, $R^{23}$, and $R^{24}$ are independently selected from H, halo, —CN, —$SR^1$, alkyl, cycloalkyl, haloalkyl, —$NR^1R^1$, and —$OR^1$;
- $R^{31}$, $R^{32}$, and $R^{33}$ are independently selected from halo, alkyl, —CN, haloalkyl, —$OR^1$, and —$NR^1R^1$;
- each k is independently selected from 1, 2, 3, 4, 5, 6, 7, 8, 9, and 10;
- each m is independently selected from 0, 1, 2, 3, 4, 5, 6, 7, 8, 9, and 10;
- each n is independently selected from 1, 2, 3, 4, 5, 6, 7, 8, 9, and 10;
- each p is independently selected from 0, 1, 2, 3, and 4;
- q is 1, 2, 3, 4, 5, 6, 7, 8, 9, or 10;
- r is 3, 4, 5, 6, or 7;
- each s is independently selected from 0, 1, 2, 3, and 4;
- each t is independently selected from 0, 1, and 2; and
- each u is independently selected from 1, 2, 3, 4, 5, 6, 7, 8, 9, and 10.

In some embodiments is a method to treat a lung disease, the method comprising administering a composition comprising a compound of Formula (IV), wherein $Y^1$ and $Y^2$ are the same. In some embodiments is a method to treat a lung disease, the method comprising administering a composition comprising a compound of Formula (IV), wherein $Y^1$ and $Y^2$ are both

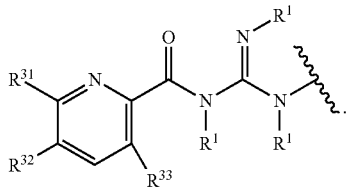

In some embodiments is a method to treat a lung disease, the method comprising administering a composition comprising a compound of Formula (IV), wherein $B^1$ and $B^2$ are both

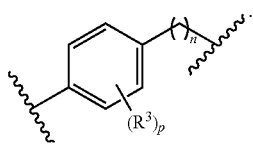

In some embodiments is a method to treat a lung disease, the method comprising administering a composition comprising a compound of Formula (IV), wherein $A^1$ and $A^2$ are both

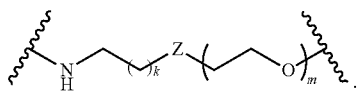

In some embodiments is a method to treat a lung disease, the method comprising administering a composition comprising a compound of Formula (IV), wherein $A^1$ and $A^2$ are both

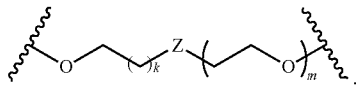

In some embodiments is a method to treat a lung disease, the method comprising administering a composition comprising a compound of Formula (IV), wherein X is

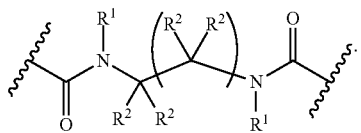

In some embodiments is a method to treat a lung disease, the method comprising administering a composition comprising a compound of Formula (IV), wherein the polar surface area of the compound of Formula (IV) is greater than 350 Å$^2$.

In a certain embodiment, a compound of Formula (I), (Ia), (Ib), (II), (III), or (IV) is provided having a polar surface area of at least 350 Å$^2$ and a molecular weight of at least 800 Dalton. In certain embodiments, the compound of Formula (I), (Ia), (Ib), (II), (III), or (IV) has a molecular weight of at least 750 Da, at least 900 Da, at least 1000 Da, at least 1100 Da, at least 1200 Da, at least 1300 Da, at least 1400 Da, or at least 1500 Da. In further embodiments, the compound of Formula (I), (Ia), (Ib), (II), (III), or (IV) exhibits a polar surface area of at least 250 Å$^2$, at least 300 Å$^2$, at least 350 Å$^2$, at least 400 Å$^2$, at least 450 Å$^2$, or at least 500 Å$^2$. In further embodiments, the compound is substantially active on the apical side of the epithelium of the lung to locally block ENaC.

In some embodiments, a dimeric compound of Formula (I), (Ia), (Ib), (II), (III), or (IV) achieves a systemic Cmax of less than 100 pg/mL and an AUC of less than 100 h*pg/mL after delivery by inhalation. In certain embodiments, a dimeric compound of Formula (I), (Ia), (Ib), (II), (III), or (IV) achieves a systemic Cmax of less than 1000 pg/mL, less than 900 pg/mL, less than 800 pg/mL, less than 700 pg/mL, less than 600 pg/mL, less than 500 pg/mL, less than 400 pg/mL, less than 300 pg/mL, less than 200 pg/mL, less than 100 pg/mL, less than 75 pg/mL, less than 50 pg/mL, or less than 25 pg/mL after delivery by inhalation. In preferred embodiments, a dimeric compound of Formula (I), (Ia), (Ib), (II), (III), or (IV) achieves a systemic Cmax of less than 100 pg/mL after delivery by inhalation. In some embodiments, a dimeric compound of Formula (I), (Ia), (Ib), (II), (III), or (IV) achieves a systemic (plasma) AUC of less than 250 h*pg/mL, less than 200 h*pg/mL, less than 150 h*pg/mL, less than 125 h*pg/mL, less than 100 h*pg/mL, less than 90 h*pg/mL, less than 80 h*pg/mL, less than 70 h*pg/mL, less than 60 h*pg/mL, less than 50 h*pg/mL, less than 40 h*pg/mL, less than 30 h*pg/mL, less than 25 h*pg/mL, less than 20 h*pg/mL, less than 15 h*pg/mL, or less than 10 h*pg/mL after delivery by inhalation. In preferred embodiments, a dimeric compound of Formula (I), (Ia), (Ib), (II), (III), or (IV) achieves a systemic (plasma) AUC of less than 100 h*pg/mL after delivery by inhalation.

Preparation of Compounds

Described herein are compounds of Formula (I), (Ia), (Ib), (II), (III), or (IV) that treat cystic fibrosis, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Also described herein are compounds of Formula (I), (Ia), (Ib), (II), (III), or (IV) that treat chronic obstructive pulmonary disease, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula (I), (Ia), (Ib), (II), (III), or (IV) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989); (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S confirguration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In certain embodiments, the compounds described herein exist as partially or fully deuterated forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

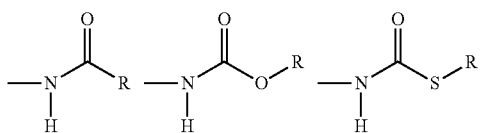

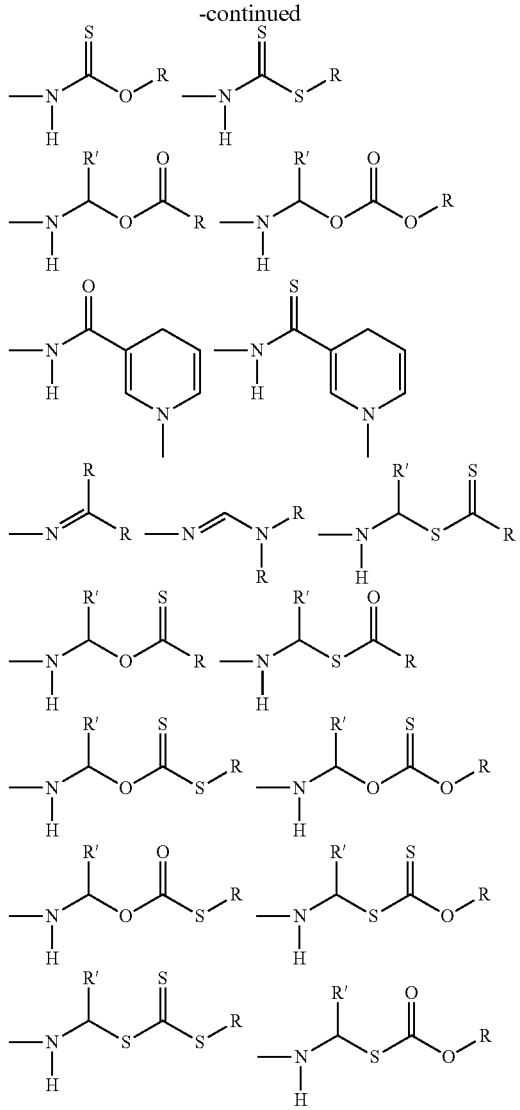

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula (I), (Ia), (Ib), (II), (III), or (IV) are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula (I), (Ia), (Ib), (II), (III), or (IV) described herein are metabolized upon administration to an organism in need to produce a metabolite that is then used to produce a desired effect, including a desired therapeutic effect.

Pharmaceutical Compositions/Formulations

In another aspect, provided herein are pharmaceutical composition comprising a compound of Formula (I), (Ia), (Ib), (II), (III), or (IV) as described herein, or a pharmaceutically acceptable salt, polymorph, solvate, prodrug, metabolite, deuteride, N-oxide, stereoisomer, or isomer thereof, and a pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (Ia), (Ib), (II), (III), or (IV) and at least one pharmaceutically acceptable inactive ingredient. In some embodiments, the compounds described herein are administered as pharmaceutical compositions in which a compound of Formula (I), (Ia), (Ib), (II), (III), or (IV) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (Ib), (II), (III), or (IV) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), pulmonary, intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Described herein is a pharmaceutical composition comprising a compound of Formula (I), (Ia), (Ib), (II), (III), or (IV), and a pharmaceutically acceptable excipient, where the compound is in a formulation suitable for delivery by inhalation. The inhalational route of administration provides the advantage that the inhaled drug can directly target the lung. An inhalational pharmaceutical delivery system is one that is suitable for respiratory therapy by delivery of an active agent to mucosal linings of the bronchi. This invention can utilize a system that depends on the power of a compressed gas to expel an active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in the context of the present disclosure, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

In some embodiments a compound of Formula (I), (Ia), (Ib), (II), (III), or (IV) is formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

In some embodiments, a powder composition containing a compound of Formula (I), (Ia), (Ib), (II), (III), or (IV), with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

Pharmaceutical compositions including a compound of Formula (I), (Ia), (Ib), (II), (III), or (IV) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (Ib), (II), (III), or (IV) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Any conventional carrier or excipient may be used in the pharmaceutical compositions of the embodiments. The choice of a particular carrier or excipient, or combinations of carriers or excipients, will depend on the mode of administration being used to treat a particular patient or type of medical condition or disease state.

Combination Treatment

The compounds according to Formula (I), (Ia), (Ib), (II), (III), or (IV) may be used in combination with one or more additional antibiotic agents, recombinant human DNase, hypertonic saline, anti-inflammatory agents and bronchodilators.

The antibiotic agent may be selected from an aminoglycoside, ansamycin, carbacephem, carbapenem, cephalosporin, glycopeptide, lincosamide, lipopeptide, macrolide, monobactam, nitrofurans, penicillin, polypeptide, quinolone, sulfonamide, or tetracycline antibiotic. Examples of antibiotic agents include, but are not limited to, Aminoglycoside derivatives like amikacin, gentamicin, kanamycin, neomycin, netilmicin, tobramicin, paromomycin; Ansamycin derivatives like geldanamycin, herbimycin; Carbacephem derivatives like loracarbef, Carbapenem derivatives like ertapenem, doripenem, imipenem, meropenem; Cephalosporin derivatives like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; Glycopeptide derivatives like teicoplanin, vancomycin, telavancin; Lincosamides like clindamycin, lincomycin; Lipopeptide derivatives like daptomycin; Macrolide derivatives like azithromycin, clarithromycin, dirithromycin, erythromycin, roxithromycin, troleandomycin; telithreomycin, spectinomycin; Monobactam derivatives like aztreonam; Nitrofuran derivatives like furazolidone, nitrofurantoin; Penicillin derivatives like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; Penicillin combinations like amoxicillin/clavulanate, ampicillin/sulbactam, piperacillin/tazobactam, ticarcillin/clavulanate; Polypeptide derivatives like bacitracin, colistin, polymyxin B; Quinolone derivatives like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; Sulfonamide derivatives like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; Tetracyclin derivatives like demeclocycline, doxycycline, minocycline, oxytetracycline, tetracycline; Derivatives against mycobacteria like clofazimine, dapsone, capreomycin, cycloserine, ethambutol, ethioamide, isoniazid, pyrazinamide, rifampin, refampicin, rifabutin, rifapentine, streptomycin; or other antibiotic agents like arsphenamine, chloramphenicol, fosfomycin, fusidic acid, linezolid, metronidazole, mupirocin, platensimycin, quinupristin/dalfopristin, rifaximin, thiampheniol, tigecycline, tinidazole. In preferred embodiments, the antibiotic agent is useful in the treatment of cystic fibrosis. In further preferred embodiments, the antibiotic agent is useful in the treatment of chronic obstructive pulmonary disease.

Examples of bronchodilator agents include, but are not limited to, $\beta_2$-adrenergic receptor agonists such as albuterol, levalbuterol, pirbuterol, epinephrine, ephedrine, terbutaline, salmeterol, clenbuterol, formoterol, bambuterol, and indacaterol.

Anti-inflammatory agents include, but are not limited to, NSAIDS and glucocorticoids. Non-limiting examples of NSAIDS include aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, and firocoxib. Glucocorticoids include, but are not limited to, hydrocortisone, cortisone, prednisone, prednisolone, methylprednisolone, dexamethasone, betamethasone, triamcinolone, beclometasone, or fludrocortisone.

Administration of Pharmaceutical Composition

In some embodiments, compounds of Formula (I), (Ia), (Ib), (II), (III), or (IV) and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like. In preferred embodiments, compounds of Formula (I), (Ia), (Ib), (II), (III), or (IV) and compositions thereof are administered by inhalation.

Described herein are pharmaceutical compositions comprising a compound of Formula (I), (Ia), (Ib), (II), (III), or (IV) and a pharmaceutically acceptable excipient, where the compound is in a formulation suitable for administration by inhalation, e.g., inhalation into the lungs.

Further described herein are pharmaceutical compositions comprising a compound of Formula (I), (Ia), (Ib), (II), (III), or (IV) utilized for administration wherein absorption is limited such that the compound is rendered substantially impermeable or substantially systemically non-bioavailable by means of increasing the molecular weight of the compound. In some embodiments, the compound of Formula (I), (Ia), (Ib), (II), (III), or (IV) may be rendered substantially impermeable or substantially systemically non-bioavailable by means of having an increased the polar surface area. In a certain embodiment, a compound of Formula (I), (Ia), (Ib), (II), (III), or (IV) is provided having a polar surface area of at least 350 Å$^2$ and a molecular weight of at least 800 Dalton. In certain embodiments, the compound of Formula (I), (Ia), (Ib), (II), (III), or (IV) has a molecular weight of at least 750 Da, at least 900 Da, at least 1000 Da, at least 1100 Da, at least 1200 Da, at least 1300 Da, at least 1400 Da, or at least 1500 Da. In further embodiments, the compound of Formula (I), (Ia), (Ib), (II), (III), or (IV) exhibits a polar surface area of at least 250 Å$^2$, at least 300 Å$^2$, at least 350 Å$^2$, at least 400 Å$^2$, at least 450 Å$^2$, or at least 500 Å$^2$. In further embodiments, the compound is substantially active on the apical side of the epithelium of the lung to locally block ENaC.

For therapeutic use in lung diseases, local delivery to the lung can be carried out. Delivery by inhalation or insufflating aerosols provides high level concentrations of drug compared to the concentration absorbed systemically. Compositions highly selective or localized in the lung act substantially in the lung without exposure to other tissues or organs. In this way, any systemic effects can be minimized. In addition, administration by inhalation can provide for smaller doses delivered locally to the specific cells in the lung which are most in need of treatment. By delivering smaller doses, any adverse side effects are eliminated or substantially reduced. By delivering directly to the cells which are most in need of treatment, the effect of the treatment will be realized more quickly.

The compound of Formula (I), (Ia), (Ib), (II), (III), or (IV) may be administered to the subject by means of a pharmaceutical delivery system for the inhalation route. The compounds may be formulated in a form suitable for administration by inhalation. The pharmaceutical delivery system is one that is suitable for respiratory therapy by administration via inhalation of a compound of any one of Formula (I), (Ia), (Ib), (II), (III), or (IV) thereof to the lung.

In certain embodiments, the pharmaceutical compositions are suitable for inhaled administration. Suitable pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device. When a pharmaceutical aerosol is employed in this invention, the aerosol contains the therapeutically active compound, which can be dissolved, suspended, or emulsified in a mixture of a fluid carrier and a propellant. The aerosol can be in the form of a solution, suspension, emulsion, powder, or semi-solid preparation. Aerosols employed in the present embodiments are intended for administration as fine, solid particles or as liquid mists via the respiratory tract of a patient. Various types of propellants known to one of skill in the art can be utilized. Examples of suitable propellants include, but are not limited to, hydrocarbons or other suitable gas. In the case of the pressurized aerosol, the dosage unit may be determined by providing a value to deliver a metered amount.

In certain embodiments, the pharmaceutical composition comprising a compound of Formula (I), (Ia), (Ib), (II), (III), or (IV) is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size.

In certain embodiments, the pharmaceutical composition comprising a compound of Formula (I), (Ia), (Ib), (II), (III), or (IV) is administered by inhalation using a dry powder inhaler. Such dry powder inhalers typically administer the active agent as a free-flowing powder that is dispersed in a patient's air-stream during inspiration. In order to achieve a free-flowing powder, the active agent is typically formulated with a suitable excipient such as lactose or starch.

In certain embodiments, the pharmaceutical composition comprising a compound of Formula (I), (Ia), (Ib), (II), (III), or (IV) is administered by inhalation using a metered-dose inhaler. Such metered-dose inhalers typically discharge a measured amount of the active agent or a pharmaceutically acceptable salt thereof using compressed propellant gas. Accordingly, pharmaceutical compositions administered using a metered-dose inhaler can comprise a solution or suspension of the active agent in a liquefied propellant.

Methods

Provided herein is a method to treat a lung disease in a mammal, the method comprising administering to the mammal a compound of Formula (I), (Ia), (Ib), (II), (III), or (IV) or as described above and below.

Provided herein is a method to treat cystic fibrosis in a mammal, the method comprising administering to the mammal a compound of Formula (I), (Ia), (Ib), (II), (III), or (IV) or as described above and below.

Also provided herein is a method to treat chronic obstructive pulmonary disease (COPD) in a mammal, the method comprising administering to the mammal a compound of Formula (I), (Ia), (Ib), (II), (III), or (IV) or as described above and below.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris(dimethylamino)phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ trifluoromethanesulfonic anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds of the Invention The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder or Reaxys.

Example 1

Synthesis of Intermediate 12

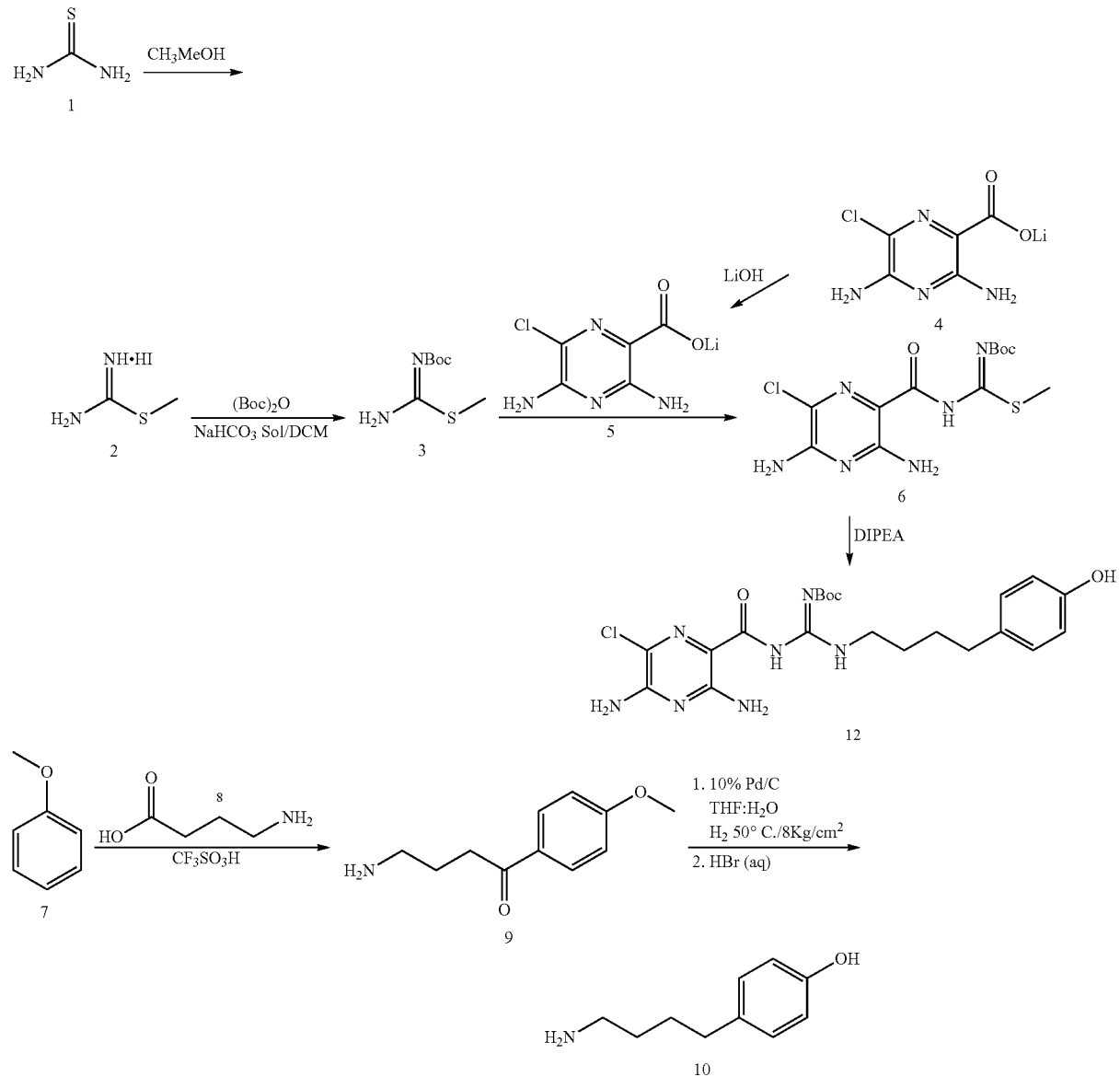

To a stirred solution of thiourea (5.0 g, 65.68 mmol) in methanol (50 mL) was added methyl iodide (4.1 mL, 65.68 mmol) dropwise at room temperature under $N_2$. The temperature was increased to 65° C. and the solution was stirred for 2 h. After reaction completion, the solvent was concentrated under reduced pressure to obtain a solid, which was washed with IPE (100 mL) and ethyl acetate (5×100 mL) until yellow color disappeared. The compound was dried under vacuum to yield 2 as a white powder (13.6 g, 95%).

To a stirred solution of 2 (5.0 g, 22.92 mmol) in saturated sodium bicarbonate solution (50 mL) and dichloromethane (200 mL) was added Boc anhydride (5.2 mL, 22.92 mmol). The reaction was stirred for 1 h at room temperature. The organic layer was separated and washed with brine solution (100 mL). The organic layer was concentrated under reduced pressure to give crude material, which was purified by column chromatography (10% EtOAc in hexane) to yield 3 (2.2 g, 51.1%). Mass (m/z): 190.9 [M+H].

To a suspension of 3,5-diamino-6-chloro-pyrazine-2-carboxylic acid methyl ester (10.0 g, 49.35 mmol) in methanol (5 mL) was added lithium hydroxide solution (4.17 g, 98.7 mmol in 40 mL water) at room temperature. The reaction was heated to 50° C. and stirred for 2-3 h. The temperature was lowered to room temperature and the reaction stirred overnight. The resulting precipitate was collected by filtration and dried under vacuum to yield 5 (11.3 g, 97%). Mass (m/z): 187 [M-Li].

To a stirred solution of 5 (4.0 g, 17.34 mmol) in dry DMF (80 mL) was added HATU (7.25 g, 19.09 mmol) portionwise at room temperature. The solution was stirred for 2 h. 2-Methyl-N-Boc isothiourea (3.64 g, 19.07 mmol) was added to the reaction mixture and stirred for 2 h at room temperature, then heated and maintained overnight at 50° C. After completion of the reaction, the reaction solution was cooled to room temperature. Water (40 mL) was added, and the solution was filtered and dried to provide 6 (3.6 g, 91.7%). Mass (m/z): 360.9 [M+H].

4-Amino butyric acid (3.4 g, 33.29 mmol) was added portion-wise to ice cooled trifluoromethane sulfonic acid (12.6 mL, 144.24 mmol). To the solution was added anisole (3.0 g, 27.74 mmol) drop-wise and the contents heated to 80° C. and stirred for 1 h. After completion of the reaction, the mixture was cooled to 0° C. and diluted with water (20 mL) and stirred for 30 min to form a yellow solid. The solid was filtered and dried to yield 9 (6.8 g, 71.5%). Mass (m/z): 193.9 [M+H].

To a solution of 9 (6.8 g, 19.82 mmol) in THF/water (1:1 ratio, 70 mL) was added 1 g of 10% Pd/C under $N_2$ in a steel bomb and hydrogenated at 60 PSI with stirring for 24 h at 50° C. After completion of the reaction, the mixture was filtered, and the filtrate basified with 2N KOH (25 mL) and extracted with toluene (2×50 mL). The combined organic layers were dried over $Na_2SO_4$ and concentrated under reduced pressure to give 4-(4-methoxyphenyl)butan-1-amine as a liquid (2.92 g, 80.0%). The liquid was re-dissolved in aq. HBr solution (29 mL) and heated to 90° C. for 3 h. After completion of the reaction, HBr solution was concentrated under reduced pressure to provide 10 (2.2 g, 88.7%). Mass (m/z): 166.1 [M+H].

To a solution of 10 (0.778 g, 2.394 mmol) in a mixture of THF (10 mL) and DMF (12 mL) was added triethylamine (1.39 mL, 9.975 mmol) at 0° C. The solution was stirred for 30 min. Intermediate 6 (0.72 g, 1.995 mmol) was added portion-wise to the solution and stirred overnight at room temperature. After completion of reaction (monitored by TLC), the mixture was concentrated to obtain crude material which was purified by column chromatography (2% MeOH/DCM) to yield 12 (0.45 g, 47.3%). Mass (m/z): 478.0 [M].

Example 2

Synthesis of Intermediates 15a, 15b, and 15c

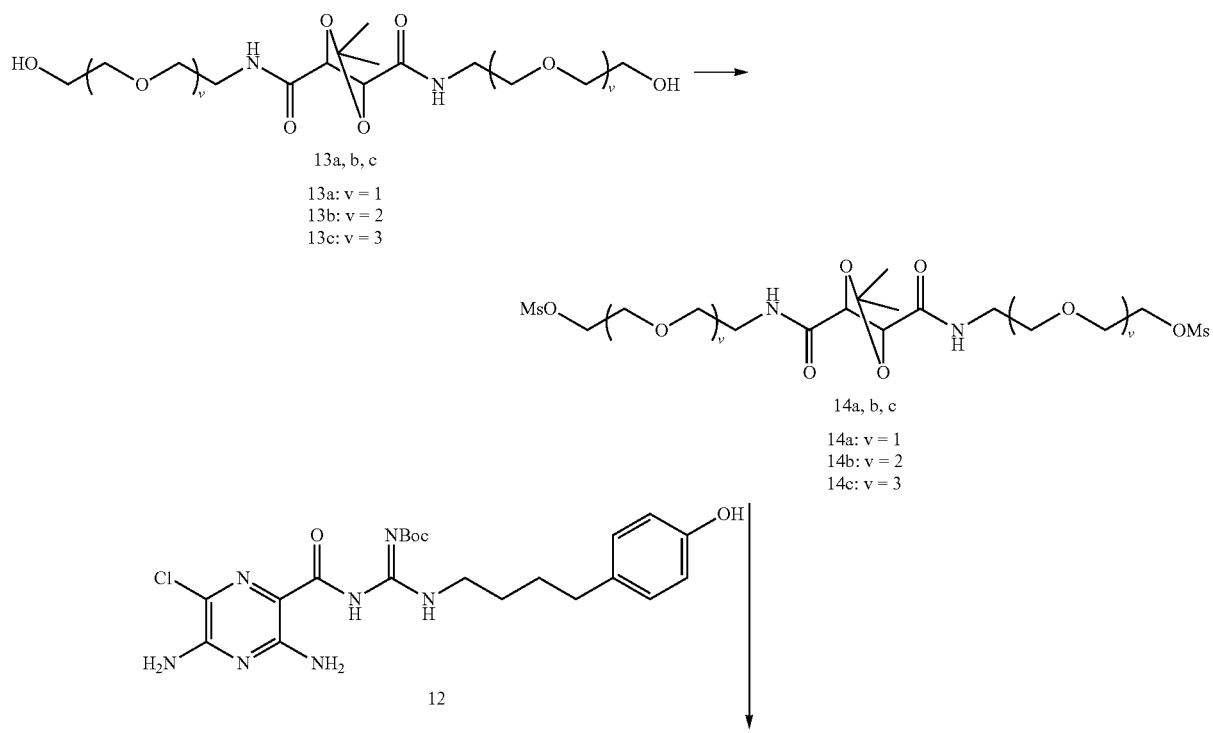

13a, b, c

13a: v = 1
13b: v = 2
13c: v = 3

14a, b, c

14a: v = 1
14b: v = 2
14c: v = 3

12

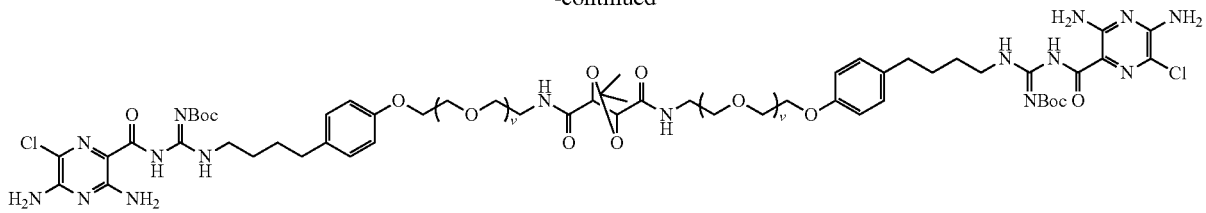

15a, b, c

15a: v = 1
15b: v = 2
15c: v = 3

To a stirred solution of intermediate 13a (0.2 g, 0.37 mmol) in DCM (5 mL) was added TEA (0.15 mL, 1.1 mmol) dropwise at 0° C. under $N_2$. After being stirred for 30 min at room temperature, methane sulfonylchloride (0.08 mL, 1.11 mmol) was added and the reaction stirred for 4 h at room temperature. After reaction completion, 1N HCl (5 mL) was added and the separated organic layer was washed with sat. $NaHCO_3$ solution and brine. The organic layer was dried over $Na_2SO_4$ and concentrated under reduced pressure to obtain 14a (200 mg, 86.9%), which was used directly in the next step without any further purification. Mass (m/z): 521 [M+H].

Synthesis of Intermediate 14b

Compound 14b was prepared from intermediate 13b according to the protocol for compound 14a. Mass (m/z): 608.6 [M].

Synthesis of Intermediate 14c

Compound 14c was prepared from intermediate 13c according to the protocol for compound 14a. Mass (m/z): 696.9 [M].

Synthesis of Intermediate 15a

To a mixture of compound 12 (0.4 g, 0.882 mmol) and $Cs_2CO_3$ (0.67 g, 2.076 mmol) in DMF (10 mL) was added a solution of compound 14a (0.27 g, 0.519 mmol). The solution was stirred for 2 days under $N_2$. After completion of the reaction, the mixture was filtered and concentrated to give crude material which was purified by preparative HPLC to yield 15a (75 mg, 6.9%) with 97.6% purity by LC-MS; Mass: 1283.4 [M+H].

Synthesis of Intermediate 15b

Compound 15b was prepared according to the protocol for compound 15a using 12 (0.25 g, 0.53 mmol), $Cs_2CO_3$ (0.813 g, 2.49 mmol) in DMF (8 mL) and compound 14b (0.19 g, 0.312 mmol). The crude product was purified by preparative HPLC to provide 15b (70 mg, 9.7%). Purity by LC-MS: 97.6%; Mass: 1371.5 [M−H].

Synthesis of Intermediate 15c

Compound 15c was prepared according to the protocol for compound 15a using 12 (0.25 g, 0.53 mmol), $Cs_2CO_3$ (0.813 g, 2.49 mmol) in DMF (3.8 mL) and compound 14c (0.214 g, 0.307 mmol). The crude product was purified via preparative HPLC to provide 15c (40 mg, 8.9%). Purity by LC-MS: 95.26%; Mass: 1461.5 [M+H].

Example 3

Synthesis of Compound 16

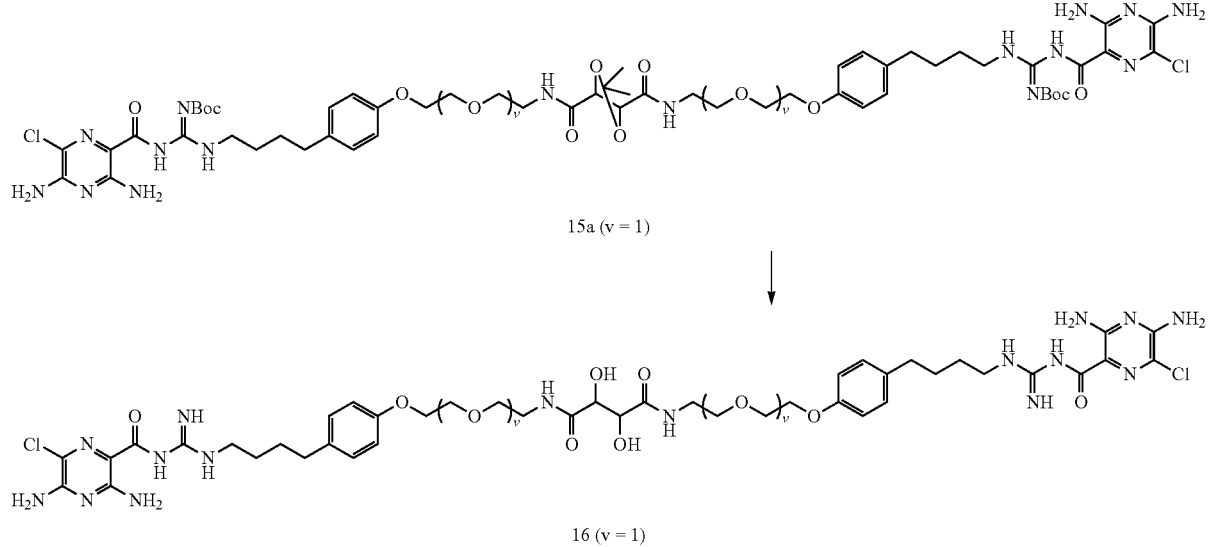

To a solution of compound 15a (70 mg, 0.0545 mmol) in acetonitrile (5 mL) was added 6N HCl (3 mL). The solution was stirred for 4 h at room temperature. After completion of the reaction, solvents were condensed under reduced pressure to give crude material which was purified by preparative HPLC to provide 16 (20 mg, 33.0%) with 97.04% purity by LC-MS; Mass m/z value: 1043.3 [M+H].

$^1$HNMR (400 MHz: CD$_3$OD) δ 9.2 (brs, 1H), 7.15 (s, 2H), 6.8 (s, 2H), 4.6 (brs, 2H), 4.1 (s, 2H), 3.2-3.9 (m, 6H), 2.6 (s, 2H), 2.0 (s, 2H), 1.65 (s, 2H), 1.4 (d, 2H).

Example 4

Synthesis of Compound 17

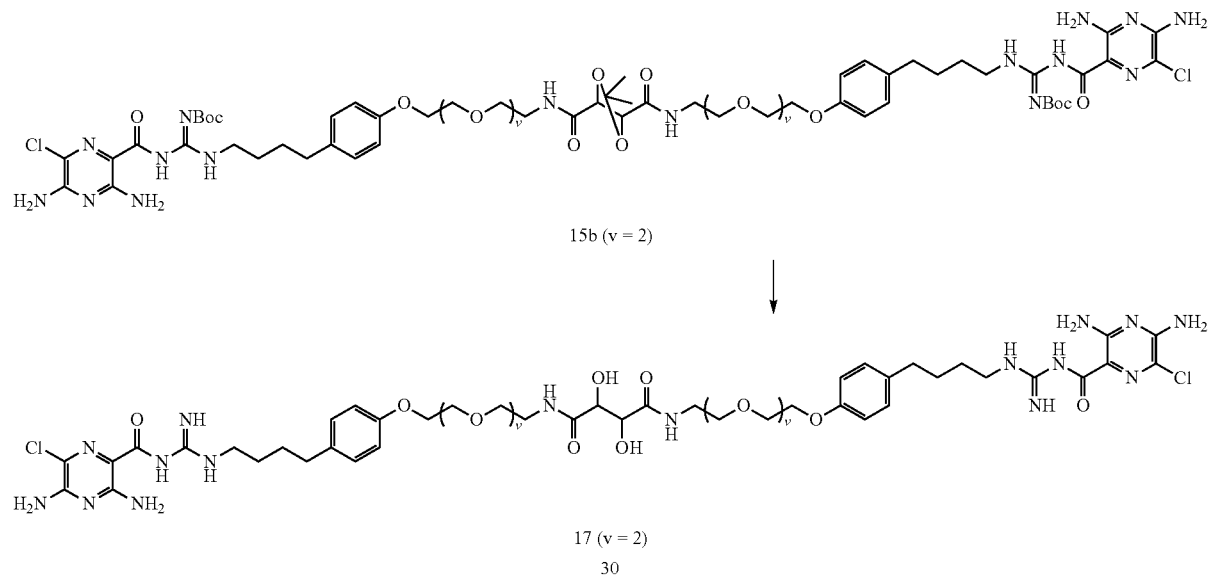

Compound 17 was prepared according to the protocol for compound 16 using 15b (70 mg, 0.051 mmol), acetonitrile (2 mL), and 6N HCl (5 mL). The crude material was purified by preparative HPLC to provide 17 (20 mg, 34.4%) with 97.8% purity by LC-MS; Mass (m/z): 1131.3 [M−H+]. $^1$HNMR (600 MHz: DMSO-d$_6$) δ 10.6 (s, 2H), 9.35 (s, 2H), 8.8-9.1 (d, 4H), 7.7 (s, 4H), 7.4 (brs, 4H), 7.15 (d, 4H), 6.85 (d, 4H), 4.25 (s, 2H), 4.05 (s, 4H), 3.65 (s, 4H), 3.4-3.6 (m, 12H), 3.25 (s, 8H), 2.55 (s, 2H), 2.1 (s, 3H), 1.75 (s, 1H), 1.6 (s, 8H), 1.2 (s, 1H).

Example 5

Synthesis of Compound 18

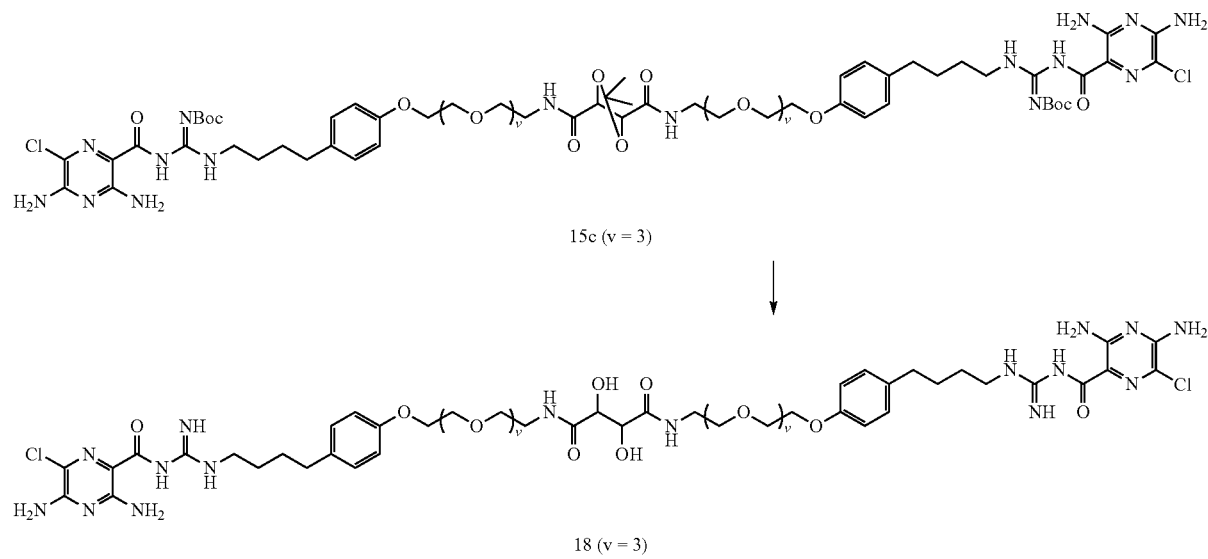

Compound 18 was prepared according to the protocol for compound 16 using compound 15c (75 mg, 0.051 mmol), acetonitrile (5 mL), and 6N HCl (3 mL). The crude material was purified via preparative HPLC to provide 18 (20 mg, 31.9%) with 95.8% purity by LC-MS; Mass (m/z): 1219.3 [M+H]. $^1$HNMR (600 MHz: DMSO-$d_6$) δ 10.6 (s, 2H), 9.35 (s, 2H), 8.8-9.1 (d, 4H), 7.6 (s, 2H), 7.4 (bs, 4H), 7.22-7.3 (m, 2H), 7.15 (d, 4H), 6.85 (d, 4H), 6.65 (s, 1H), 4.25 (s, 2H), 4.05 (s, 6H), 3.65 (s, 4H), 3.2-3.45 (m, 18H), 3.25 (m, 4H), 2.5 (s, 2H), 2.05 (s, 3H), 1.75 (s, 2H), 1.8 (s, 2H), 1.4-1.65 (m, 8H), 1.15-1.25 (m, 6H).

Example 6

Synthesis of Intermediate 23

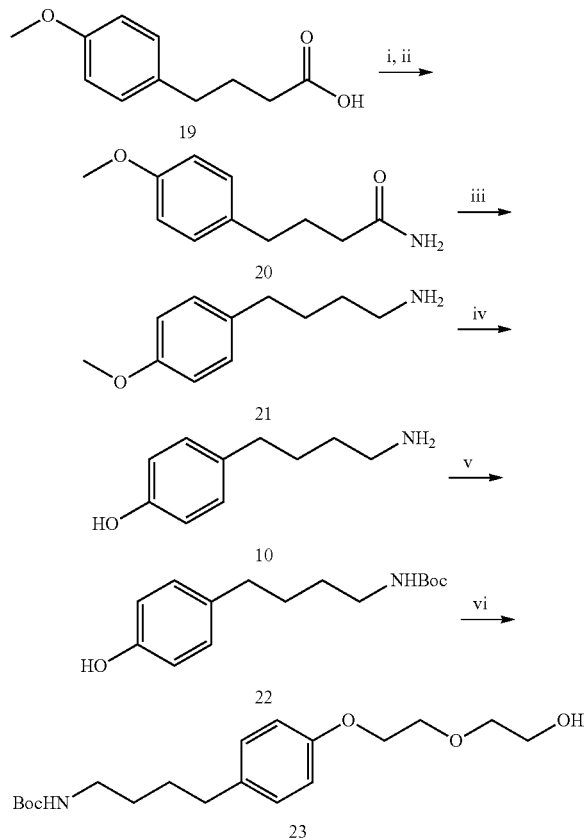

Reagents and conditions (i) iso-butylchloroformate, NMM, THF; (ii) NH$_3$, MeOH; (iii) LAH/THF; (iv) 48% HBr; (v) Boc anhydride, NaHCO$_3$, DCM; (vi) 2-(2-chloroethoxy) ethanol, K$_2$CO$_3$, MeCN.

To a solution of 4-(4-methoxyphenyl)butyric acid (19) (1.0 g, 5.1 mmol) in THF (20 mL) was added 4-methylmorpholine (572 mg, 5.7 mmol) at 0° C. under nitrogen atmosphere. To this solution, iso-butylchloroformate (842 mg, 6.2 mmol) was added dropwise over 5 minutes. After stirring for 30 min at 0° C., a 7M solution of ammonia in methanol (1.45 mL, 10.3 mmol) was added. The reaction was stirred overnight. To the reaction mixture, ethyl acetate (150 mL) was added and extracted with water and brine solution. The organic layers were dried over anhydrous sodium sulphate, filtered and concentrated under vacuum. The crude product was crystallized from ethyl acetate and hexane to afford 4-(4-methoxyphenyl)butanamide (20) as a white solid (920 mg, 93%). $^1$H NMR (400 MHz, CDCl$_3$) δ 1.94-1.98 (m, 2H), 2.23 (t, J=7.7 Hz, 2H), 2.64 (t, J=7.7 Hz, 2H), 3.81 (s, 3H), 6.85 (d, J=8.7 Hz, 2H), 7.12 (d, J=8.7 Hz, 2H); Mass (m/z) 194 (M+H).

To a solution of 4-(4-methoxyphenyl)butanamide (20) (2.0 g, 10.3 mmol) in anhydrous THF (50 mL) at 0° C. under nitrogen atmosphere. To this solution, LAH (782 mg, 20.5 mmol) was added in two portions, and the reaction was warmed to room temperature and stirred overnight. After completion of the reaction, the reaction mixture was cooled to 0° C. and 1N NaOH was added dropwise. The reaction mixture was filtered over celite and the filtrate was diluted with ethyl acetate (200 mL), and then washed with water and brine. The combined organic layers were dried over anhydrous sodium sulphate, filtered and concentrated under vacuum to afford 4-(4-methoxyphenyl)butan-1-amine (10) (1.8 g, 97%). $^1$H NMR (400 MHz, CDCl$_3$) δ 1.63-1.66 (m, 4H), 2.59 (t, J=7.9 Hz, 2H), 2.81 (t, J=7.9 Hz, 2H), 3.80 (s, 3H), 5.54 (br s, 3H), 6.84 (d, J=8.0 Hz, 2H), 7.10 (d, J=8.0 Hz, 2H); Mass m/z 180 (M+H).

4-(4-methoxyphenyl)butan-1-amine (10) (1.8 g, 10.0 mmol) was taken in a round bottom flask. A 48% aqueous HBr solution (20 mL) was slowly added to the reaction at room temperature. After addition, the reaction mixture was stirred at reflux for 3 h. After completion of the reaction, the reaction mixture was cooled to 0° C., and then suction filtered to afford an off-white solid, which was further dried under vacuum for overnight to afford 4-(4-aminobutyl) phenol hydrobromide (21) (1.4 g, 84%). $^1$H NMR (400 MHz, CDCl$_3$) δ 1.52-1.54 (m, 4H), 2.46-2.52 (m, 2H), 2.78 (t, J=7.9 Hz, 2H), 6.68 (d, J=8.0 Hz, 2H), 6.99 (d, J=8.0 Hz, 2H); Mass m/z 166 (M+H).

To a solution of 4-(4-aminobutyl)phenol hydrobromide (21) (1 g, 4.1 mmol) in 1,4-dioxane (40 mL) was added sodium bicarbonate (1.38 g, 16.4 mmol) in water (40 mL) and the mixture was stirred at 0° C. Di-tert-butyl dicarbonate (980 mg, 4.49 mmol) was added to the reaction mixture and the reaction was warmed to room temperature and stirred overnight. The reaction mixture was then diluted with ethyl acetate (150 mL) and washed with water and brine. The organic layer were dried over sodium sulphate and evaporated. The crude mixture was purified by column chromatography (20% EtOAc:Hexenes) to afford pure compound 22 as a white solid (1.1 g, 70%). $^1$H NMR (400 MHz, CDCl$_3$) δ 1.46-1.58 (m, 13H), 2.52-2.55 (m, 2H), 3.14 (br s, 2H), 6.79 (d, J=7.7 Hz, 2H), 7.01 (d, J=7.6 Hz, 2H); MS m/z 266 (M+H).

To a solution of 22 (500 mg, 1.8 mmol) in anhydrous acetonitrile (10 mL) under nitrogen atmosphere were added 2-(2-chloroethoxy)ethanol (256 mg, 2.1 mmol), K$_2$CO$_3$ (778 mg, 5.6 mmol) and potassium iodide (312 mg, 1.8 mmol). The reaction mixture was stirred at reflux for 10 h. After completion of the reaction, the mixture was filtered and concentrated in vacuo. The residue was purified by column chromatography (40% EtOAc:Hexenes) to afford pure compound 23 (480 mg, 72%) as a colorless liquid. $^1$H NMR (400 MHz, CDCl$_3$) δ 1.45 (br s, 11H), 2.60-2.62 (m, 2H), 1.83 (s, 2H), 2.58 (t, J=6.8 Hz, 2H), 3.14 (brs, 2H), 3.69-3.70 (m, 2H), 3.78 (s, 2H), 3.88 (s, 2H), 4.14 (s, 2H), 6.86 (d, J=7.8 Hz, 2H), 7.09 (d, J=7.8 Hz, 2H); MS m/z 354 (M+H).

Example 7

Synthesis of Compound 28

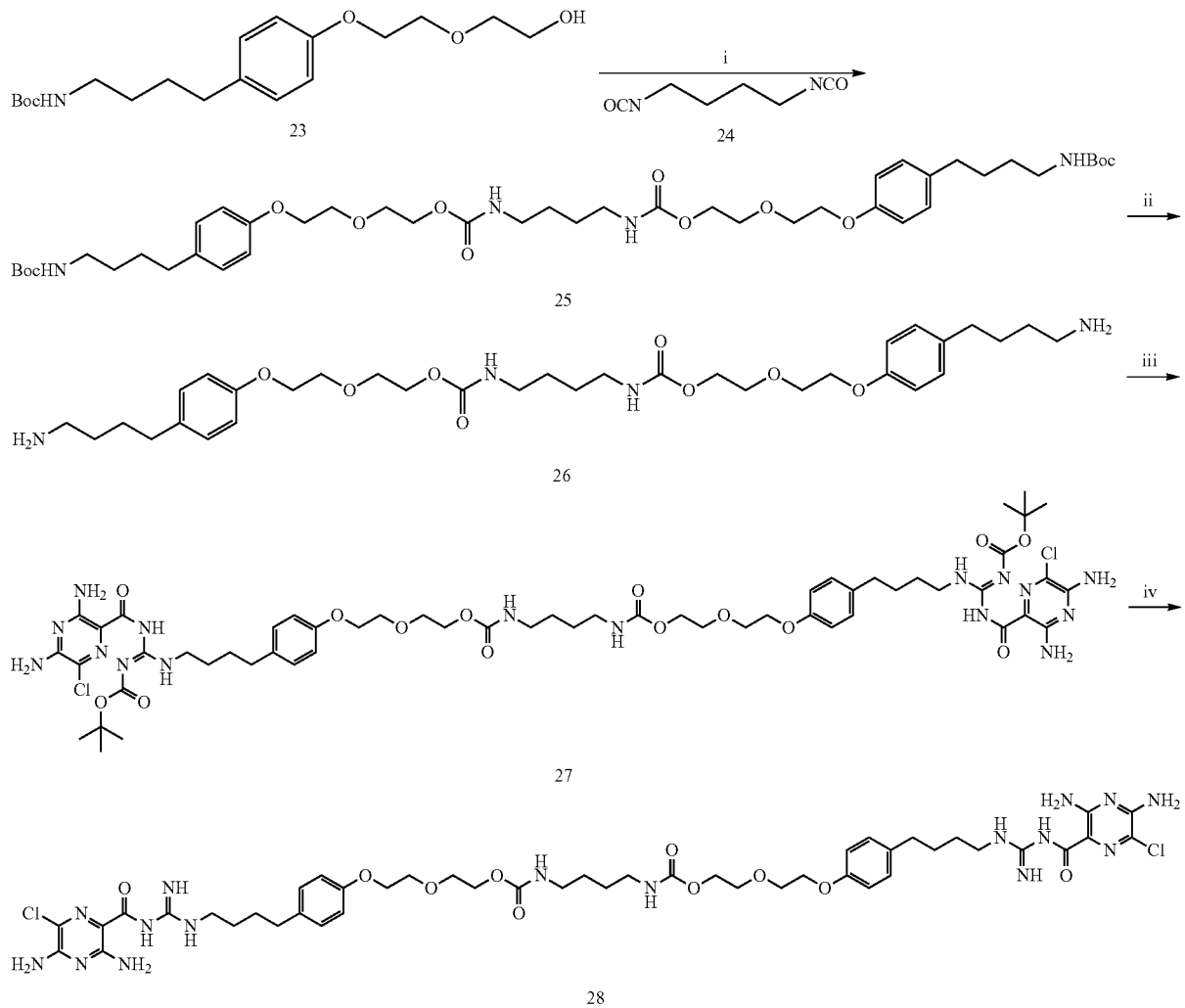

Reagents and conditions used in the Scheme above: (i) Triethylamine, toluene; (ii) HCl, 1,4-dioxane; (iii) Tert-butyl-(3,5-diamino-6-chloropyrazine-2-carboxamido)(methylthio)methylenecarbamate, DIPEA, EtOH; (iv) HCl, 1,4-dioxane.

To a mixture of 23 (100 mg, 0.28 mmol) and 1,4-diisocyanobutane (19 mg, 0.14 mmol) in anhydrous toluene (10 mL) under nitrogen atmosphere was added triethylamine (85 mg, 0.84 mmol). The reaction mixture was stirred at reflux for 6 h. After completion of the reaction, solvent was evaporated under vacuum to give crude product (25) which was identified by LCMS, in which major peak was showing m/z as 847 (M+H). The compound was used for further reaction without purification.

A solution of 25 in 4M HCl in 1,4-dioxane solution (5 mL) was stirred at room temperature for 30 minutes. The progress of the reaction was monitored by LCMS. After completion of the reaction, the solvent was evaporated by vacuum to give crude compound (26) as a white solid which was identified by LCMS, in which major peak was showing m/z as 647 (M+H). The compound was used for further reaction without purification.

To a solution of 26 (90 mg, 1.4 mmol) in anhydrous ethanol was added Hunig's base (DIPEA) (108 mg, 8.4 mmol), and this solution was heated at reflux for 15 minutes. Intermediate 6 from Example 1 (110 mg, 3.04 mmol) was then added. The reaction mixture was stirred at reflux for 3 h, and then cooled to room temperature. The yellow solid was filtered and washed with ethanol to give compound 27, which was identified by LCMS as m/z 1271 (M+H) (major peak). The compound was used in the next reaction without further purification.

A solution of 27 in 4M HCl in 1,4-dioxne (5 mL) was stirred at room temperature for 1 h. The crude product mixture was evaporated under vacuum and purified by Prep HPLC using a 30-70% linear gradient of acetonitrile in water gradient (0.05% TFA modified mobile phase) to afford final compound (28) as a light yellow solid after evaporation/lyophilization. $^1$H NMR (400 MHz, MeOD) δ 1.35 (s, 2H), 1.51-1.52 (m, 4H), 2.47 (t, J=6.5, 2H), 2.95 (s, 2H), 3.09 (s, 2H), 3.61-3.62 (m, 2H), 3.69-3.72 (m, 2H), 3.94 (s, 2H), 4.05 (t, J=4.1 Hz, 2H), 6.71 (d, J=8.4 Hz, 2H), 6.97 (d, J=8.4 Hz, 2H); Mass (m/z) 1071 (M+H); Anal. ($C_{46}H_{64}Cl_2N_{16}O_{10}·H_2O$) Calcd. C, 50.69; H, 6.10; N, 20.56. Found C, 50.67; H, 6.01; N, 19.82.

Example 8

Synthesis of Compound 29

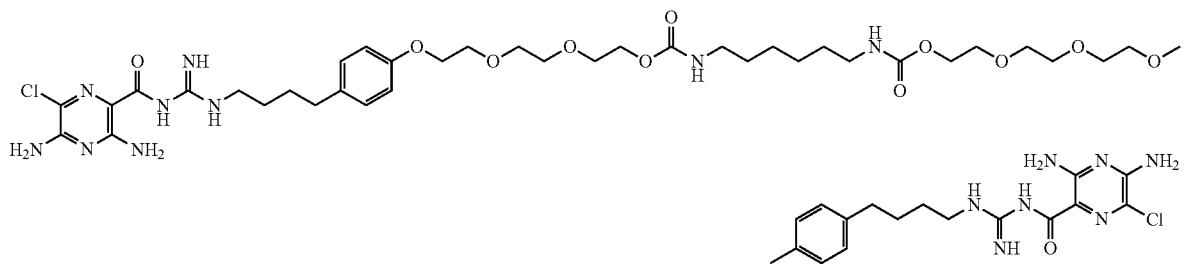

29

Compound 29 was prepared using a similar procedure as detailed in Example 7. $^1$H NMR (400 MHz, MeOD) δ 0.92 (brs, 1H), 1.31-1.35 (m, 6H), 1.47 (s, 2H), 1.71 (brs, 3H), 2.06 (s, 1H), 2.64 (s, 2H), 3.07 (s, 2H), 3.68-3.69 (m, 5H), 3.83 (s, 2H), 4.09 (s, 2H), 4.15 (s, 2H), 6.86 (d, J=7.7 Hz, 2H), 7.11 (d, J=7.7 Hz, 2H); MS m/z 1188 (M+H).

Example 9

Synthesis of Compound 30

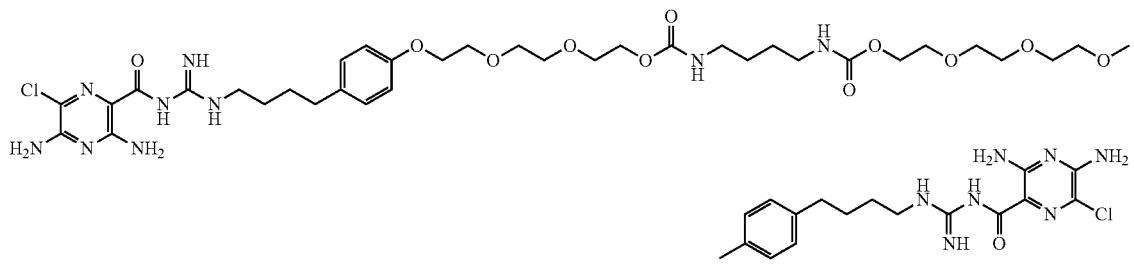

30

Compound 30 was prepared using a similar procedure as detailed in Example 7. $^1$H NMR (400 MHz, MeOD) δ 1.48 (s, 2H), 1.70-1.72 (m, 4H), 2.64 (s, 2H), 3.08 (s, 2H), 3.67-3.69 (m, 6H), 3.82-3.84 (m, 2H), 4.09 (t, J=4.4 Hz, 2H), 4.15 (t, J=4.4 Hz, 2H), 6.86 (d, J=8.4 Hz, 2H), 7.13 (d, J=8.4 Hz, 2H); MS m/z 1160 (M+H).

Example 10

Synthesis of Compound 31

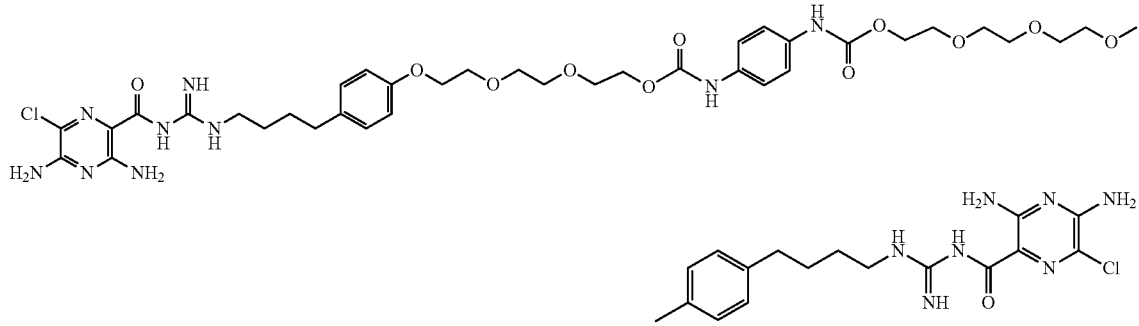

31

Compound 31 was prepared using a similar procedure as detailed in Example 7. $^1$H NMR (400 MHz, MeOD) δ 1.69 (t, J=3.2 Hz, 4H), 2.67 (s, 2H), 3.69-3.76 (m, 6H), 3.83 (t, J=4.7 Hz, 2H), 4.07 (t, J=4.3 Hz, 2H), 4.26 (t, J=4.5 Hz, 2H), 6.83 (d, J=8.5 Hz, 2H), 7.09 (d, J=8.5 Hz, 2H), 7.33 (s, 2H); MS m/z 1180 (M+H).
Example 11
Synthesis of Compound 32
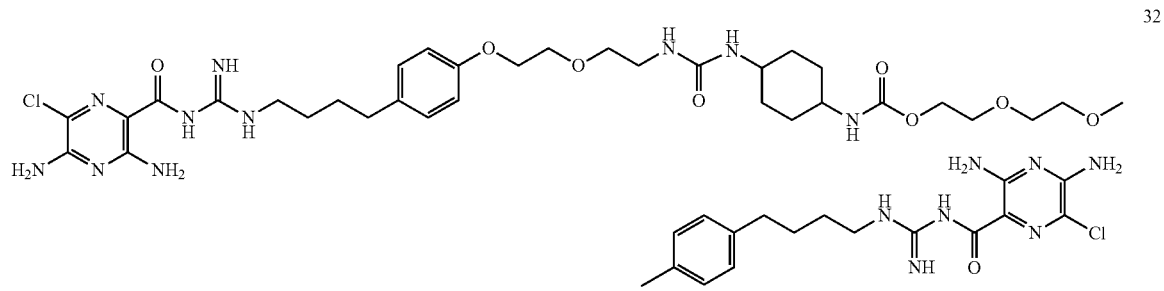
Compound 32 was prepared using a similar procedure as detailed in Example 7. $^1$H NMR (400 MHz, MeOD) δ 1.22-1.29 (m, 3H), 1.63 (brs, 4H), 1.86 (s, 2H), 2.59 (s, 2H), 3.21 (s, 2H), 3.73 (s, 2H), 3.81 (s, 2H), 4.06 (s, 2H), 4.16 (s, 2H), 6.83 (d, J=7.6 Hz, 2H), 7.09 (d, J=7.6 Hz, 2H); MS m/z 1098 (M+H).
Example 12
Synthesis of Compound 37
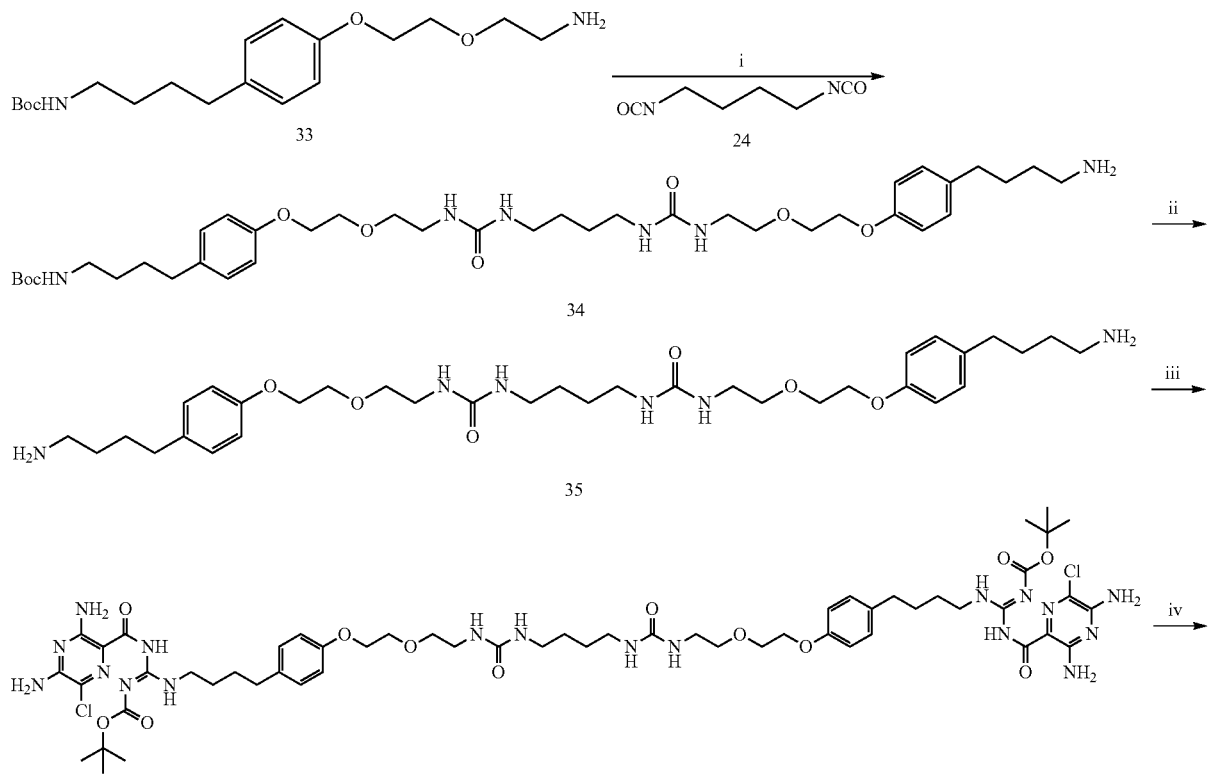

-continued

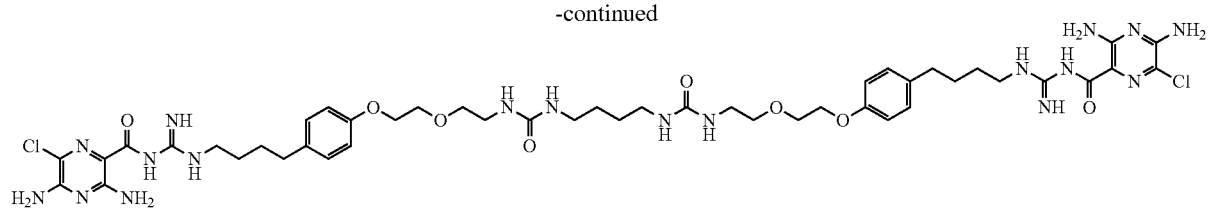

37

Reagents and conditions (i) Triethylamine, toluene; (ii) HCl, 1,4-dioxane; (iii) Tert-butyl-(3,5-diamino-6-chloropyrazine-2-carboxamido)(methylthio)methylenecarbamate, DIPEA, EtOH; (iv) HCl, 1,4-dioxane.

To a solution of tert-butyl 4-(4-(2-(2-aminoethoxy)ethoxy)phenyl)butylcarbamate (33) (100 mg, 0.28 mmol) in anhydrous DCM (20 mL) at 0° C. under nitrogen atmosphere was added 1,4-diisocyanobutane (20 mg, 0.14 mmol). After addition, the temperature was raised to room temperature and stirred for 2 h. The reaction solution was then concentrated under vacuum and the residue crystallized in DCM/Hexanes to give bis-urea linker (34). Mass m/z 845 (M+H).

Compound 37 was prepared in three steps from compound 34 using a similar procedure as detailed in Example 7. $^1$H NMR (400 MHz, MeOD) δ 1.33 (s, 2H), 1.53 (brs, 4H), 2.49 (s, 2H), 2.97 (s, 2H), 3.11 (s, 2H), 3.46 (s, 2H), 3.68 (s, 2H), 3.97 (s, 2H), 6.73 (d, J=7.5 Hz, 2H), 6.99 (d, J=7.5 Hz, 2H); MS m/z 1069 (M+H).

Example 13

Synthesis of Compound 38

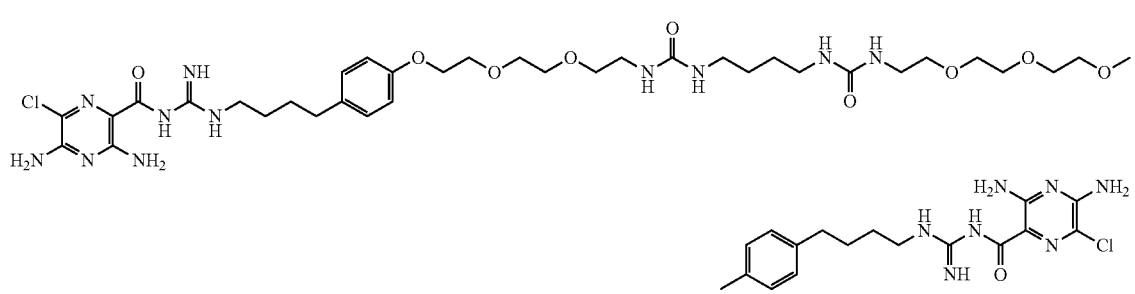

Compound 38 was prepared using a similar procedure as detailed in Example 12. $^1$H NMR (400 MHz, MeOD) δ 1.43-1.44 (m, 2H), 1.62-1.69 (m, 4H), 2.60 (t, J=6.7, 2H), 3.08 (m, 2H), 3.23 (m, 2H), 3.28 (t, J=5.3 Hz, 2H), 3.52 (t, J=5.3 Hz, 2H), 3.62-3.64 (m, 2H), 3.69-3.11 (m, 2H), 3.81-3.84 (m, 2H), 4.09 (t, J=4.4 Hz, 2H), 6.84 (d, J=8.5 Hz, 2H), 7.10 (d, J=8.5 Hz, 2H); MS m/z 1157 (M+H); Anal. ($C_{50}H_{74}Cl_2N_{18}O_{10}$·2H$_2$O) Calcd. C, 50.29; H, 6.58; N, 21.11. Found C, 50.72; H, 6.40; N, 20.63.

Example 14

Synthesis of Compound 39

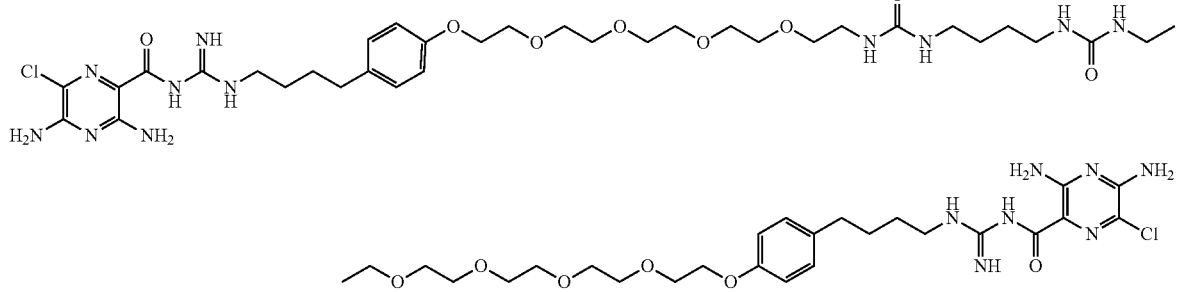

Compound 39 was prepared using a similar procedure as detailed in Example 12. ¹H NMR (400 MHz, MeOD) δ 1.47 (s, 2H), 1.71 (brs, 4H), 2.64 (s, 2H), 3.10 (s, 2H), 3.49 (s, 2H), 3.60-3.71 (m, 12H), 3.83 (s, 2H), 4.09 (s, 2H), 6.86 (d, J=7.7 Hz, 2H), 7.13 (d, J=7.7 Hz, 2H); MS m/z 1333 (M+H).
Example 15
Synthesis of Compound 40
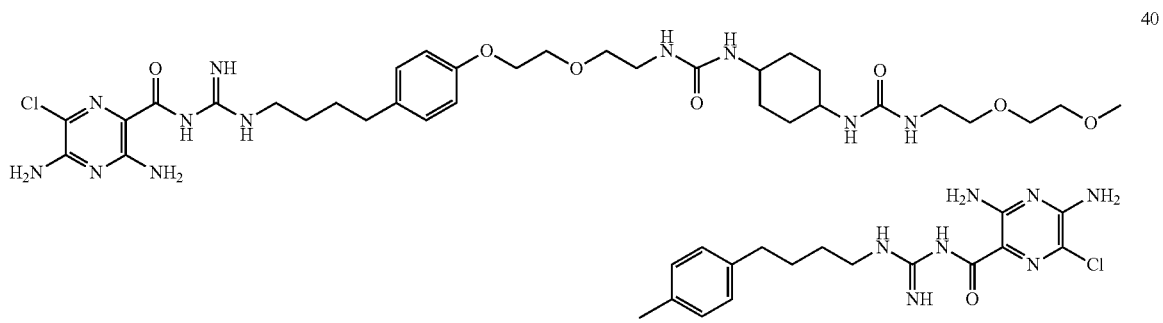
Compound 40 was prepared using a similar procedure as detailed in Example 12. ¹H NMR (400 MHz, MeOD) δ 1.05 (s, 2H), 1.18 (s, 1H), 1.52 (brs, 4H), 1.74 (s, 2H), 2.48 (s, 2H), 3.46 (s, 2H), 3.68 (s, 2H), 3.96 (s, 2H), 6.72 (d, J=7.7 Hz, 2H), 6.98 (d, J=7.7 Hz, 2H); MS m/z 1096 (M+H).
Example 16
Synthesis of Compound 46
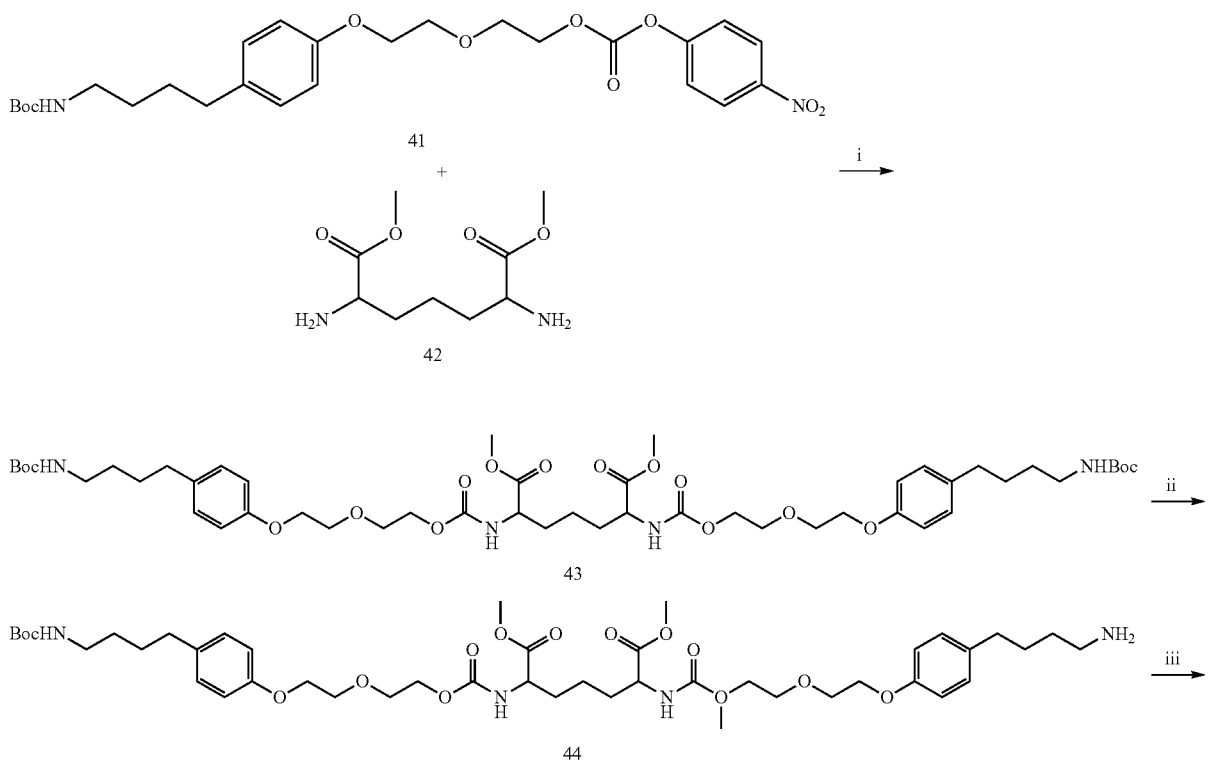

-continued

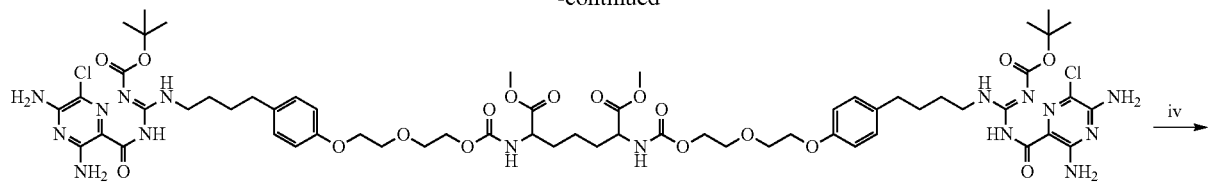

45

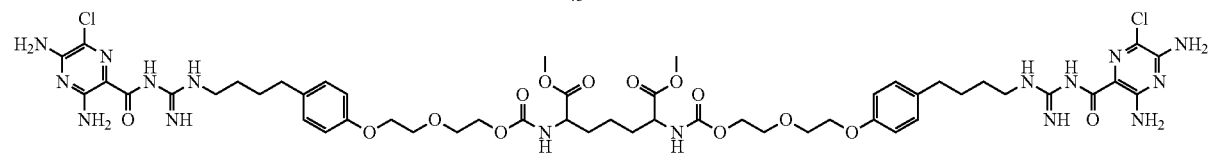

46

Reagents and conditions (i) Diisopropylethylamine, DMF, rt; (ii) HCl, 1,4-dioxane; (iii) Tert-butyl-(3,5-diamino-6-chloropyrazine-2-carboxamido)(methylthio)methylenecarbamate, DIPEA, EtOH; (iv) HCl, 1,4-dioxane.

To a mixture of benzyl-4-(4-(2-(2-((4-nitrophenoxy)carbonyloxy)ethoxy)ethoxy)phenyl)butylcarbamate 41 (100 mg, 0.18 mmol) and DIPEA (25 mg, 0.18 mmol) in dry DMF (5 ml) was added dimethyl-2,6-diaminoheptanedioate 42 (19.7 mg, 0.09 mmol). The reaction mixture was stirred at room temperature for overnight. After completion of the reaction, DMF was dried under high vacuum and residue was diluted with ethyl acetate and washed with brine to afford bis-ester linker 43. Mass m/z 1045 (M+H).

Compound 46 was prepared in three steps from compound 43 using a similar procedure as detailed in Example 7. $^1$H NMR (400 MHz, MeOD) δ 1.19-1.23 (m, 1H), 1.32 (brs, 1H), 1.59 (brs, 6H), 2.52 (s, 2H), 3.58-3.71 (m, 6H), 3.96-4.09 (5H), 6.74 (d, 7.6 Hz, 2H), 7.01 (d, J=7.7 Hz, 2H); Mass m/z 1201 (M+H).

Example 17

Synthesis of Compound 47

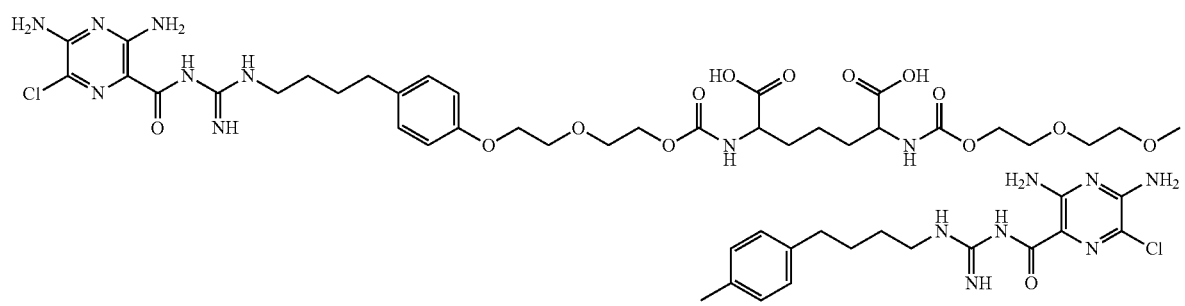

47

Compound 47 was prepared from compound 46 following a saponification step. $^1$H NMR (400 MHz, MeOD) δ 1.47-1.53 (m, 1H), 1.69 (s, 4H), 1.81 (s, 1H), 2.60-2.61 (m, 2H), 3.72-3.74 (m, 2H), 3.81-3.82 (m, 2H), 4.06-4.19 (m, 4H), 6.84 (d, J=8.2 Hz, 2H), 7.10 (d, J=8.2 Hz, 2H); MS m/z 1175 (M+H).

Example 18

Synthesis of Compound 50

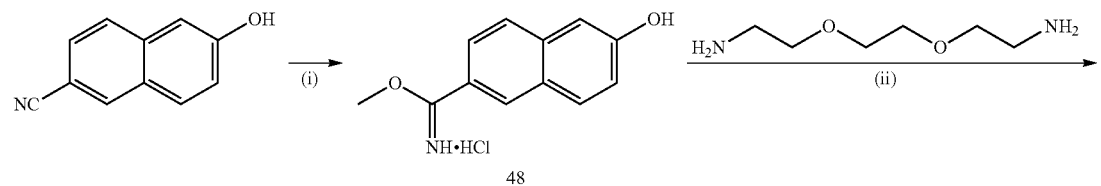

48

-continued

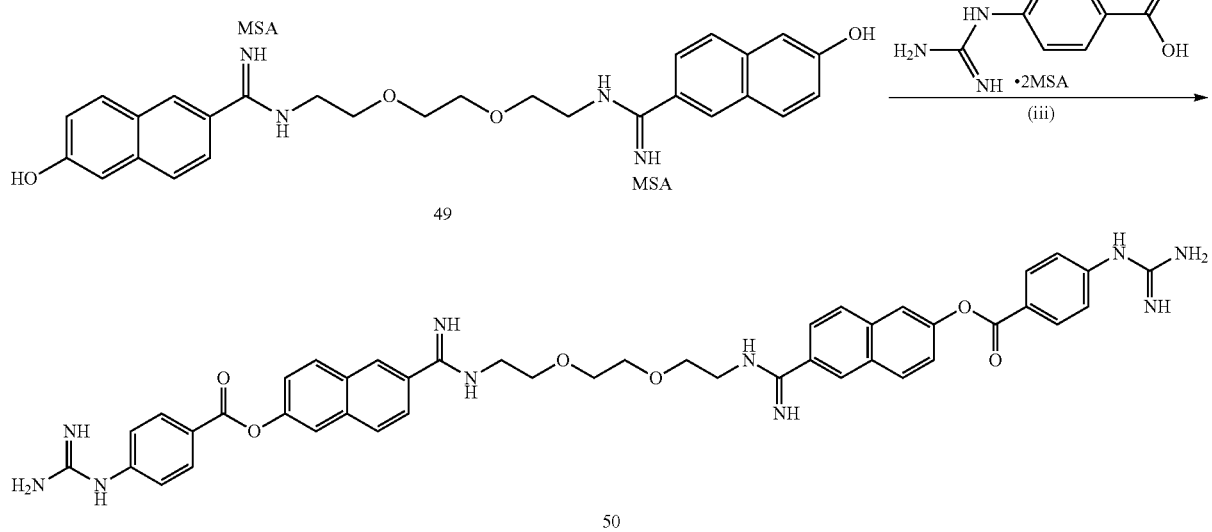

Reagents and conditions (i) Acetyl chloride, methanol, rt. (ii) a. Triethylamine, methanol, 0° C. to reflux, b. Methanesulfonic acid, methanol. (iii) DCC, 4-DMAP, pyridine, rt.

Acetyl chloride (23 mmol, 1.68 mL) was added to a stirred solution of 6-hydroxy-2-naphthonitrile (500 mg, 2.9 mmol) and methanol (36 mmol, 1.46 mL) in a sealed reaction flask. After the reaction was complete by LCMS, the volatiles were removed under reduced pressure, and washed with ether to afford the methyl-6-hydroxy-2-naphthimidate hydrochloride (48) (550 mg, 80%). $^1$HNMR (400 MHz: DMSO-$d_6$) δ: 4.32 (s, 3H), 7.27-7.28 (m, 2H), 7.89 (d, J=12 Hz, 1H), 7.97-8.02 (m, 2H), 8.80 (s, 1H), 10.63 (s, 1H), 11.56 (brs, 1H); Mass m/z 202 (M+H).

To a solution of methyl-6-hydroxy-2-naphthimidate hydrochloride 48 (160 mg, 0.34 mmol), and triethylamine (136 mg, 1.3 mmol) in methanol (5 mL) was added 2,2'-(ethane-1,2-diylbis(oxy))diethanamine (50 mg, 0.67 mmol) at 0° C. Then the reaction mixture was heated at reflux for 3 h. After completion of the reaction, solvents were removed by vacuum and the crude reaction mixture was washed with ether and acetone to afford intermediate compound 49 (150 mg, 54%). This precipitate was added to a cooled solution of methanol (10 mL) and methanesulfonic acid (59 mg, 0.61 mmol). After stirring for 1 h, the mixture was concentrated and washed with ether and acetone to afford N,N'-(2,2'-(ethane-1,2-diylbis(oxy))bis(ethane-2,1-diyl))bis(6-hydroxy-2-naphthimidamide)dimethanesulphonate (49).

$^1$HNMR (400 MHz: DMSO-$d_6$) δ 2.32 (s, 3H), 3.61-3.72 (m, 6H), 7.23-7.25 (m, 2H), 7.62 (dd, J=4.1, 8.1 Hz), 7.89 (d, J=8.1 Hz, 1H), 7.93-8.25 (m, 1H), 8.99 (s, 1H), 9.47 (s, 1H), 9.76 (s, 1H), 10.35 (s, 1H); Mass m/z 487 (M+H).

To a mixture of 4-guanidinobenzoic acid methanesulfonate (130 mg, 0.47 mmol), intermediate 49 (160 mg, 0.23 mmol), 4-dimethylaminopyridine (6 mg, 0.03 mmol) and DCC (146 mg, 0.70 mmol), was added dry pyridine (5 mL). This reaction mixture was stirred overnight at room temperature. After completion of the reaction, acetone was added to the reaction mixture and precipitate was filtered and purified by Prep HPLC using a 10-90% linear gradient of acetonitrile in water gradient (0.05% TFA modified mobile phase) to afford final compound (50) as off white solid after evaporation/lyophilization. $^1$H NMR (400 MHz, MeOD) δ 3.76 (t, J=4.1 Hz, 2H), 3.82 (s, 2H), 3.89 (t, J=4.1 Hz, 2H), 7.51 (d, J=8.5 Hz, 2H), 7.59 (dd, J=2.0 Hz, 1H), 7.77-7.79 (m, 1H), 7.92 (s, 1H), 8.10 (d, J=8.6 Hz, 1H), 8.16 (d, J=9.0 Hz, 1H), 8.33 (d, J=8.5 Hz, 2H), 8.41 (s, 1H); Mass m/z 809 (M+H).

Example 19

Synthesis of Compound 53

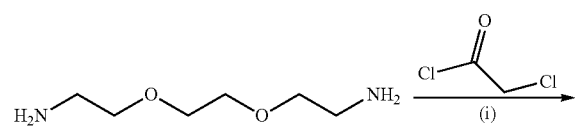

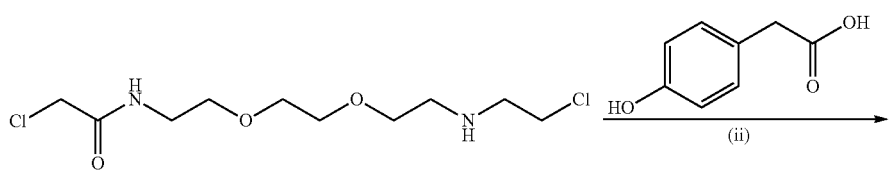

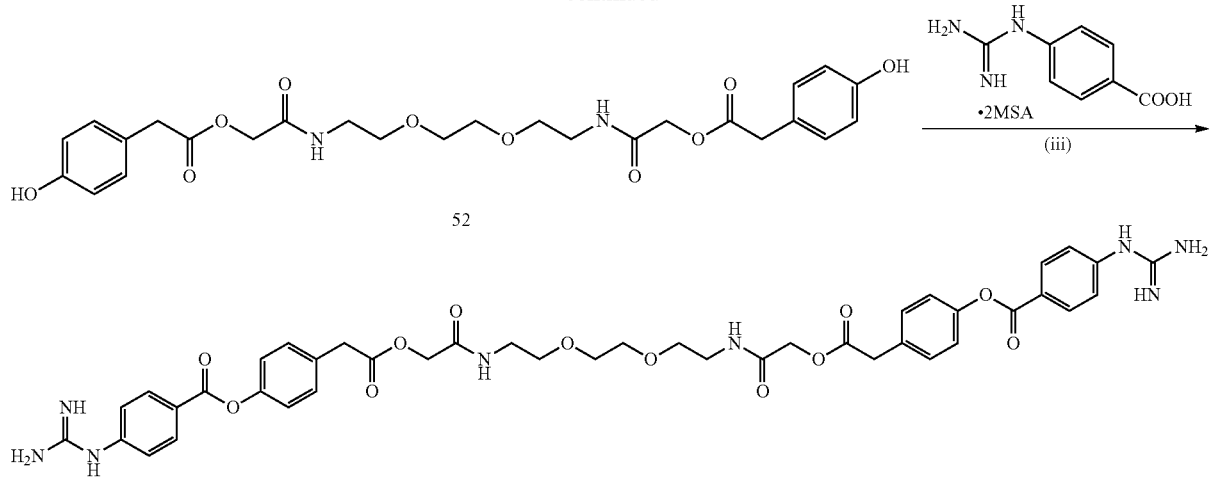

52

53

Reagents and conditions (i) Triethylamine, THF, -10 oC (ii) DIPEA, acetonitrile, 0 oC to reflux, 12h (iii) DCC, DMAP, pyridine.

To a solution of 2,2'-(ethane-1,2-diylbis(oxy))diethanamine (500 mg, 3.4 mmol), and triethylamine (1.4 g, 13.6 mmol) in dry THF (20 mL) under argon atmosphere at −10° C. was added chloroacetyl chloride (756 mg, 6.76 mmol) dropwise. This reaction mixture was stirred for 1 h, then concentrated under vacuum. The crude product was diluted with ethyl acetate and washed with water and brine to afford the title intermediate 51 (400 mg, 39%). $^1$HNMR (400 MHz: CDCl$_3$) δ: 3.52-3.56 (m, 2H), 3.61-3.64 (m, 2H), 3.67 (s, 2H), 4.09 (s, 2H), 7.03 (brs, 1H); Mass m/z 301 (M+H).

To a mixture of N,N'-(2,2'-(ethane-1,2-diylbis(oxy))bis (ethane-2,1-diyl))bis(2-chloroacetamide) (51) (200 mg, 0.67 mmol), and 4-hydroxyphenylacetic acid (203 mg, 1.43 mmol) in dry acetonitrile at 0° C. was added DIPEA (250 mg, 1.99 mmol). This reaction mixture was stirred for 1 h at 0° C., then refluxed for 12 h. The crude product was concentrated and purified by Prep HPLC to afford intermediate linker 52 as colorless liquid (150 mg, 42%). $^1$HNMR (400 MHz: CDCl$_3$) δ 3.46 (S, 2H), 3.60-3.73 (m, 6H), 4.61 (s, 2H), 6.81 (d, J=7.7 Hz, 2H), 7.18 (d, J=7.7 Hz, 2H); Mass m/z 533 (M+H).

To a mixture of 4-guanidinobenzoic acid methanesulfonate (103 mg, 0.37 mmol), linker 52 (100 mg, 0.19 mmol), DCC (111 mg, 0.54 mmol), and 4-dimethylaminopyridine (2.4 mg, 0.02 mmol) was added dry pyridine (5 mL). The reaction mixture was stirred overnight at room temperature. After completion of the reaction, acetone was added to the reaction mixture and precipitate was filtered and purified by Prep HPLC using a 10-90% linear gradient of acetonitrile in water gradient (0.05% TFA modified mobile phase) to afford final compound (53) as white solid after evaporation/lyophilization. $^1$H NMR (400 MHz, MeOD) δ 3.42-3.44 (m, 1H), 3.57 (t, J=5.4 Hz, 1H), 3.84 (s, 1H), 4.60 (s, 1H), 7.21 (d, J=8.4 Hz, 1H), 7.42 (d, J=8.4 Hz, 1H), 7.47 (d, J=8.5 Hz, 1H), 8.26 (d, J=8.6 Hz, 1H); Mass m/z 855 (M+H).

Example 20

Synthesis of Compound 57

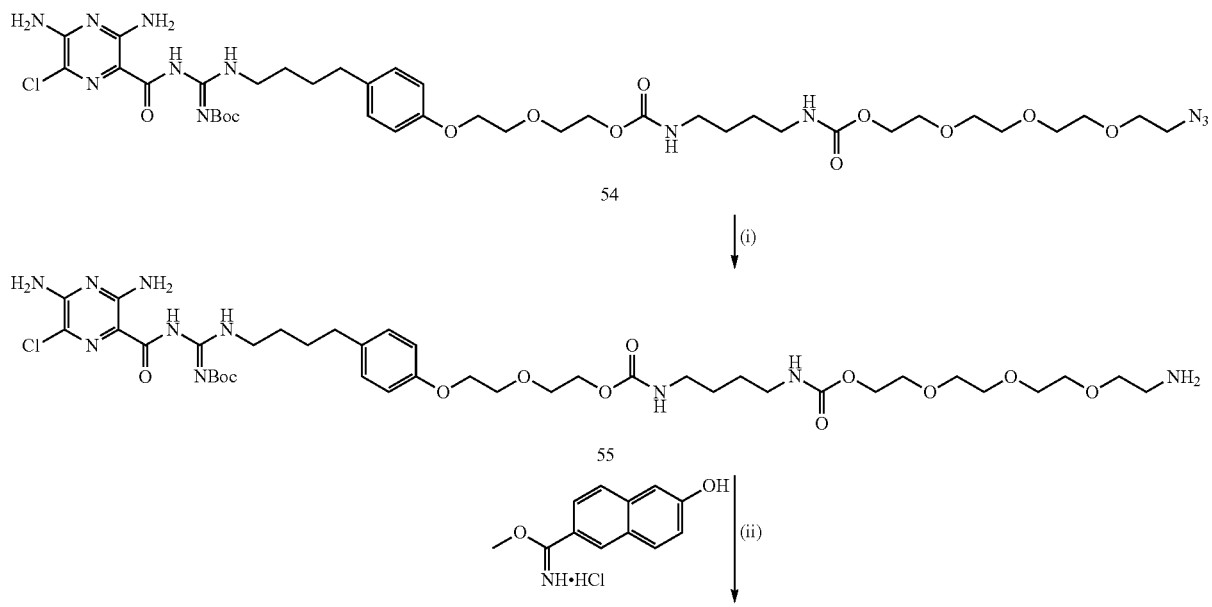

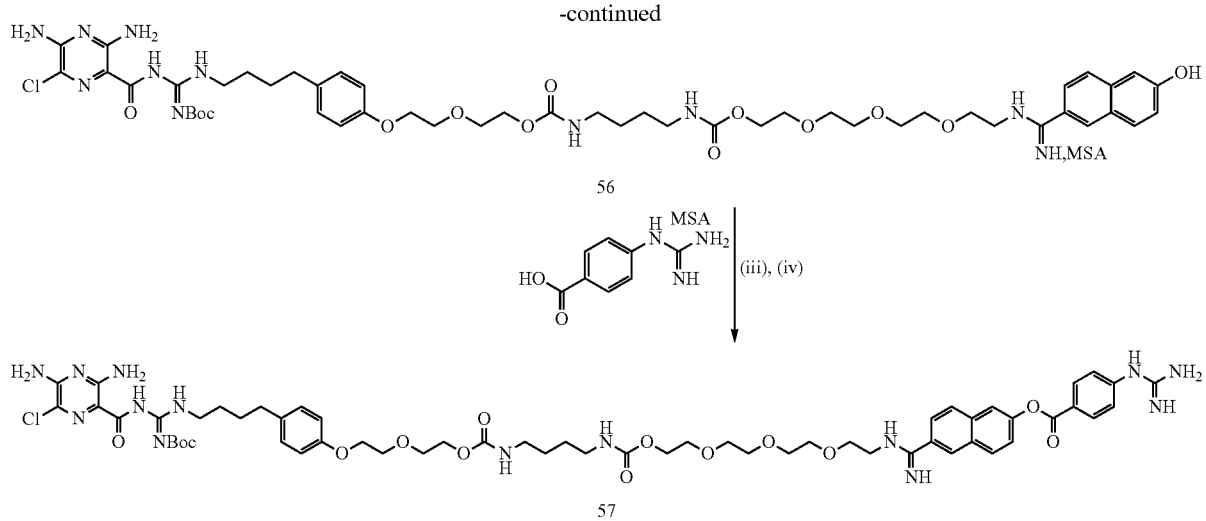

56

57

Reagents and conditions (i) Pd/C, H2, MeOH, rt (ii) triethylamine, methanol, reflux (iii) DCC, DMAP, pyridine (iv) 4M HCl in 1,4-Dioxane.

Intermediate 54 was prepared using a similar procedure as detailed in Example 7. Catalytic hydrogenation of 54 afforded amine intermediate 55. Compound 57 was prepared in two steps from compound 55 using a similar procedure as detailed in Example 18 and purified by Prep HPLC using a 10-90% gradient of acetonitrile in water gradient (0.05% TFA modified mobile phase). $^1$H NMR (400 MHz, MeOD) δ 1.29 (s, 3H), 1.45 (s, 4H), 1.69 (s, 3H), 2.62 (s, 2H), 3.06 (s, 4H), 3.61-3.71 (m, 13H), 3.81-3.84 (4H), 4.06-4.09 (m, 3H), 4.15 (s, 2H), 6.84 (d, J=8.1 Hz, 2H), 7.11 (d, J=8.2 Hz, 2H), 7.49 (d, J=8.8 Hz, 2H), 7.59 (d, J=8.8 Hz, 1H), 7.80 (d, J=8.4 Hz, 1H), 7.92 (s, 1H), 8.11 (d, J=8.6 Hz, 1H), 8.18 (d, J=8.9 Hz, 1H), 8.32 (d, J=8.3 Hz, 2H), 8.43 (s, 1H); MS m/z 1129 (M+H).

Example 21

Synthesis of Compound 62

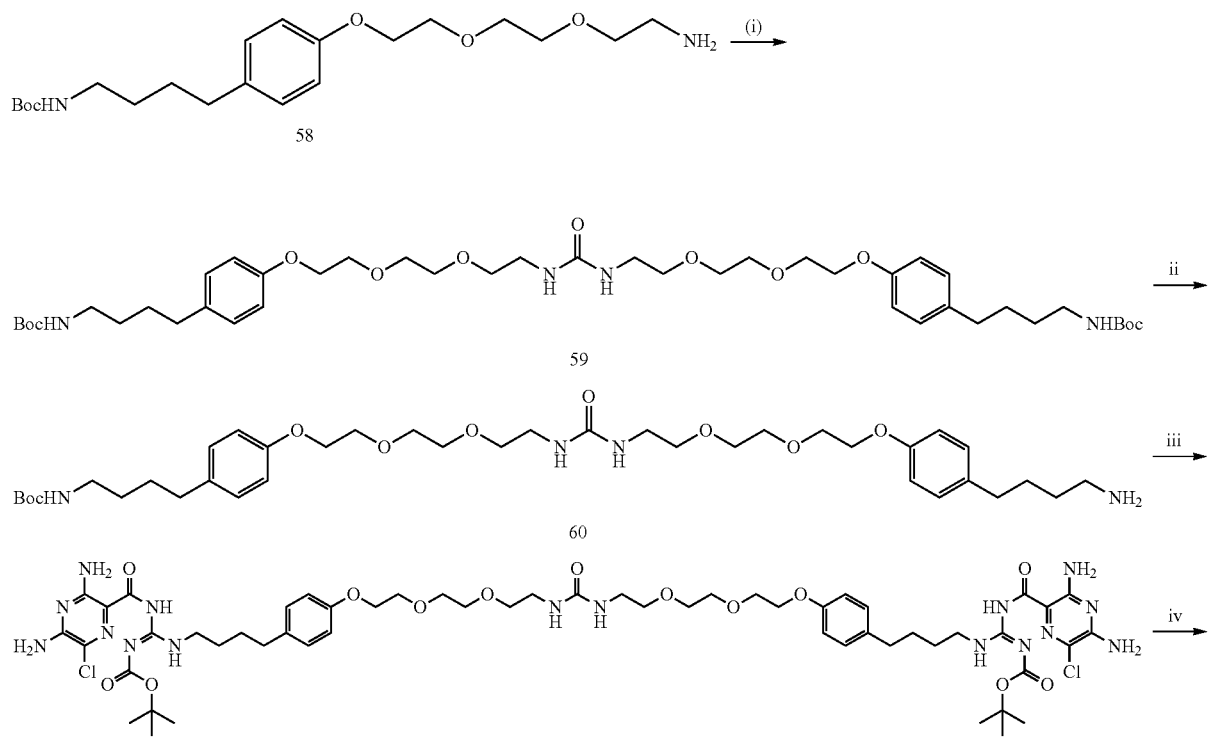

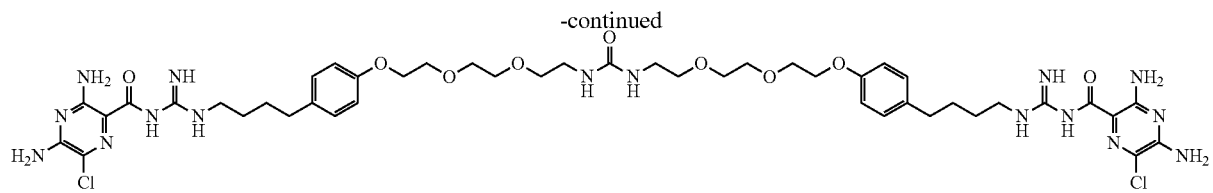

62

Reagents and conditions (i) 1,1′-Carbonyldiimidazole, DMF, rt, 12h; (ii) HCl, 1,4-dioxane; (iii) Tert-butyl-(3,5-diamino-6-chloropyrazine-2-carboxamido)(methylthio)methylenecarbamate, DIPEA, EtOH; (iv) HCl, 1,4-dioxane.

To a solution of tert-butyl-4-(4-(2-(2-(2-aminoethoxy)ethoxy)ethoxy)phenyl)butylcarbamate 58 (100 mg, 0.25 mmol) in DMF (5 mL) was added 1,1′-carbonyldiimidazole (20.5 mg, 0.12 mmol) and stirred at room temperature for 12 h. The product mixture was concentrated under high vacuum and crystallized by DCM/Hexenes to give linker 59. Mass m/z 815 (M+H).

Compound 62 was prepared in three steps from compound 59 using a similar procedure as detailed in Example 7. $^1$H NMR (400 MHz, MeOD) δ 1.71 (brs, 4H), 2.62-2.64 (m, 2H), 3.28 (t, J=5.2 Hz, 2H), 3.51 (t, J=5.2 Hz, 2H), 3.63 (d, J=4.4 Hz, 2H), 3.69-3.70 (m, 2H), 3.82 (t, J=4.2 Hz, 2H), 4.09 (t, J=4.5 Hz, 2H), 6.86 (d, J=8.3 Hz, 2H), 7.12 (d, J=8.3 Hz, 2H); Mass m/z 1043 (M+H).

Example 22

Synthesis of Compound 63

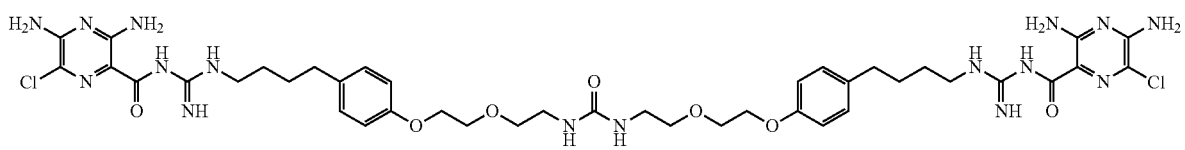

63

Compound 63 was prepared using a similar procedure as detailed in Example 21. $^1$H NMR (400 MHz, MeOD) δ 1.69 (s, 4H), 2.62 (s, 2H), 3.56 (t, J=5.2 Hz, 2H), 3.77-3.78 (m, 2H), 4.06 (brs, 2H), 6.84 (d, J=8.2 Hz), 7.11 (d, J=8.1 Hz, 2H); Mass m/z 955 (M+H).

Example 23

Synthesis of Compound 64

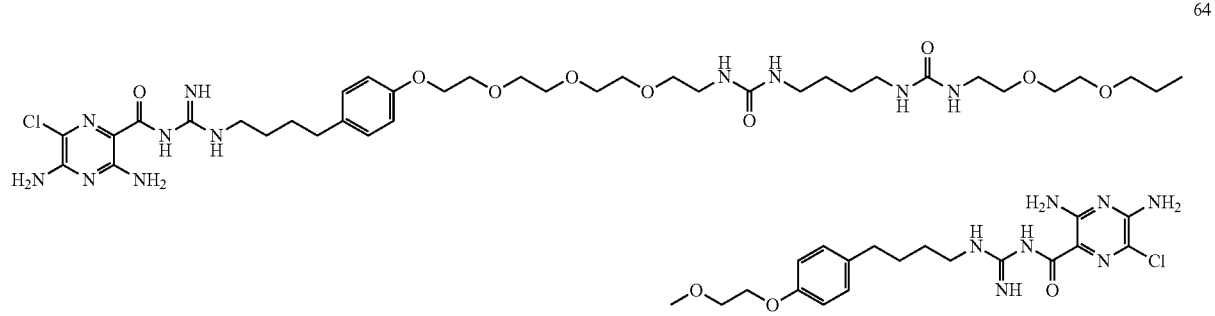

64

Compound 64 was prepared using a similar procedure as detailed in Example 12. $^1$H NMR (400 MHz, MeOD) δ 1.45 (s, 2H), 1.71 (brs, 4H), 2.62-2.64 (m, 2H), 3.09 (s, 2H), 3.27 (t, J=5.2 Hz, 2H), 3.50 (t, J=5.2 Hz, 2H), 3.61-3.72 (m, 9H), 3.84 (t, J=4.5 Hz, 2H), 4.09 (t, J=4.1 Hz, 2H), 6.86 (d, J=8.4 Hz, 2H), 7.12 (d, J=8.3 Hz, 2H); MS m/z 1245 (M+H).

Example 24

Synthesis of Compound 65

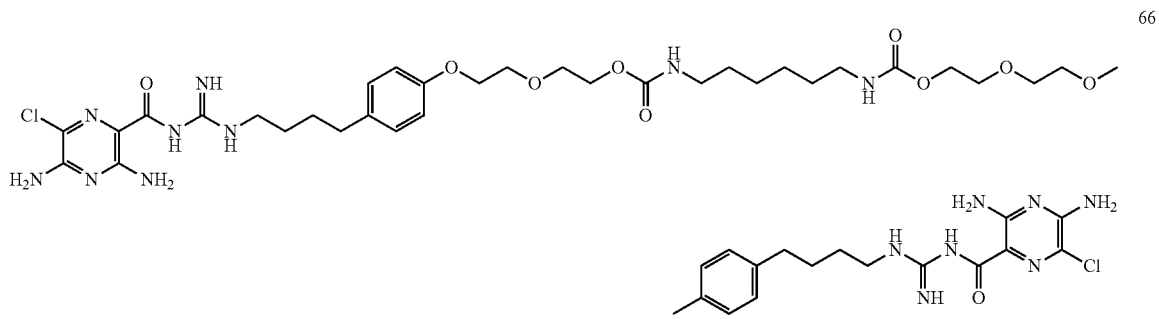

Compound 65 was prepared using a similar procedure as detailed in Example 7. $^1$H NMR (400 MHz, MeOD) δ 1.29 (brs, 2H), 1.44 (brs, 2H), 1.69 (s, 4H), 2.59-2.61 (m, 2H), 3.03-3.06 (m, 2H), 3.72-3.73 (m, 2H), 3.80-3.81 (m, 2H), 4.06 (s, 2H), 4.16-4.17 (m, 2H), 6.83 (d, J=8.2 Hz, 2H), 7.10 (d, J=8.3 Hz, 2H); MS m/z 1099 (M+H).

Example 25

Synthesis of Compound 66

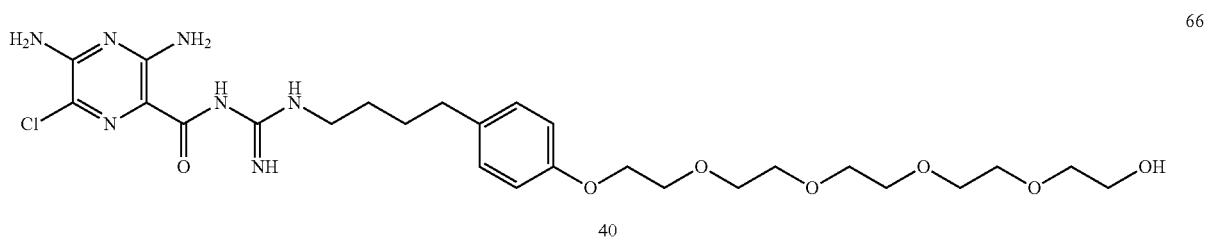

Compound 66 was prepared using similar procedures detailed herein. $^1$H NMR (400 MHz, MeOD) δ: 1.72 (brs, 4H), 2.63-2.65 (m, 2H), 3.56 (t, J=4.3 Hz, 2H), 3.66-3.71 (m, 14H), 3.84 (t, J=4.1 Hz, 2H), 4.10 (t, J=4.4 Hz, 2H), 6.85 (d, J=8.2 Hz, 2H), 7.14 (d, J=8.2 Hz, 2H); MS m/z 598 (M+H).

Example 26

Synthesis of Compound 67

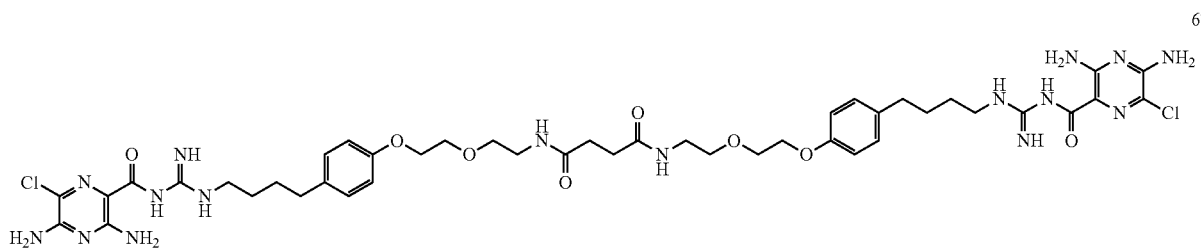 [SMILES: N=C(NCCCCc1ccc(OCCOCCNC(=O)CCC(=O)NCCOCCOc2ccc(CCCCNC(=N)NC(=O)c3nc(Cl)c(N)nc3N)cc2)cc1)NC(=O)c1nc(Cl)c(N)nc1N]

Compound 67 was prepared using similar procedures detailed herein. $^1$H NMR (400 MHz, MeOD) δ 1.59 (brs, 4H), 2.34 (s, 2H), 2.49-2.51 (m, 2H), 3.25-3.26 (m, 2H), 3.47 (t, J=5.4 Hz, 2H), 3.67 (t, J=4.5 Hz, 2H), 3.96 (t, J=4.1 Hz, 2H), 6.74 (d, J=8.4 Hz, 2H), 7.00 (d, J=8.3 Hz, 2H); MS m/z 1011 (M+H); Anal. ($C_{44}H_{60}Cl_2N_{16}O_8 \cdot 4CF_3COOH$) Calcd. C, 42.54; H, 4.39; N, 15.53. Found C, 41.26; H, 4.72; N, 14.92.

Example 27

Synthesis of Compound 68

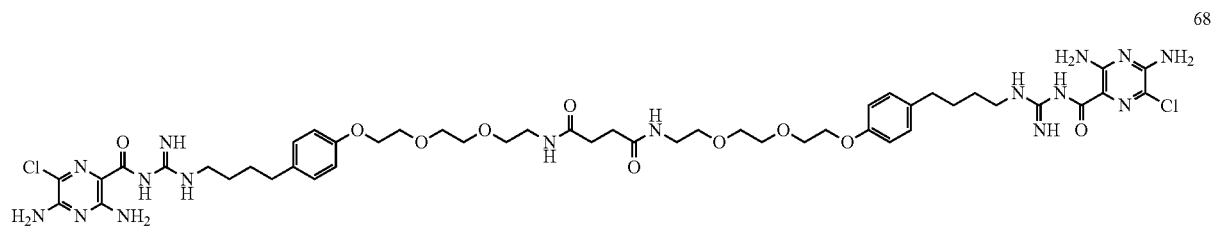 [SMILES: N=C(NCCCCc1ccc(OCCOCCOCCNC(=O)CCC(=O)NCCOCCOCCOc2ccc(CCCCNC(=N)NC(=O)c3nc(Cl)c(N)nc3N)cc2)cc1)NC(=O)c1nc(Cl)c(N)nc1N]

Compound 68 was prepared using similar procedures detailed herein. $^1$H NMR (400 MHz, MeOD) δ 1.71 (brs, 4H), 2.46 (s, 2H), 2.64 (s, 2H), 3.52-3.54 (m, 2H), 3.64 (s, 2H), 3.71 (s, 2H), 3.84 (s, 2H), 4.10 (s, 2H), 6.86 (d, J=7.8 Hz, 2H), 7.13 (d, J=7.8 Hz, 2H); MS m/z 1099 (M+H); Anal. ($C_{48}H_{68}Cl_2N_{16}O_{10} \cdot 2H_2O$) Calcd. C, 50.43; H, 6.16; N, 21.38. Found C, 50.10; H, 6.06; N, 18.94.

Example 28

Synthesis of Compound 69

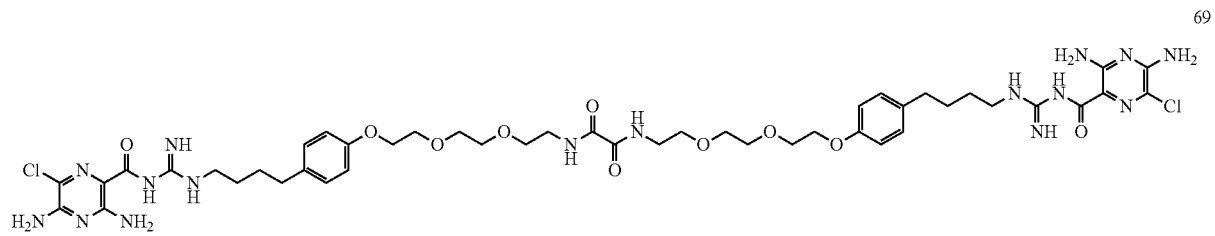 [SMILES: N=C(NCCCCc1ccc(OCCOCCOCCNC(=O)C(=O)NCCOCCOCCOc2ccc(CCCCNC(=N)NC(=O)c3nc(Cl)c(N)nc3N)cc2)cc1)NC(=O)c1nc(Cl)c(N)nc1N]

Compound 69 was prepared using similar procedures detailed herein. $^1$H NMR (400 MHz, MeOD) δ 1.59 (brs, 4H), 2.52 (s, 2H), 3.32 (d, J=5.5 Hz, 2H), 3.48 (t, J=5.4 Hz, 2H), 3.52 (d, J=4.9 Hz, 2H), 3.58 (d, J=4.9 Hz, 2H), 3.71 (t, J=4.5 Hz, 2H), 3.96-3.97 (m, 2H), 6.74 (d, J=8.3 Hz, 2H), 7.00 (d, J=8.2 Hz, 2H); MS m/z 1071 (M+H); Anal. ($C_{46}H_{64}Cl_2N_{16}O_{10} \cdot 2H_2O$) Calcd. C, 49.86; H, 6.19; N, 20.23. Found C, 49.91; H, 5.96; N, 19.96.

Example 29

Synthesis of Compounds 70-79

The following compounds may be prepared using analogous procedures as described in Examples 1-28.

| Cpd | Structure |
|---|---|
| 70 | 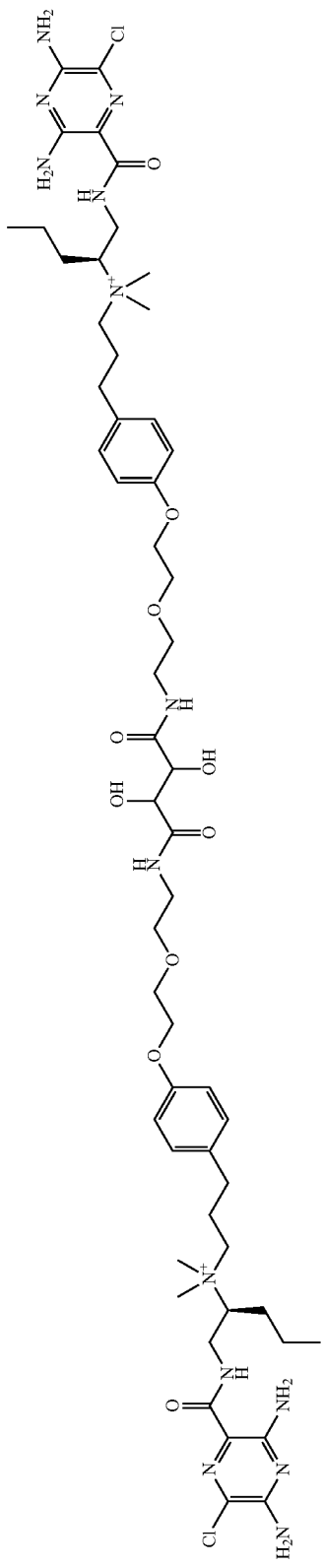 |
| 71 | 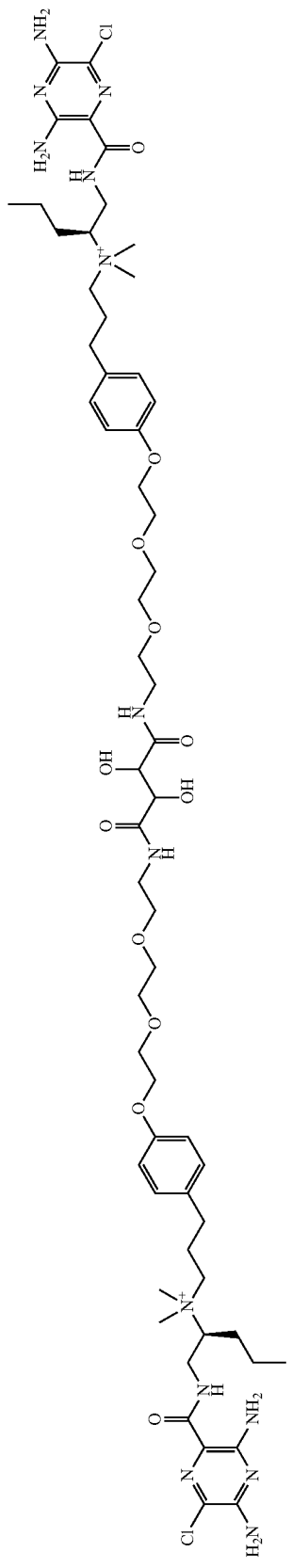 |
| 72 | 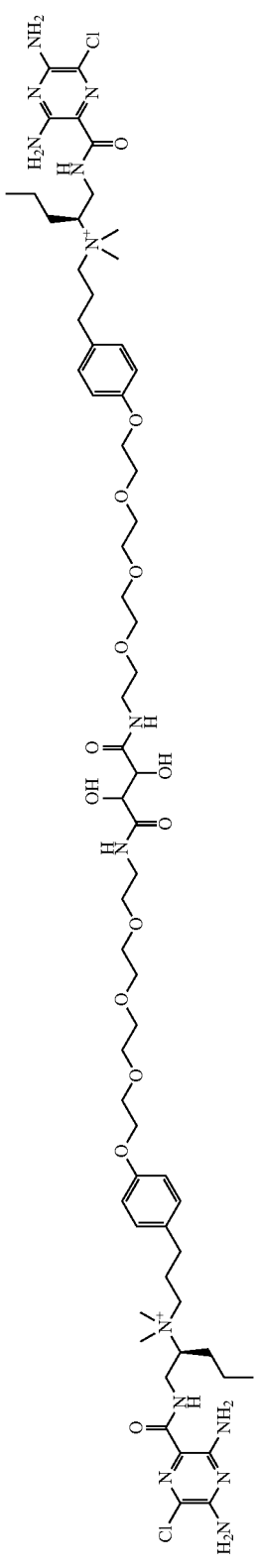 |

-continued

| Cpd | Structure |
|---|---|
| 73 | 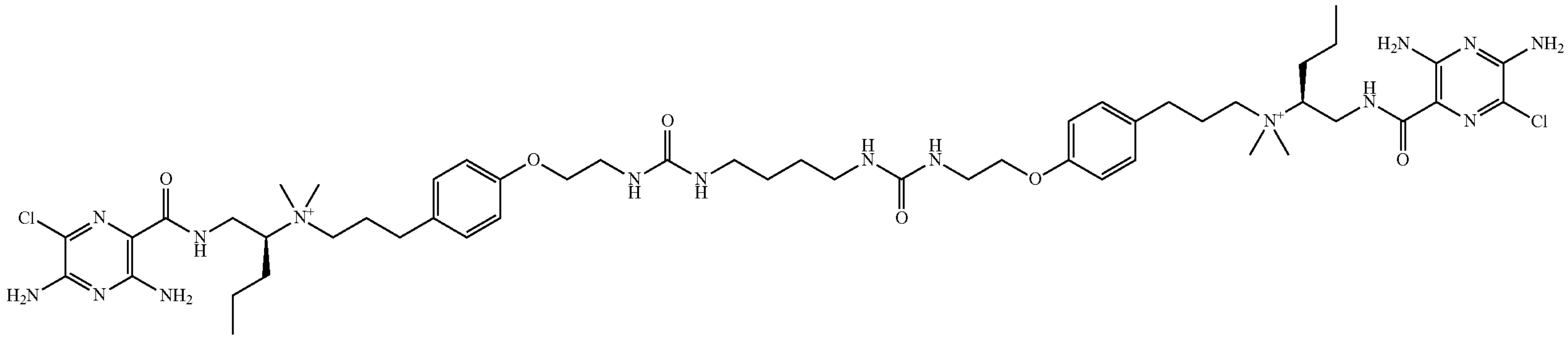 [SMILES: CCC[C@@H](CNC(=O)c1nc(Cl)c(N)nc1N)[N+](C)(C)CCCc1ccc(OCCNC(=O)NCCCCNC(=O)NCCOc2ccc(CCC[N+](C)(C)[C@@H](CCC)CNC(=O)c3nc(Cl)c(N)nc3N)cc2)cc1] |
| 74 | 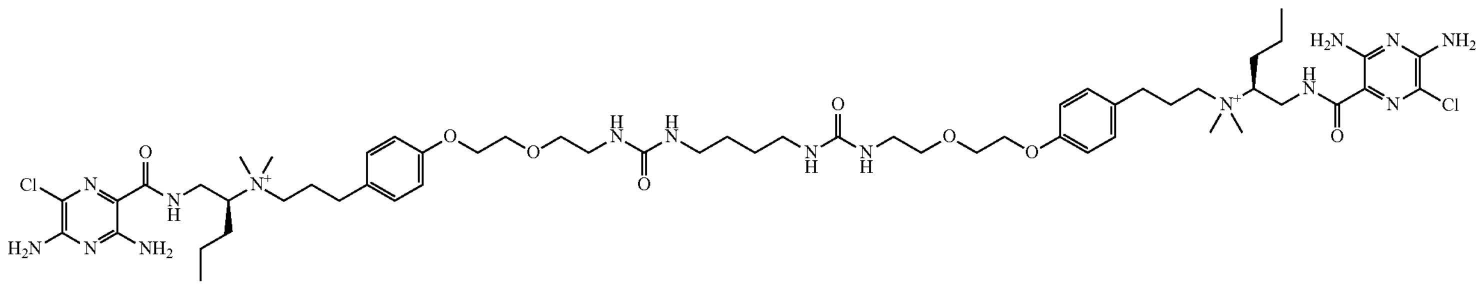 [SMILES: CCC[C@@H](CNC(=O)c1nc(Cl)c(N)nc1N)[N+](C)(C)CCCc1ccc(OCCOCCNC(=O)NCCCCNC(=O)NCCOCCOc2ccc(CCC[N+](C)(C)[C@@H](CCC)CNC(=O)c3nc(Cl)c(N)nc3N)cc2)cc1] |
| 75 | 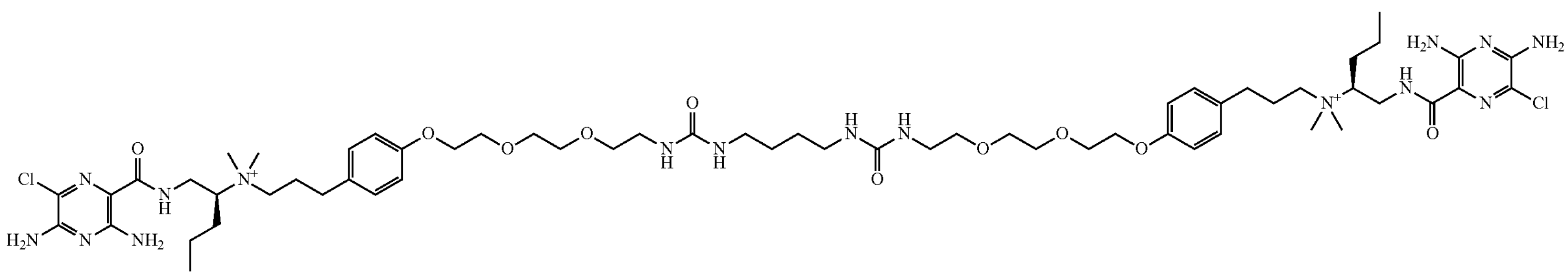 [SMILES: CCC[C@@H](CNC(=O)c1nc(Cl)c(N)nc1N)[N+](C)(C)CCCc1ccc(OCCOCCOCCNC(=O)NCCCCNC(=O)NCCOCCOCCOc2ccc(CCC[N+](C)(C)[C@@H](CCC)CNC(=O)c3nc(Cl)c(N)nc3N)cc2)cc1] |

| Cpd | Structure |
|---|---|
| 76 | 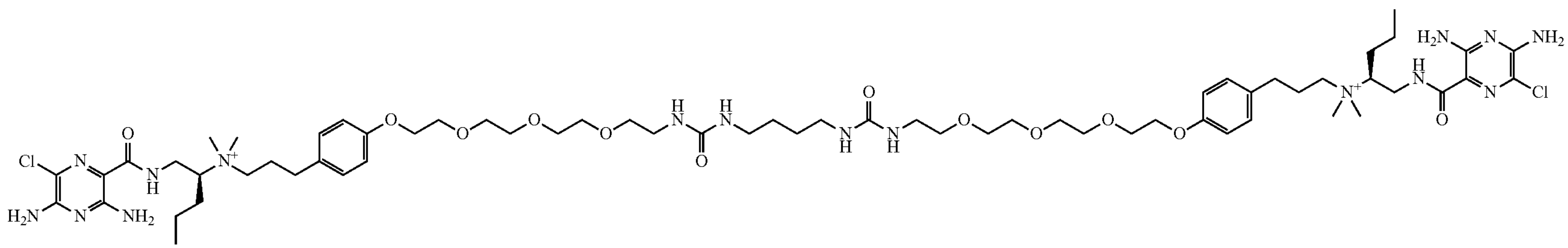 [SMILES: CCC[C@@H](CNC(=O)c1nc(Cl)c(N)nc1N)[N+](C)(C)CCCc1ccc(OCCOCCOCCOCCNC(=O)NCCCCNC(=O)NCCOCCOCCOCCOc2ccc(CCC[N+](C)(C)[C@@H](CCC)CNC(=O)c3nc(Cl)c(N)nc3N)cc2)cc1] |
| 77 | 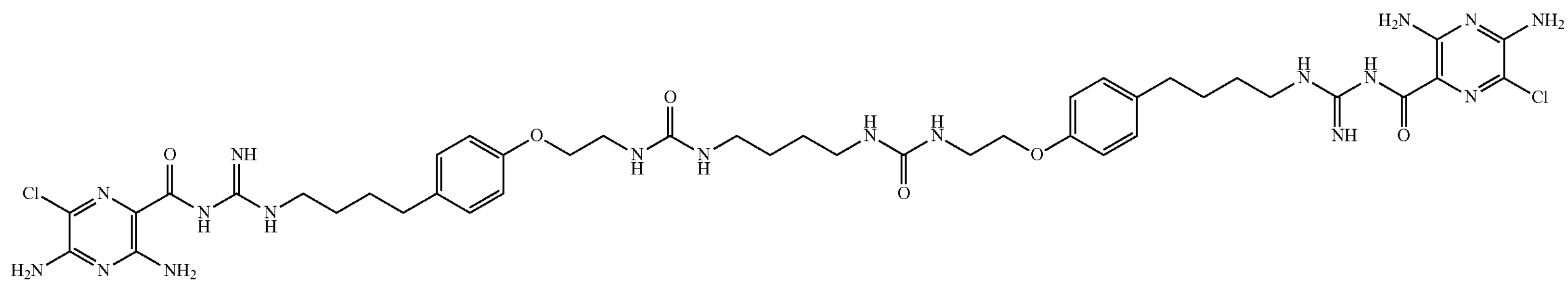 [SMILES: N=C(NCCCCc1ccc(OCCNC(=O)NCCCCNC(=O)NCCOc2ccc(CCCCNC(=N)NC(=O)c3nc(Cl)c(N)nc3N)cc2)cc1)NC(=O)c1nc(Cl)c(N)nc1N] |
| 78 | 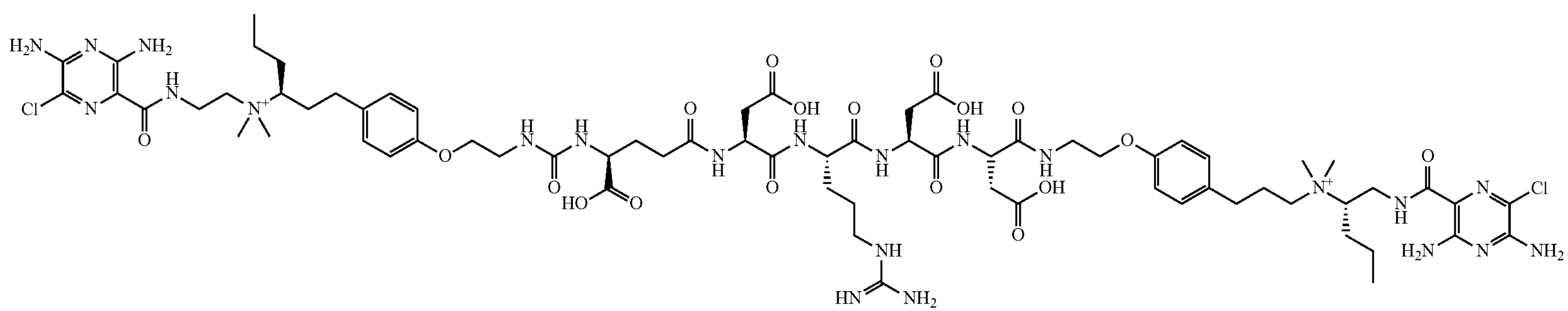 |

| Cpd | Structure |
|---|---|
| 79 | 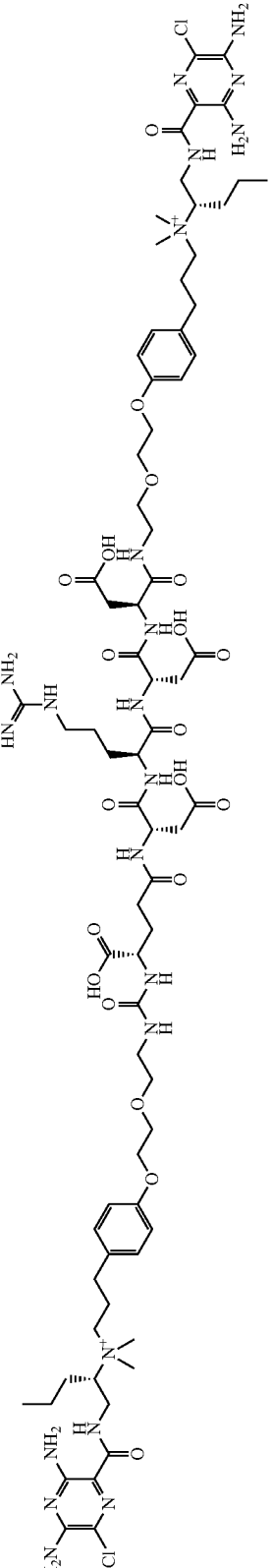 |

Example 30

In Vivo Assay

Cystic fibrosis (CF) and chronic obstructive pulmonary disease (COPD) is dysregulated clearance of mucus across the cell layers lining the respiratory tract. A therapeutic strategy to treat these diseases is to inhibit these channels or the regulators of these channels in an effort to correct this mucus clearance defect. Potential difference is used in the clinic as a diagnostic tool for cystic fibrosis sufferers and for clinical trials. Small molecule inhibitors of these targets will enhance mucociliary clearance and thereby improve lung function and reduce the rate of exacerbations in cystic fibrosis (CF) and chronic obstructive pulmonary disease (COPD) patients. The guinea pig, unlike other rodents, has a lung structure which is roughly analogous to the human lung. For this reason, in terms of rodent models of lung function the guinea pig is often the model of choice for respiratory disease models including asthma, COPD and respiratory distress syndrome.

Preparation of Agar Bridges

Agar (3.5%) was dissolved in Hank's buffered salt solution (pH 7.4, 280-305 mosmkg_1H$_2$O) by heating in a water bath at 100° C. A 30-40 cm length of polyethylene tubing, of which one end was bevelled at an angle of 20-60°, was then filled with the agar ensuring no air bubbles were formed or trapped within the tubing. The beveled tip of the tube was then dipped in the liquid agar, creating a small bulge. The exploring and reference electrodes constructed with the Hank's buffered salt solution/agar bridge were linked to a calomel half cell by immersion in 1M KCl.

Intra-Tracheal Dosing:

Guinea pigs received a single dose of either the test article or vehicle instilled directly into the trachea. The animal was placed under short-term anesthesia using an inhaled isoflurane/nitrous oxide (N$_2$O) 1:1 mixture (level 5/optimal for ~10 sec.; 3.5/2 for 5 min.). At this suitable depth of anesthesia (loss of pedal and blink reflex), a single dose of either the test article, vehicle and/or positive control was instilled directly into the trachea. This was accomplished by very delicately inserted the 3", 18 guage feeding tube into the trachea to preserve the potential difference of the mucosa. The guinea pig was allowed to recovered immediately; at times with the aid of supplemental O$_2$. The animal was observed for adverse behavioral or clinical signs such as motor activity, hunched posture, labored breathing, cyanosis or other signs of possible pain or distress during the procedure. If there was apparent toxicity, animals were euthanized immediately and all observation was appropriately documented. As the animal was anesthetized during this treatment, no local anesthesia was necessary and there was no need to use a laryngoscope.

Figure 2:
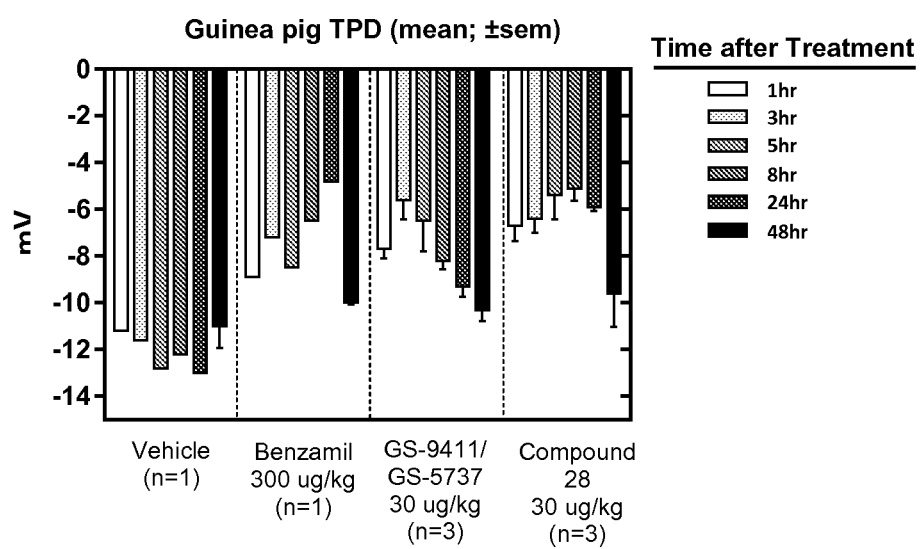
FIG. 2 shows the time course assessment of compound 28 versus controls.

Surgical Preparation:

After 3 hr the GP was again anesthetized and tracheal potential difference was measured. 30 minutes prior to the 3 hr post dosing surgery each guinea pig received a dose of 0.4 mL of Midazolam-5 mg/mL, intra-peritoneal (i.p.) injection followed 25 minutes later with a 1 mL/kg of 50 mg/kg ketamine/6.5 mg/kg xylazine i.p. injection (previously prepared with 100 mg/mL ketamine and 25 mg/mL xylazine in Sterile Water for Injection USP mixed at 2:1:1 respectively). 5 minutes after the last injection (exactly 3 hr after drug treatment) the animal was placed supine and the throat area is shaved. The trachea was exposed and visualized near the sternum using minimal blunt dissection. A lateral incision was made between the cartilaginous rings of the trachea close to the sternum. The beveled (distal) end of an exploring electrode was gently inserted into the lumen of the trachea moving in the direction towards the larynx, ensuring that spontaneous respiration was still possible. The beveled end of the reference electrode was positioned near the trachea in electrical contact with the flesh of the throat. A small volume of HBSS was applied into this region to ensure a good electrical contact. Potential difference was measured using a high impedance voltmeter (IsoMil) (5-0.5 cm increment measurement for verification—but only the initial placement value is recorded). The animal was terminated immediately after this procedure while still under anesthesia with an intra-cardiac dose of 0.5 mL of Euthasol. If at any time during this procedure the animal became cyanotic or exhibits labored breathing the test ends and the animal was immediately euthanized. Tracheal potential difference (TPD) data is shown in Tables 1 and 2. Time course assessment of compound 28 vs. controls is shown in Table 3 and FIG. 2.

TABLE 1

| Compound | Dose ug/kg | TPD (mV) | ±sem |
|---|---|---|---|
| 29 | 300 | −7.70 | 0.19 |
| 28 | 300 | −4.00 | 0.12 |
| 31 | 300 | −7.60 | 1.50 |
| 30 | 300 | −6.50 | 0.22 |
| 50 | 300 | −6.20 | 0.19 |
| 38 | 300 | −4.60 | 0.70 |
| 40 | 300 | −4.90 | 0.74 |
| 37 | 300 | −5.50 | 2.18 |
| 37 | 30 | −7.50 | 0.98 |
| 32 | 300 | −9.50 | 0.80 |
| 16 | 30 | −6.30 | 0.36 |
| 18 | 30 | −8.10 | 0.57 |
| 66 | 30 | −7.80 | 0.70 |
| 17 | 30 | −6.6 | 0.52 |
| 53 | 30 | −9.3 | 0.04 |
| 57 | 30 | −7.5 | 0.55 |
| 64 | 30 | −6.70 | 0.04 |
| 47 | 30 | −8.20 | 1.00 |
| 46 | 30 | −7.30 | 0.19 |
| 65 | 30 | −7.70 | 0.87 |
| 67 | 0.2 | −7.0 | 0.54 |
| 68 | 0.2 | −6.9 | 0.07 |
| 69 | 30 | −6.3 | 0.18 |

TABLE 2

| Compound | Dose ug/kg | TPD (mV) | ±sem |
|---|---|---|---|
| Vehicle | | −12.4 | 0.27 |
| Benzamil | 300 | −6.2 | 0.73 |
| PA-552 | 300 | −5.6 | 0.45 |
| NVS quat ammonium | 300 | −6.1 | 0.15 |
| GS-9411/GS-5737 | 300 | −4.1 | 0.2 |
| Camostat | 300 | −4.9 | 0.14 |

Mean tracheal potential difference (TPD) values ±sem obtained in groups of guinea-pigs dosed with either vehicle (0.2 mL of 95%-5% dextrose/5% Absolute EtOH) or test articles by it instillation.
Student's tTest Compound treated vs Vehicle.
*** = p < 0.001
a - Mean of combined vehicle values to which test articles were compared.

TABLE 3

| Treatment | Dose (µg/kg) | 1 hr | 3 hr | 5 hr | 8 hr | 24 hr | 48 hr |
|---|---|---|---|---|---|---|---|
| Vehicle | — | −11.2 (1) | −11.6 (1) | −12.8 (1) | −12.2 (1) | −13.0 (1) | −11.0 ± 0.92 (2) |
| Benzamil | 300 | −8.9 (1) | −7.2 (1) | −8.5 (1) | −6.5 (1) | −4.8 (1) | −10.0 ± 0.07 (2) |
| (GS-9411) | 30 | −7.7 ± 0.41 (3) | −5.6 ± 0.82 (3) | −6.5 ± 1.28 (3) | −8.2 ± 0.36 (3) | −9.3 ± 0.43 (3) | −10.3 ± 0.47 (3) |
| Compound 28 | 30 | −6.7 ± 0.65 (3) | −6.4 ± 0.60 (3) | −5.4 ± 1.03 (3) | −5.1 ± 0.54 (3) | −5.9 ± 0.18 (3) | −9.6 ± 1.43 (3) |

Mean tracheal potential difference values ± sem and (N) obtained in groups of guinea-pigs dosed with either vehicle (0.2 mL of 95%-5% dextrose/5% Absolute EtOH) or test articles by i.t. instillation.

Example 31

Comparison of Systemic Exposure of a Monomeric Compound and a Compound of Formula (I), (Ia), (Ib), (II), (III), or (IV)

A comparison of systemic (plasma exposure) of monomeric compound GS-9411 and dimeric compound 28 after intratracheal dosing was performed (at 1 mg/kg single dose). Compound 28 demonstrated a 20× lower Cmax (maximal concentration) and 5-fold lower AUC (total area under the curve). After inhalation in a Phase 1 clinical trial in human, GS-9411 has demonstrated similar pharmacokinetics as in the intratracheal guinea pig model (O'Riordan, et al. Journal of Aerosol Medicine and Pulmonary Drug Delivery 2013, 26 (0), 1-9).

Example 32

Phase I/II Study of a Compound of Formula (I), (Ia), (Ib), (II), (III), or (IV) by Inhalation for the Treatment of Patients with Cystic Fibrosis Purpose:

The purpose of this research study is to evaluate the safety and effectiveness of compounds presented herein on lung function when given to patients with cystic fibrosis by inhalation.

Patients:

Eligible subjects will be male and female 12 years and older.

Criteria:

Inclusion Criteria:

At least 12 years of age;

Must be receiving ongoing chronic treatment with TOBI (inhaled tobramycin) OR not receiving ongoing chronic treatment with TOBI and no use of TOBI or other inhaled antibiotic within 4 weeks prior to study drug administration;

Other specific diagnostic indicators of CF and other factors must meet minimum requirements.

Study Design:

This is a randomized, safety/efficacy trial with a compound of Formula (I), (Ia), (Ib), (II), (III), or (IV) (500 or 1000 mcg, inhalation, 3× per week) for the treatment of cystic fibrosis.

Primary Outcome Measures

Change in FEV1, sputum bacterial density after 12 weeks of treatment.

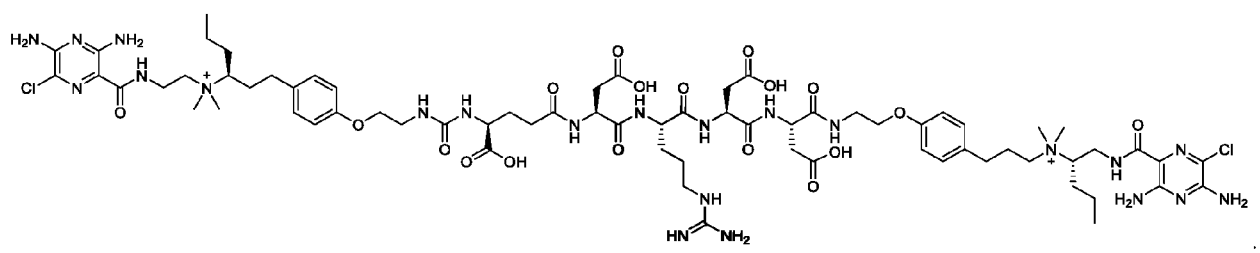

The invention claimed is:

1. A compound of Formula (I), a pharmaceutically acceptable salt, solvate, polymorph, prodrug, metabolite, deuteride, N-oxide, stereoisomer, or isomer thereof:

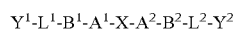

Formula (I);

wherein:

$A^1$ and $A^2$ are independently selected from:

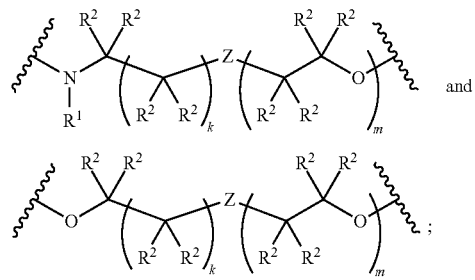

and $B^1$ and $B^2$ are independently selected from:

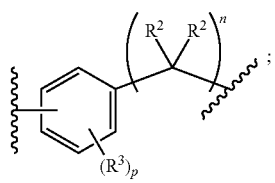

$L^1$ and $L^2$ are independently selected from:

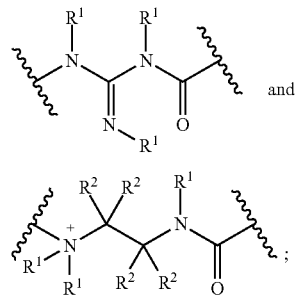

and $Y^1$ and $Y^2$ are independently selected from:

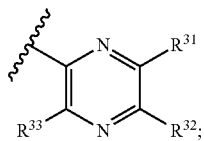

X is —C(O)—, —C(O)C(O)—

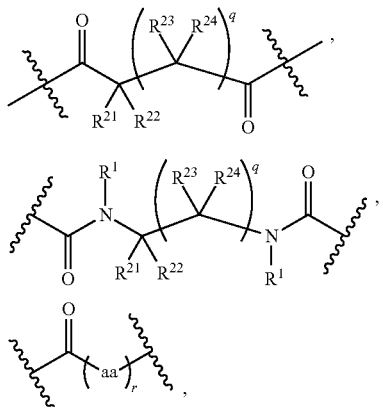

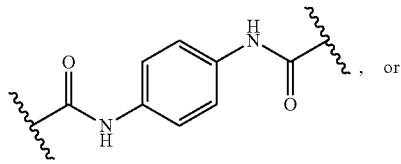

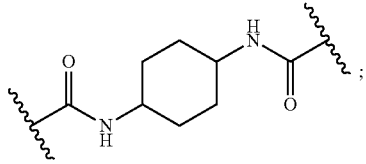

Z is O or $CR^2R^2$;
aa is

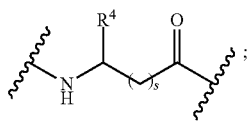

each $R^1$ is independently selected from H, alkyl, haloalkyl, arylalkyl, and heteroarylalkyl;

each $R^2$ is independently selected from H, halo, —CN, —SR$^1$, alkyl, cycloalkyl, haloalkyl, —OR$^1$, —CO$_2$R$^1$, and -(alkylene)CO$_2$R$^1$);

each $R^3$ is independently selected from halo, alkyl, —CN, haloalkyl, —OR$^1$, and —NR$^1$R$^1$;

each $R^4$ is independently selected from —CO$_2$R$^1$, -(alkylene)-(CO$_2$R$^1$), hydroxyalkyl, -(alkylene)(S(O)$_t$)(alkyl), -(alkylene)(NR$^5$R$^5$), and

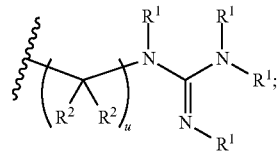

each $R^5$ is independently selected from H, alkyl, haloalkyl, arylalkyl, heteroarylalkyl, aryl, and heteroaryl;

each $R^{21}$, $R^{22}$, $R^{23}$, and $R^{24}$ are independently selected from H, halo, —CN, —SR$^1$, alkyl, cycloalkyl, haloalkyl, —NR$^1$R$^1$, and —OR$^1$;

$R^{31}$, $R^{32}$, and $R^{33}$ are independently selected from halo, alkyl, —CN, haloalkyl, —OR$^1$, and —NR$^1$R$^1$;

each k is independently selected from 1, 2, 3, 4, 5, 6, 7, 8, 9, and 10;

each m is independently selected from 0, 1, 2, 3, 4, 5, 6, 7, 8, 9, and 10;

each n is independently selected from 1, 2, 3, 4, 5, 6, 7, 8, 9, and 10;

each p is independently selected from 0, 1, 2, 3, and 4;

q is 1, 2, 3, 4, 5, 6, 7, 8, 9, or 10;

r is 3, 4, 5, 6, or 7;

each s is independently selected from 0, 1, 2, 3, and 4;

each t is independently selected from 0, 1, and 2; and each u is independently selected from 1, 2, 3, 4, 5, 6, 7, 8, 9, and 10.

2. The compound of claim 1 wherein $Y^1$ and $Y^2$ are both

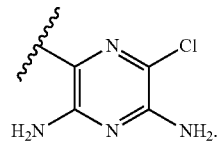

3. The compound of claim 2 wherein $B^1$ and $B^2$ are both

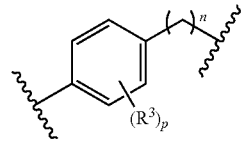

4. The compound of claim 3 wherein n is 1, 2, 3, 4, or 5.
5. The compound of claim 4 wherein n is 3 or 4.
6. The compound of claim 5 wherein p is 0.
7. The compound of claim 6 wherein $A^1$ and $A^2$ are both

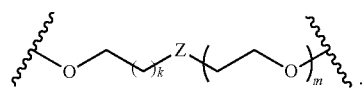

8. The compound of claim 7 wherein Z is O.
9. The compound of claim 8 wherein k is 1.

10. The compound of claim 9 wherein each m is independently 0, 1, 2, or 3.
11. The compound of claim 10 wherein $L^1$ and $L^2$ are both
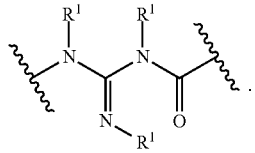
12. The compound of claim 11 wherein $L^1$ and $L^2$ are both
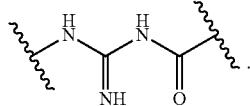 [SMILES: *NC(=N)NC(*)=O]
13. The compound of claim 12 wherein X is
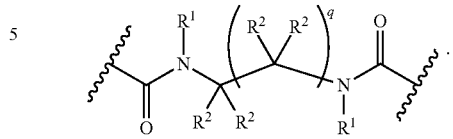
14. The compound of claim 13 wherein X is
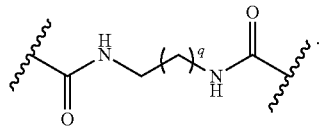
15. The compound of claim 14 wherein q is 3.
16. The compound of claim 1 wherein the compound is selected from:

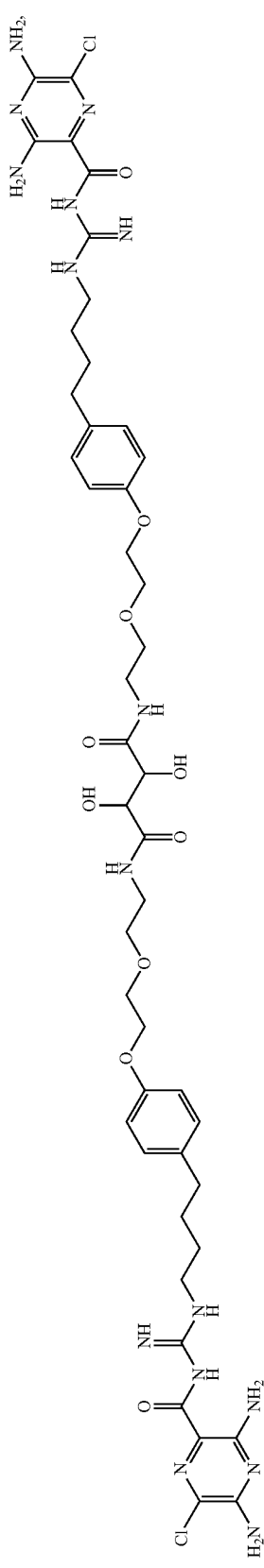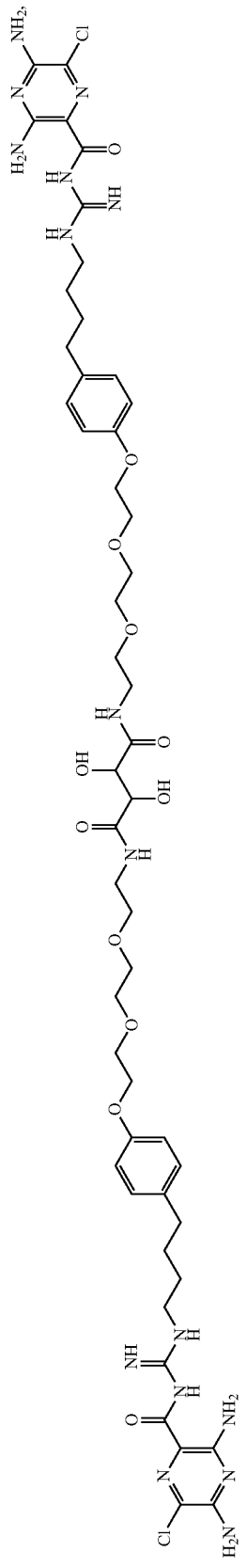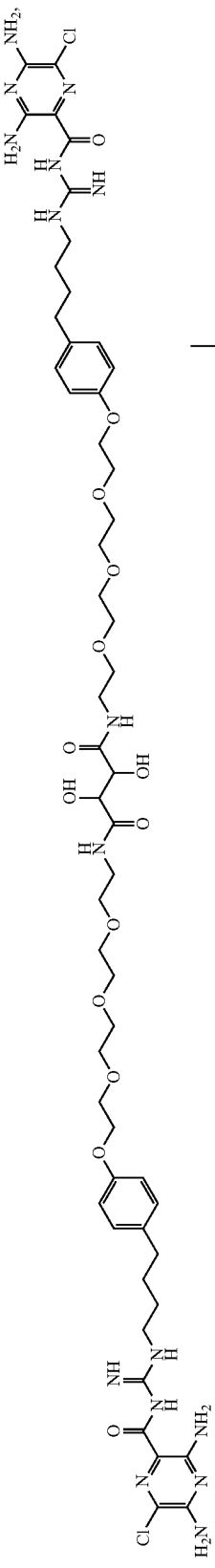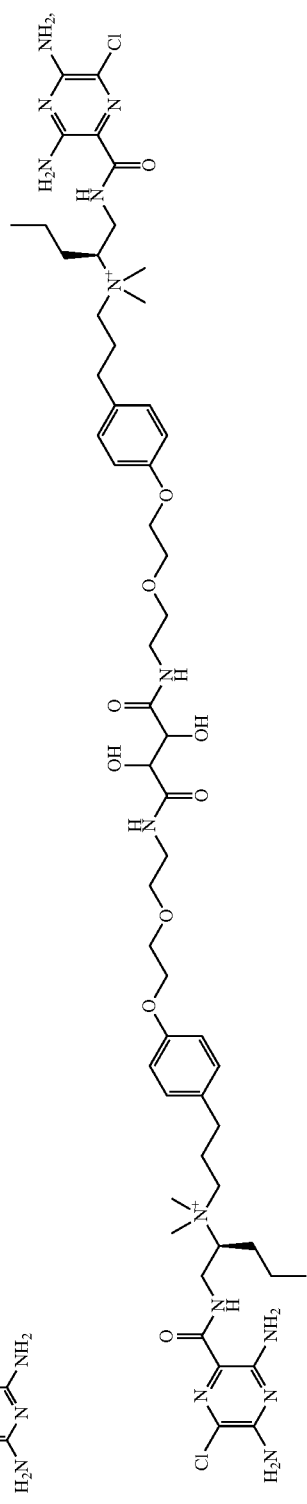

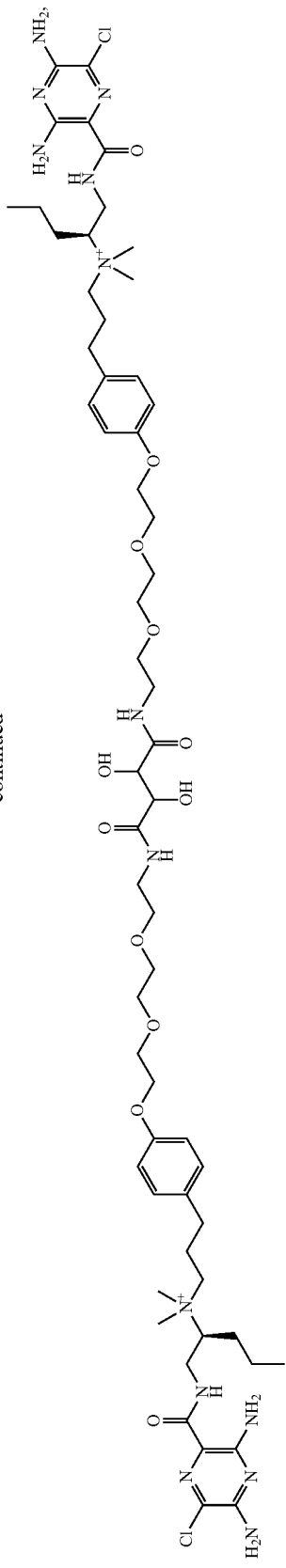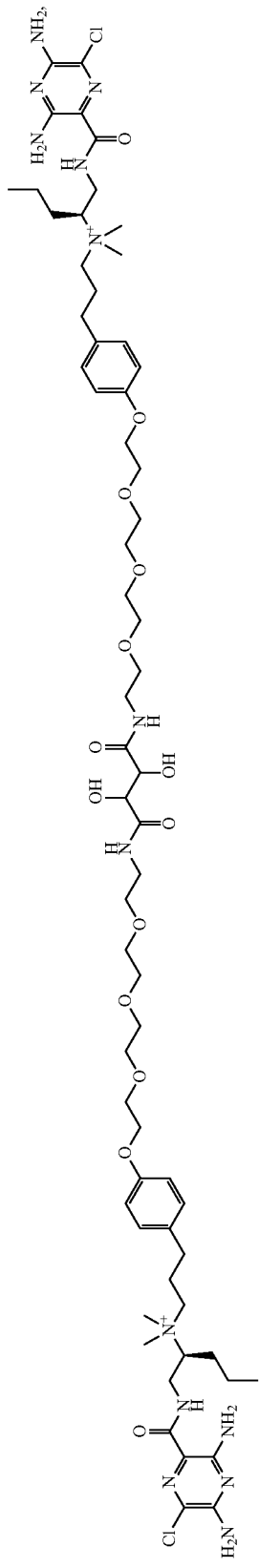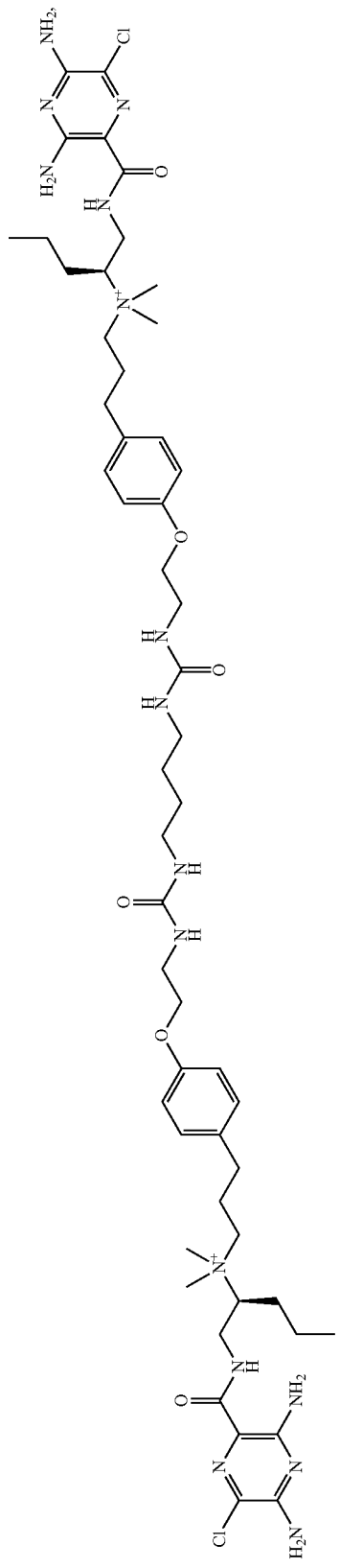

-continued
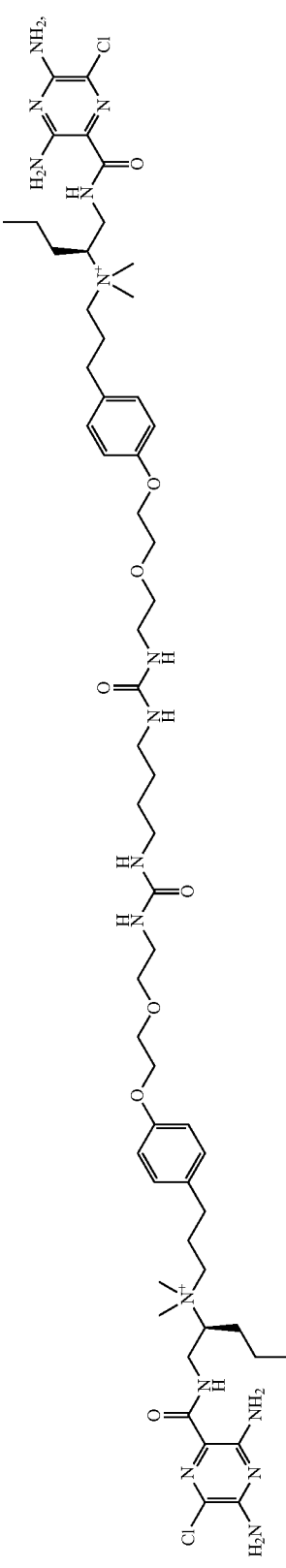
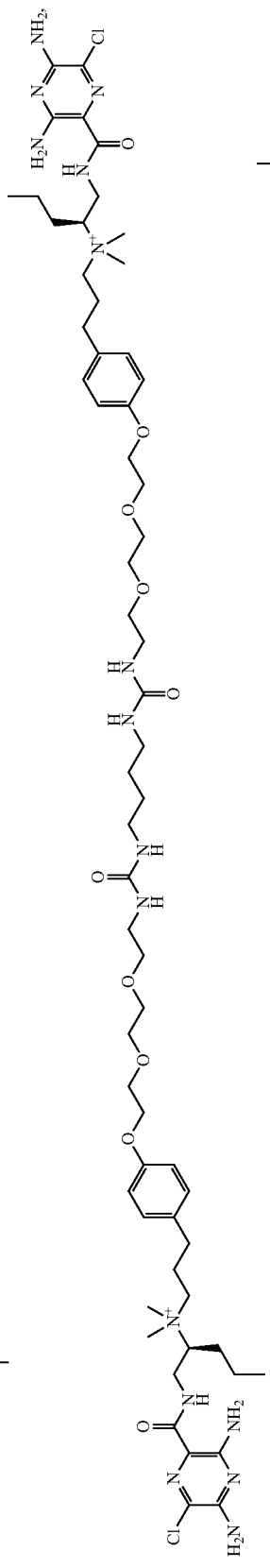
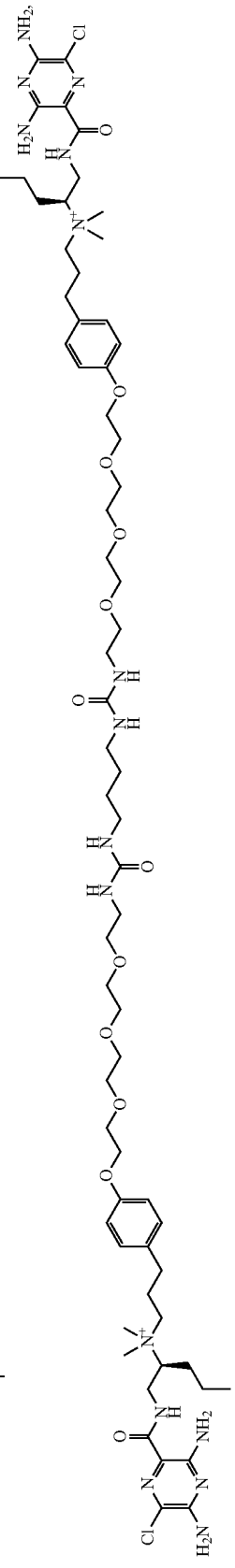
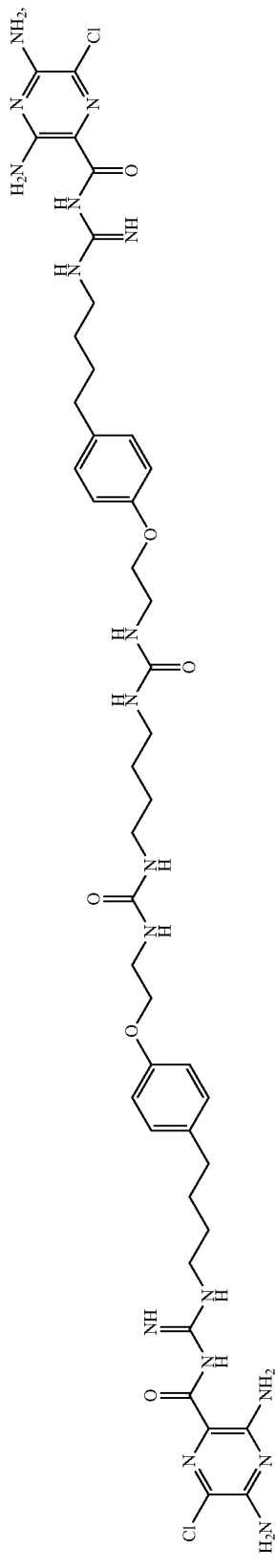

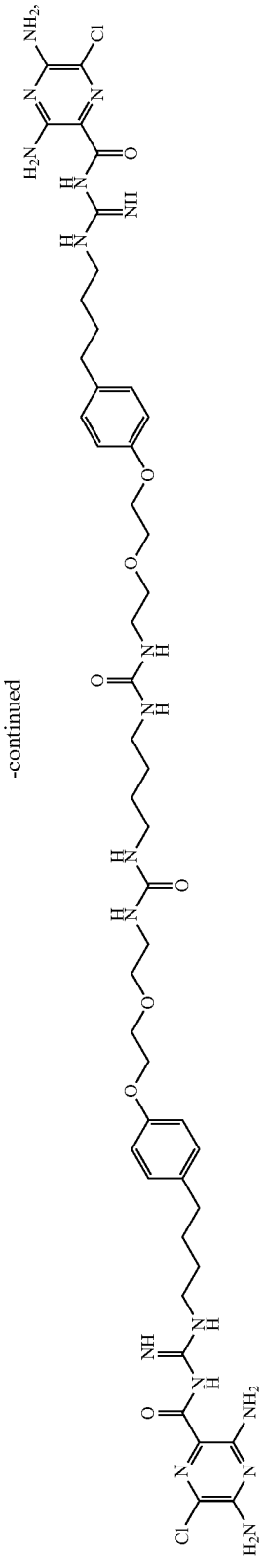
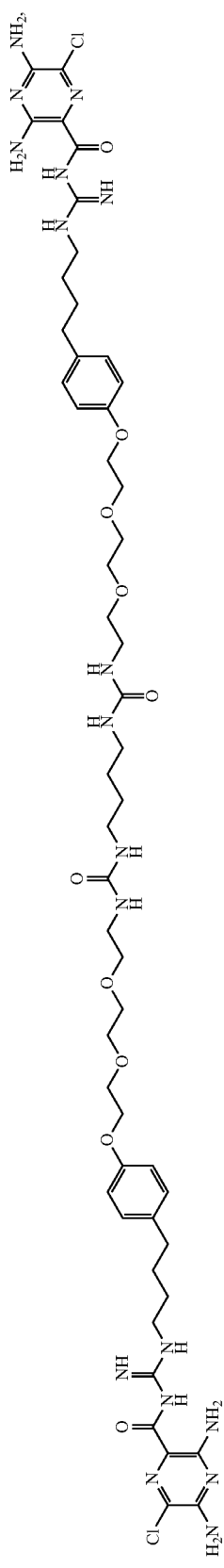
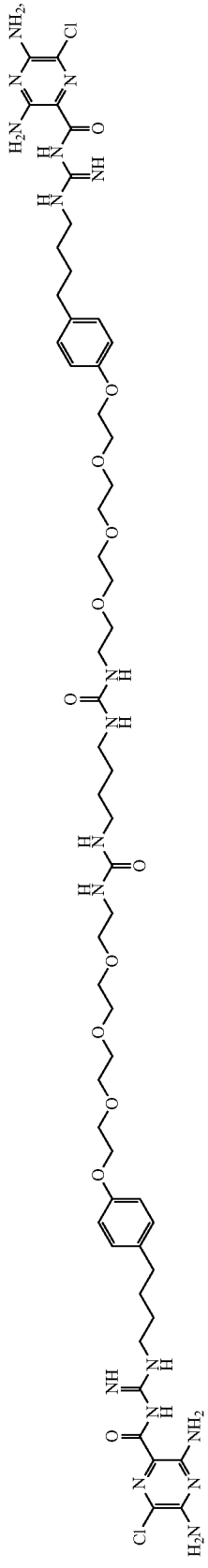

-continued
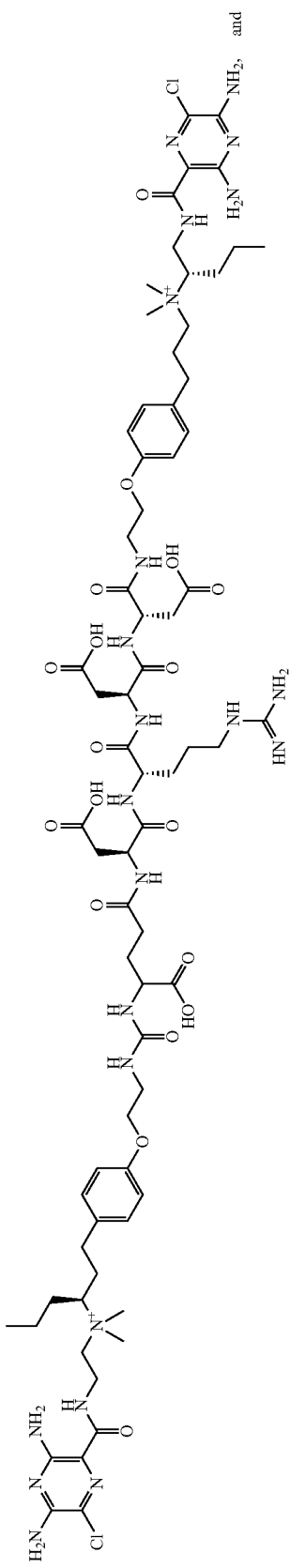 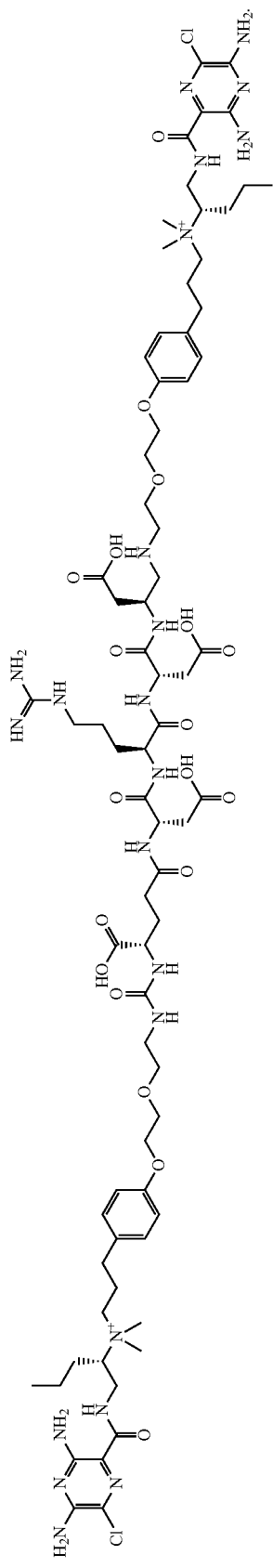

17. The compound of claim 1 wherein the compound is selected from:

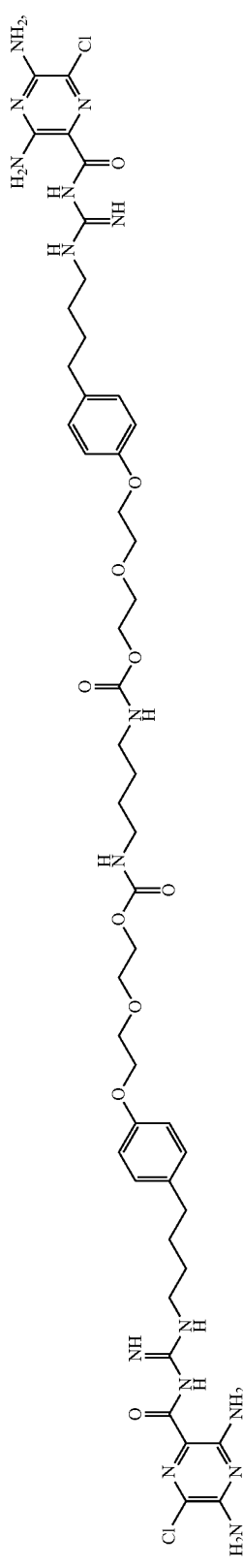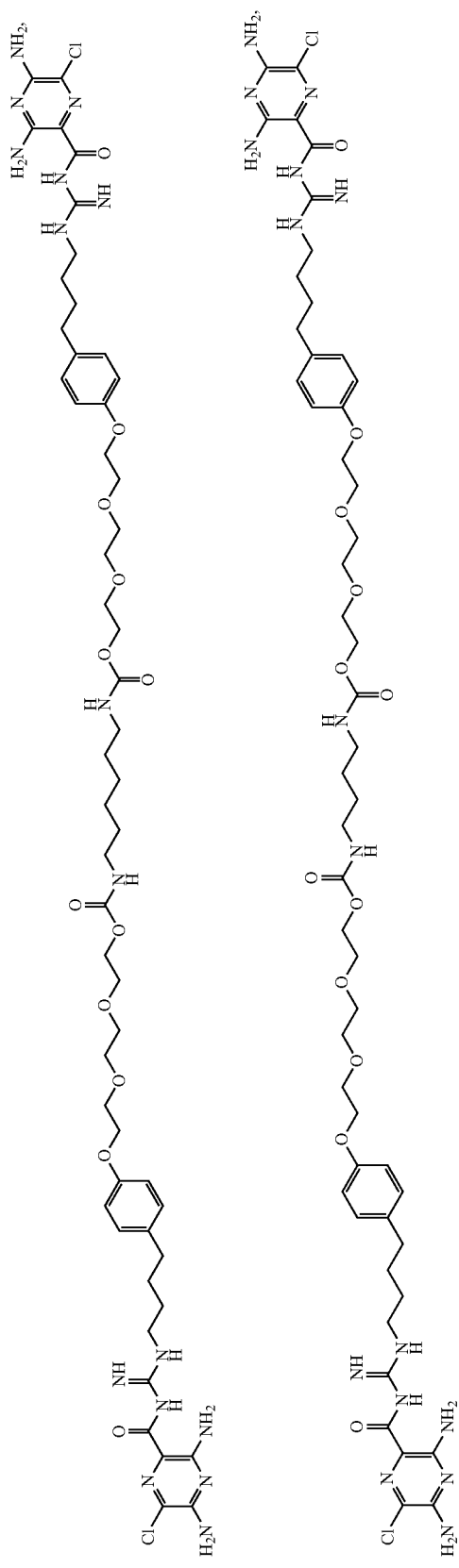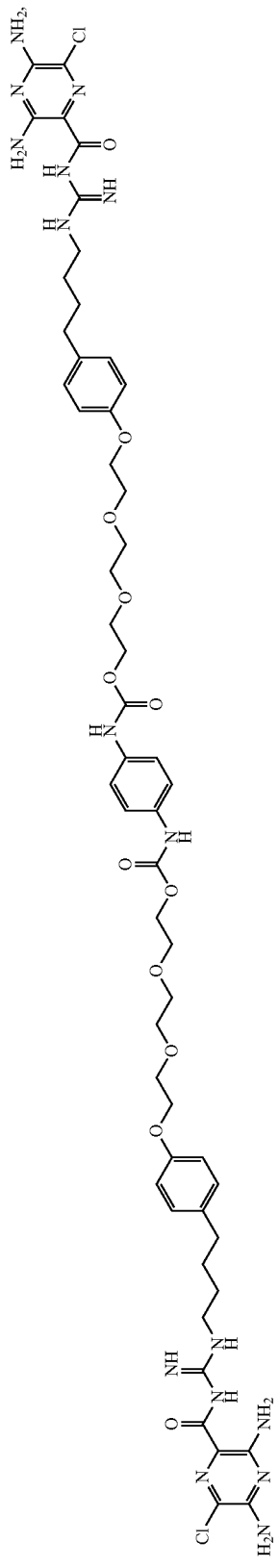

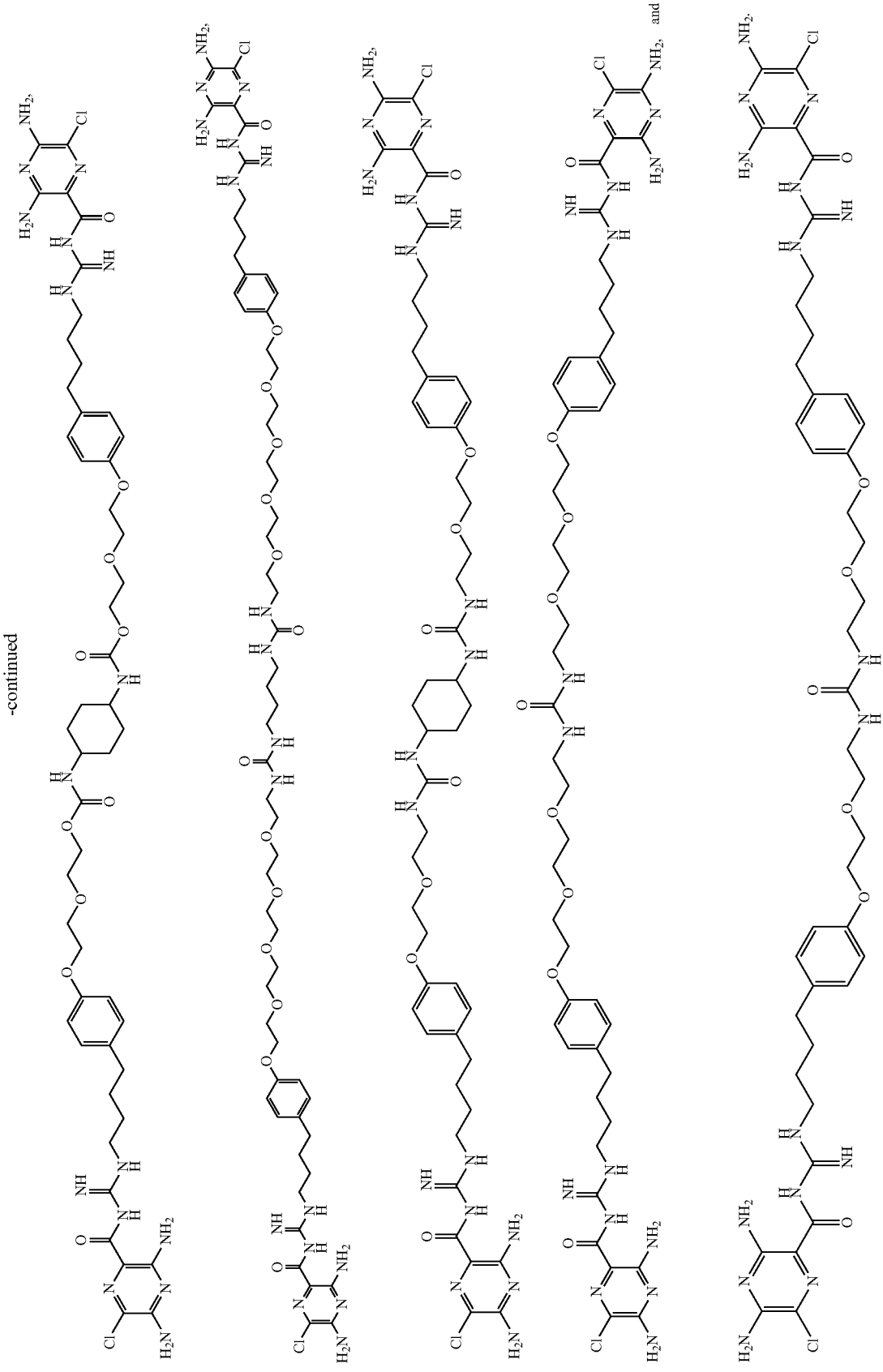

18. A pharmaceutical composition comprising a compound of claim 1 or a pharmaceutically acceptable salt, solvate, polymorph, prodrug, metabolite, deuteride, N-oxide, stereoisomer, or isomer thereof, and a pharmaceutically acceptable excipient.

19. A method to treat cystic fibrosis in a subject in need thereof, the method comprising administering a composition comprising a compound of claim 1, or a pharmaceutically acceptable salt, solvate, polymorph, prodrug, metabolite, deuteride, N-oxide, stereoisomer, or isomer thereof.

20. A method to treat chronic obstructive pulmonary disease (COPD) in a subject in need thereof, the method comprising administering a composition comprising a compound of claim 1, or a pharmaceutically acceptable salt, solvate, polymorph, prodrug, metabolite, deuteride, N-oxide, stereoisomer, or isomer thereof.

* * * * *

UNITED STATES PATENT AND TRADEMARK OFFICE
CERTIFICATE OF CORRECTION

Page 1 of 2

PATENT NO. : 9,656,972 B2
APPLICATION NO. : 14/900355
DATED : May 23, 2017
INVENTOR(S) : Peter G. Schultz et al.

It is certified that error appears in the above-identified patent and that said Letters Patent is hereby corrected as shown below:

Column 81:
Replace the following structure:

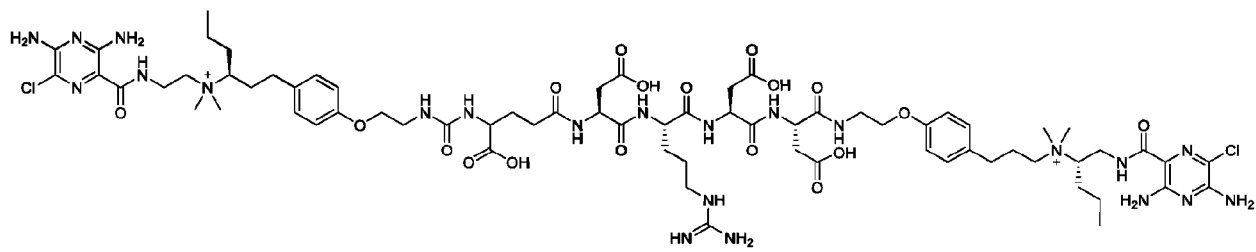

With the following structure:

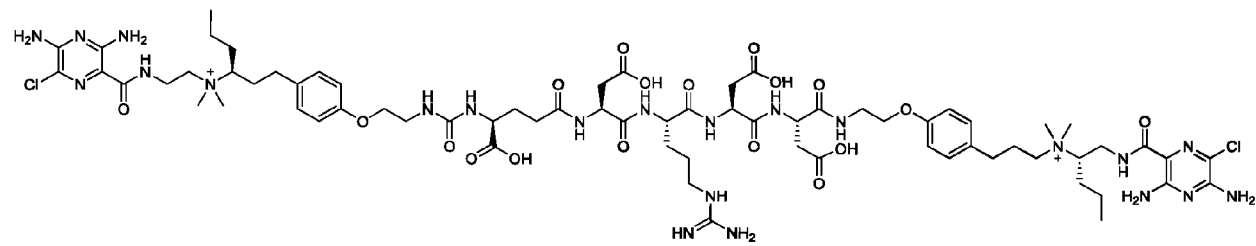

Claim 1 (Column 161, Lines 20-25):
Replace the following structure:

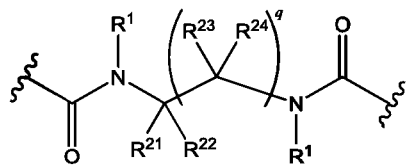

Signed and Sealed this
Twenty-sixth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,656,972 B2

With the following structure:

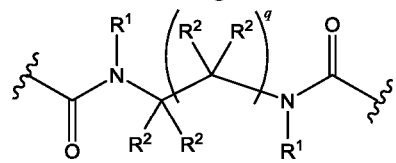

Claim 16 (Column 173):
Replace the following structure:

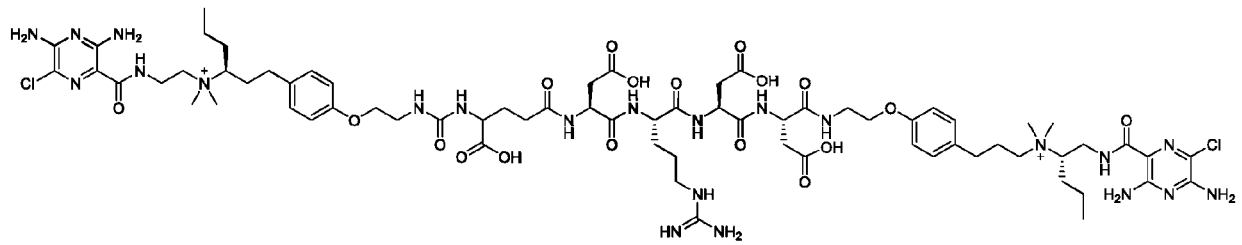

With the following structure: